US009133159B2

(12) United States Patent
Skolnick et al.

(10) Patent No.: US 9,133,159 B2
(45) Date of Patent: Sep. 15, 2015

(54) 1-HETEROARYL-3-AZABICYCLO[3.1.0] HEXANES, METHODS FOR THEIR PREPARATION AND THEIR USE AS MEDICAMENTS

(71) Applicant: NEUROVANCE, Inc., Cambridge, MA (US)

(72) Inventors: Phil Skolnick, Edgewater, NJ (US); Zhengming Chen, Belle Meade, NJ (US)

(73) Assignee: NEUROVANCE, INC., Cambridge, MA (US)

( * ) Notice: Subject to any disclaimer, the term of this patent is extended or adjusted under 35 U.S.C. 154(b) by 0 days.

(21) Appl. No.: 13/856,431

(22) Filed: Apr. 3, 2013

(65) Prior Publication Data

US 2014/0303207 A1    Oct. 9, 2014

Related U.S. Application Data

(63) Continuation of application No. 13/669,438, filed on Nov. 5, 2012, now abandoned, which is a continuation of application No. 13/425,371, filed on Mar. 20, 2012, now abandoned, which is a continuation of application No. 13/221,892, filed on Aug. 30, 2011, now abandoned, which is a continuation of application No. 13/048,852, filed on Mar. 15, 2011, now abandoned, which is a continuation of application No. 12/895,788, filed on Sep. 30, 2010, now abandoned, which is a continuation of application No. 12/135,053, filed on Jun. 6, 2008, now abandoned.

(60) Provisional application No. 60/933,631, filed on Jun. 6, 2007.

(51) Int. Cl.
| | |
|---|---|
| *A61K 31/47* | (2006.01) |
| *C07D 215/00* | (2006.01) |
| *C07D 405/00* | (2006.01) |
| *C07D 409/00* | (2006.01) |
| *C07D 411/00* | (2006.01) |
| *C07D 413/00* | (2006.01) |
| *C07D 417/00* | (2006.01) |
| *C07D 419/00* | (2006.01) |
| *C07D 401/04* | (2006.01) |
| *C07D 403/04* | (2006.01) |
| *C07D 405/04* | (2006.01) |
| *C07D 409/04* | (2006.01) |
| *C07D 417/04* | (2006.01) |

(52) U.S. Cl.
CPC ............ *C07D 401/04* (2013.01); *C07D 403/04* (2013.01); *C07D 405/04* (2013.01); *C07D 409/04* (2013.01); *C07D 417/04* (2013.01)

(58) Field of Classification Search
CPC ............................. C07D 401/04; C07D 403/04
USPC ........... 514/314; 546/152, 256; 548/454, 455, 548/465
See application file for complete search history.

(56) References Cited

U.S. PATENT DOCUMENTS

| | | | |
|---|---|---|---|
| 3,892,722 A | 7/1975 | Babitsky et al. | |
| 4,022,652 A | 5/1977 | Hirano et al. | |
| 4,088,652 A * | 5/1978 | Fanshawe et al. ............ | 548/515 |
| 4,118,393 A | 10/1978 | Fanshawe et al. | |
| 4,118,417 A * | 10/1978 | Epstein ........................ | 562/401 |
| 4,122,193 A | 10/1978 | Scherm et al. | |
| 4,131,611 A | 12/1978 | Fanshawe et al. | |
| 4,196,120 A | 4/1980 | Fanshawe et al. | |
| 4,231,935 A | 11/1980 | Fanshawe et al. | |
| 4,336,268 A | 6/1982 | Bruderer et al. | |
| 4,435,419 A | 3/1984 | Epstein et al. | |
| 4,467,102 A | 8/1984 | Toda et al. | |
| 4,504,657 A | 3/1985 | Bouzard et al. | |
| 4,521,431 A | 6/1985 | Crookes | |
| 4,591,598 A | 5/1986 | Urbach et al. | |
| 5,039,680 A | 8/1991 | Imperato et al. | |
| 5,075,341 A | 12/1991 | Mendelson et al. | |
| 5,130,430 A | 7/1992 | Shaw | |
| 5,198,459 A | 3/1993 | Imperato et al. | |
| 5,232,934 A | 8/1993 | Downs | |
| 5,488,056 A | 1/1996 | Bodick et al. | |
| 5,556,837 A | 9/1996 | Nestler et al. | |
| 5,556,838 A | 9/1996 | Mayer et al. | |
| 5,574,052 A | 11/1996 | Rose et al. | |
| 5,672,360 A | 9/1997 | Sackler et al. | |
| 5,762,925 A | 6/1998 | Sagen | |
| 5,911,992 A | 6/1999 | Braswell et al. | |
| 5,916,920 A | 6/1999 | Fernandez et al. | |
| 5,969,156 A | 10/1999 | Briggs et al. | |
| 5,985,864 A | 11/1999 | Imai et al. | |
| 6,109,269 A | 8/2000 | Rise et al. | |
| 6,121,261 A | 9/2000 | Glatt et al. | |
| 6,132,724 A | 10/2000 | Blum | |
| 6,194,000 B1 | 2/2001 | Smith et al. | |
| 6,204,284 B1 * | 3/2001 | Beer et al. .................... | 514/412 |
| 6,245,357 B1 | 6/2001 | Edgren et al. | |

(Continued)

FOREIGN PATENT DOCUMENTS

| | | |
|---|---|---|
| AU | 519620 B2 | 12/1981 |
| BE | 858683 | 3/1978 |

(Continued)

OTHER PUBLICATIONS

Marks et al., Drugs of the Future (2012), 37(4), 241-246.*

(Continued)

*Primary Examiner* — Niloofar Rahmani
(74) *Attorney, Agent, or Firm* — Hoxie & Associates LLC

(57) ABSTRACT

The invention provides novel 1-heteroaryl-3-azabicyclo [3.1.0]hexanes, and related processes and intermediates for preparing these compounds, as well as compositions and methods employing these compounds for the treatment and/ or prevention of central nervous system (CNS) disorders, including but not limited to depression and anxiety.

41 Claims, No Drawings

(56) References Cited

U.S. PATENT DOCUMENTS

| | | | |
|---|---|---|---|
| 6,245,911 | B1 | 6/2001 | Imai et al. |
| 6,268,507 | B1 | 7/2001 | Massey et al. |
| 6,372,919 | B1* | 4/2002 | Lippa et al. ............. 548/452 |
| 6,569,887 | B2 | 5/2003 | Lippa et al. |
| 6,716,868 | B2 | 4/2004 | Lippa et al. |
| 7,041,835 | B2 | 5/2006 | Lippa et al. |
| 7,081,471 | B2 | 7/2006 | Lippa et al. |
| 7,094,799 | B2* | 8/2006 | Russell et al. ............ 514/412 |
| 7,098,229 | B2 | 8/2006 | Lippa et al. |
| 7,098,230 | B2 | 8/2006 | Lippa et al. |
| 7,745,458 | B2* | 6/2010 | Arista et al. ............. 514/292 |
| 7,799,815 | B2 | 9/2010 | Bonanomi et al. |
| 7,855,298 | B2 | 12/2010 | Arista et al. |
| 7,947,683 | B2 | 5/2011 | Bonanomi et al. |
| 8,138,377 | B2 | 3/2012 | Skolnick et al. |
| 2004/0127541 | A1 | 7/2004 | Codd et al. |
| 2006/0223875 | A1 | 10/2006 | Skolnick et al. |
| 2007/0082939 | A1 | 4/2007 | Lippa et al. |
| 2007/0142438 | A1 | 6/2007 | Arista et al. |
| 2008/0058398 | A1 | 3/2008 | Anderton et al. |
| 2008/0269348 | A1 | 10/2008 | Skolnick et al. |
| 2008/0293822 | A1 | 11/2008 | Skolnick et al. |
| 2009/0036461 | A1* | 2/2009 | Hamprecht et al. ...... 514/252.06 |
| 2009/0069374 | A1* | 3/2009 | Skolnick et al. ........... 514/314 |
| 2009/0124629 | A1 | 5/2009 | Bonanomi et al. |
| 2009/0221593 | A1 | 9/2009 | Bonanomi et al. |
| 2009/0221618 | A1 | 9/2009 | Arista et al. |
| 2013/0123238 | A1* | 5/2013 | McKinney et al. .......... 514/215 |

FOREIGN PATENT DOCUMENTS

| | | |
|---|---|---|
| BE | 893707 | 12/1982 |
| WO | WO 01/22933 A1 | 4/2001 |
| WO | WO 03/047568 A1 | 6/2003 |
| WO | WO 2005/080382 A1 | 9/2005 |
| WO | WO 2006/023659 A2 | 3/2006 |
| WO | WO 2006/096810 A2 | 9/2006 |
| WO | WO 2006/108701 A1 | 10/2006 |
| WO | WO 2007/006117 A1 | 1/2007 |
| WO | WO 2007/016155 A2 | 2/2007 |
| WO | WO 2007/022933 A1 | 3/2007 |
| WO | WO 2007/022934 A2 | 3/2007 |
| WO | WO 2007/022980 A1 | 3/2007 |
| WO | WO 2008/022994 A1 | 2/2008 |
| WO | 2013019271 * | 2/2013 |

OTHER PUBLICATIONS

Clemens et al., Journal of Organic Chemistry (2013), 78(2), 780-785.*
Warnock et al., Pharmacology, Biochemistry and Behavior (2012), 103(1), 111-118.*
Polonski et al., Journal of the American Chemical Society (1993), 115(24), 11410-17.*
Zhang et al., Bioorganic & Medicinal Chemistry Letters (2008), 18(13), 3682-3686.*
U.S. Appl. No. 60/661,662, filed Mar. 8, 2005, Skolnick et al.
U.S. Appl. No. 60/701,562, filed Jul. 22, 2005, Skolnick et al.
U.S. Appl. No. 60/702,800, filed Jul. 26, 2005, Lippa et al.
U.S. Appl. No. 11/371,178, filed Mar. 7, 2006, Skolnick et al.
Atkinson, J. et al., "Effects of Noradrenergic and Serotonergic Antidepressants on Chronic Low Back Pain Intensity," Pain, 1999, 83, 137-145.
Basile, A. et al., "Characterization of the Antinociceptive Actions of Bicifadine in Models of Acute, Persistent, and Chronic Pain," The Journal of Pharmacology and Experimental Therapeutics, 2007, 321 (3), 1208-1225.
Briley, M., "Clinical Experience with Dual Action Antidepressants in Different Chronic Pain Syndromes," Human Psychopharmacology: Clinical and Experimental, 2004, 19, S21-S25.
Eshleman, A. et al., "Characteristics of Drug Interactions with Recombinant Biogenic Amine Transporters Expressed in the Same Cell Type," The Journal of Pharmacology and Experimental Therapeutics, 1999, 289 (2), 877-885.
Gu, H. et al., "Stable Expression of Biogenic Amine Transporters Reveals Differences in Inhibitor Sensitivity, Kinetics, and Ion Dependence," The Journal of Biological Chemistry, 1994, 269 (10), 7124-7130.
International Preliminary Report on Patentability for International Application No. PCT/US2008/007116, Date of issuance of the report Dec. 7, 2009, 9 pages.
International Search Report for International Application No. PCT/US2008/007116, Date of mailing of the International Search Report Dec. 19, 2008, 4 pages.
Perovic, S. et al., "Pharmacological Profile of Hypericum Extract, Effect on Serotonin Uptake by Postsynaptic Receptors," Arzneimittel Forschung/Drug Research, 1995, 45 (II), 11, 1145-1148.
Povlock, S. et al., Chapter 1 entitled "The Structure and Function of Norepinephrine, Dopamine, and Serotonin Transporters," pp. 1-28, in Neurotransmitter Transporters: Structure, Function, and Regulation, Reith, M., Ed., Humana Press, New Jersey, 1997.
Skolnick, P., Chapter 9 entitled "Dopamine and Depression," pp. 199-214, in Dopamine and Glutamate in Psychiatric Disorders, Schmidt, W. et al., Eds. Humana Press, New Jersey, 2005.
Skolnick, P. et al., "Preclinical and Clinical Pharmacology of DOV 216,303, a 'Triple' Reuptake Inhibitor," CNS Drug Reviews, 2006, 12 (2), 123-134.
Zhang, M. et al., "Studies on the Structure-Activity Relationship of Bicifadine Analogs as Monoamine Transporter Inhibitors," Bioorganic and Medicinal Chemistry Letters, 2008, 18, 3682-3686.
Baldessarini, R., "Drugs and the Treatment of Psychiatric Disorders" in Goodman and Gilman's The Pharmacological Basis of Therapeutics, Ninth Edition, J.G. Hardman et al., Eds., McGraw-Hill, New York, 1996, p. 399 and Chapter 18, pp. 431-459.
Bayes, M. et al., "Gateways to Clinical Trials," Methods and Findings in Experimental and Clinical Pharmacology, 2003, 25 (3), 225-248.
Beer, B. et al., "DOV 216,303, A 'Triple' Reuptake Inhibitor: Safety, Tolerability, and Pharmacokinetic Profile," The Journal of Clinical Pharmacology, 2004, 44 (12), 1360-1367.
Blum, K. et al., "Dopamine D2 Receptor Gene Variants: Association and Linkage Studies in Impulsive-Addictive-Compulsive Behaviour," Pharmacogenetics, 1995, 5 (3), 121-141.
Bray, G., "A Concise Review on the Therapeutics of Obesity," Nutrition, 2000, 16 (10), 953-960.
Caira, M., "Crystalline Polymorphism of Organic Compounds," Topics in Current Chemistry, 1998, 198, 163-208.
Casadio, S. et al., "Acide Phenyl-1-Hydroxymethyl-2-Cyclopropane Carboxylique Et Derives," Bollettino Chimico Farmaceutico, 1978, 117, 331-342.
Crown, W., "Economic Outcomes Associated with Tricyclic Antidepressant and Selective Serotonin Reuptake Inhibitor Treatments for Depression,"Acta Psychiatrica Scandinavica Supplementum, 2000, 403, 62-66.
Czobor, P., "A Double-Blind, Placebo Controlled Randomized Study of DOV 220,075 (Bicifadine) SR and Codeine 60 mg in the Treatment of Post-Operative Dental Pain," American Pain Society 2003, Abstract (915).
Czobor, P., "A Two Center Double-Blind Placebo-Controlled Randomized Study of DOV 220,075 (Bicifadine) SR and Tramadol 100 mg in the Treatment of Post-Operative Dental Pain," American Pain Society, 2004, Abstract (801).
D'Aquila, P.S. et al., "The Role of Dopamine in the Mechanism of Action of Antidepressant Drugs," European Journal of Pharmacology, 2000, 405 (1-3), 365-373.
Epstein, J. et al., "1-Aryl-3-azabicyclo[3.1.0]hexanes, A New Series of Nonnarcotic Analgesic Agents," Journal of Medicinal Chemistry, 1981, 24 (5), 481-490.
Epstein, J. et al., "Bicifadine: Non-Narcotic Analgesic Activity of 1-Aryl-3-Azabicycl[3.1.0]Hexanes," NIDA Research Monograph, 1982, 41, 93-98.
Ettmayer, P. et al., "Lessons Learned from Marketed and Investigational Prodrugs," Journal of Medicinal Chemistry, 2004, 47 (10), 2393-2404.
Fauci, A. et al., Eds., Harrison's Principles of Internal Medicine, Fourteenth Edition, 1998, pp. 2485-2503.
Frazer, A., "Norepinephrine Involvement in Antidepressant Action," Journal of Clinical Psychiatry, 2000, 61 (Suppl. 10), 25-30.

(56) References Cited

OTHER PUBLICATIONS

Fredman, S. et al., "Partial Response, Nonresponse, and Relapse with Selective Serotonin Reuptake Inhibitors in Major Depression: A Survey of Current 'Next-Step' Practices," Journal of Clinical Psychiatry, 2000, 61 (6), 403-408.
Grant, J., Ed., Hackh's Chemical Dictionary, Fourth Edition, McGraw-Hill Book Company, New York, 1969, pp. 474-475.
Hitri, A. et al., "Molecular, Functional and Biochemical Characteristics of the Dopamine Transporter: Regional Differences and Clinical Relevance," Clinical Neuropharmacology, 1994, 17 (1), 1-22.
Hoffman, B. et al., "Localization and Dynamic Regulation of Biogenic Amine Transporters in the Mammalian Central Nervous System,"Frontiers in Neuroendocrinology, 1998, 19 (3), 187-231.
Kiyatkin, E., "Dopamine Mechanisms of Cocaine Addiction," The International Journal of Neuroscience, 1994, 78 (1-2), 75-101.
Kreek, M., "Cocaine, Dopamine and the Endogenous Opiod System," Journal of Addictive Diseases, 1996, 15(14), 73-96.
Leonhardt, M. et al., "New Approaches in the Pharmacological Treatment of Obesity," European Journal of Nutrition, 1999, 38 (1), 1-13.
Lima, L. et al., "Bioisosterism: A Useful Strategy for Molecular Modification and Drug Design," Current Medicinal Chemistry, 2005, 12 (1), 23-49.
McArdle, P. et al., "A Method for the Prediction of the Crystal Structure of Ionic Organic Compounds—The Crystal Structure of O-Toluidinium Chlorid and Bromide and Polymorphism of Bicifadine Hydrochloride," CrystEngComm, 2004, 6 (53), 303-309.
McBriar, M. et al., "Discovery of Bicycloalkyl Urea Melanin Concentrating Hormone Receptor Antagonists: Orally Efficacious Antiobesity Therapeutics,"Journal of Medicinal Chemistry, 2005, 48 (7) 2274-2277.
McBriar, M. et al., "Discovery of Orally Efficacious Melanin-Concentrating Hormone Receptor01 Antagonists as Antiobesity Agents. Synthesis, SAR, and Biological Evaluation of Bicyclo[3.1.0]hexyl Ureas," Journal of Medicinal Chemisty, 2006, 49 (7), 2294-2310.
McMillen, B. et al., "Effect of DOV 102,677 on the Volitional Consumption of Ethanol by Myers' High Ethanol-Preferring Ray," Alcoholism, Clinical and Experimental Research, 2007, 31 (11), 1866-1871.
Meyerson, L. et al., "Allosteric Interaction Between the Site Labeled by [$^3$H]Imipramine and the Serotonin Transporter in Human Platelets," Journal of Neurochemistry, 1987, 48 (2), 560-565.
Micheli, F. et al., "1-(Aryl)-6-[alkoxyalkyl]-3-azabicyclo [3.1.0]hexanes and 6-(Aryl)-6-[alkoxyalkyl]-3-azabicyclo [3.1.0]hexanes: A New Series of Potent and Selective Triple Reuptake Inhibitors," Journal of Medicinal Chemistry, 2010, 53 (6), 2534-2551.
Morissette, S. et al., "High-Throughput Crystallization: Polymorphs, Salts, Co-Crystals and Solvates of Pharmaceutical Solids," Advanced Drug Delivery Reviews, 2004, 56 (3), 275-300.
Nagatsu, T. et al., "Changes in Cytokines and Neurotrophins in Parkinson's Disease," Journal of Neural Transmission. Supplementa, 2000, 60, 277-290.
Noble, E., "Polymorphisms of the D2 Dopamine Receptor Gene and Alcoholism and Other Substance Use Disorders," Alcohol and Alcoholism—Supplements, 1994, 2, 35-43.
"Pain Therapeutics Takes Different Path, Improving Long-term Pain Relief by Reducing Dependency and Tolerance," Genetic Engineering and Biotechnology News, 2006, 26 (12), 2 pages.
Porter, E., "Single Dose Comparison of Bicifadine, Codeine, and Placebo in Postoperative Pain," Current Therapeutic Research, 1981, 30 (3), 156-160.
Scates, A. et al., "Reboxetine: A Selective Neorepinephrine Reuptake Inhibitor for the Treatment of Depression," The Annals of Pharmacotherapy, 2000, 34 (11), 1302-1312.
Shuto, S. et al., "Synthesis of (+)- and (−)-Milnaciprans and Their Conformationally Restricted Analogs," Tetrahedron Letters, 1996, 37 (5), 641-644.
Simon, G. et al., "TCAs or SSRIs As Initial Therapy for Depression," Journal of Family Practice, 1999, 48, 845-846.
Skolnick, P., "Beyond Monoamine-Based Therapies: Clues to New Approaches," Journal of Clinical Psychiatry, 2002, 63 (Suppl. 2), 19-23.
Skolnick, P. et al., "Antidepressant-like Actions of DOV 21,947, A 'Triple' Uptake Inhibitor," European Journal of Pharmacology, 2003, 461, 99-104.
Skolnick, P. et al., "'Broad Spectrum' Antidepressants: Is More Better for the Treatment of Depression," Life Sciences, 2003, 73 (25), 3175-3179.
Stacy, M. et al., "Treatment Options for Early Parkinson's Disease," American Family Physician, 1996, 53 (4), 1281-1287.
Stella, V., "Prodrugs as Therapeutics," Expert Opinion on Therapeutic Patents, 2004, 14 (3), 277-280.
Sullivan, A. et al., "Mechanisms of Appetite Modulation by Drugs," Federation Proceedings, 1985, 44 (1 Pt. 1), 139-144.
Taylor, A. et al., "Scales for the Identification of Adults with Attention Deficit Hyperactivity Disorder (ADHD): A Systematic Review," Research in Developmental Disabilities, 2011, 32 (3), 924-938.
Testa, B., "Prodrug Research: Futile or Fertile," Biochemical Pharmacology, 2004, 68 (11), 2097-2106.
Theeuwes, F., "Drug Delivery Fuels Specialty Pharma, Rich Source of Innovation Now Significant Platform to Launch New Companies," Genetic Engineering and Biotechnology News, 2007, 27 (10), 2 pages.
Vippagunta, S. et al., "Crystalline Solids," Advanced Drug Delivery Reviews, 2001, 48 (1), 3-26.
Wang, R. et al., "The Oral Analgesic Efficacy of Bicifadine Hydrochloride in Postopeartive Pain," The Journal of Clinical Pharmacology, 1982, 22 (4), 160-164.
Wolff, M., Ed., Burger's Medicinal Chemistry, Fifth Edition, vol. 1, pp. 975-977.
Wong, E. et al., "Reboxetine: A Pharmacologically Potent, Selective, and Specific Norepinephrine Reuptake Inhibitor," Biological Psychiatry, 2000, 47 (9), 818-829.
Xu, F. et al., "Stereocontrolled Synthesis of Trisubstituted Cyclopropanes: Expedient, Atom-Economical, Asymmetric Syntheses of (+)-Bicifadine and DOV21947," Organic Letters, 2006, 8 (17), 3885-3888.

* cited by examiner

1-HETEROARYL-3-AZABICYCLO[3.1.0] HEXANES, METHODS FOR THEIR PREPARATION AND THEIR USE AS MEDICAMENTS

This application is a continuation of U.S. patent application Ser. No. 13/669,438, filed Nov. 5, 2012, which is a continuation of U.S. patent application Ser. No. 13/425,371, filed Mar. 20, 2012, which is a continuation of U.S. patent application Ser. No. 13/221,892, filed Aug. 30, 2011, which is a continuation of U.S. patent application Ser. No. 13/048,852, filed Mar. 15, 2011, which is a continuation of U.S. patent application Ser. No. 12/895,788, filed Sep. 30, 2010, which is a continuation of U.S. patent application Ser. No. 12/135,053, filed Jun. 6, 2008, which claims the benefit of United States Provisional Patent Application No. 60/933,631, filed Jun. 6, 2007, which is incorporated herein by reference in its entirety.

TECHNICAL FIELD

The present invention relates to novel 1-heteroaryl-3-azabicyclo[3.1.0]hexanes, intermediates for the production thereof and methods for preparing, formulating, and using 1-heteroaryl-3-azabicyclo[3.1.0]hexanes.

BACKGROUND OF THE INVENTION

Phenyl substituted-3-azabicyclo[3.1.0]hexanes, exemplified by bicifadine (p-toly-3-azabicyclo[3.1.0]hexane) and 1-(3,4-dichlorophenyl)-3-azabicyclo[3.1.0]hexane have been reported to inhibit the uptake of biogenic amines (serotonin, norepinephrine and dopamine) that serve as neurotransmitters in the central nervous system. Basile, A. S., et al., *J. Pharmacol. Exp. Ther.*, 321:1208-1225 (2007).; Skolnick, P. et al., Eur. J. Pharmacol. 461:99 (2003); Skolnick, P. et al., Life Sci. 73: 3175-3179 (2003); Skolnick, P., et al., CNS Drug Reviews (2006)] Related compounds have also been described in U.S. patent application Ser. No. 11/371,178 filed on Mar. 7, 2006, which is related to and claims priority from US Provisional Applications 60/661,662, filed on Mar. 8, 2005 and 60/701,562 filed on Jul. 22, 2005, the disclosures of which are incorporated herein by reference in their entirety. Biogenic amines are widely distributed throughout the central nervous system and have been implicated in a variety of neurological and psychiatric disorders ranging from acute and chronic pain syndromes, and neuropathic disorders, to affective disorders such as depression and anxiety. [Briley, M., Hum. Psychopharmacol. Clin. Exp. 19:S21-S25 (2004); Skolnick, P. in "*Dopamine and glutamate in psychiatric disorders*," W. Schmidt, Editor; Humana Press, Totowa, Chapter 9, pp. 199-214 (2005)]. Compounds inhibiting the uptake of these neurotransmitters (resulting in increased concentrations of norepinephrine, serotonin and/or dopamine in the synaptic cleft) may therefore be useful in treating these disorders. [Skolnick, P., et al., CNS Drug Reviews (2006); Briley, M., Hum. Psychopharmacol. Clin. Exp. 19:S21-S25 (2004)]

The effectiveness of a neurotransmitter uptake inhibitor in treating a neuropsychiatric disorder depends upon, at least in part, its relative potency as an inhibitor of serotonin versus norepinephrine versus dopamine uptake. For example, serotonin selective reuptake inhibitors (SSRIs) are commonly prescribed as antidepressants but are not very effective in treating pain [Atkinson, J. H. et al., Pain 83:137-145 (1999)], while compounds that inhibit the uptake of norepinephrine and serotonin (NSRIs) are useful in treating both depression and pain. Compounds inhibiting the reuptake of all three biogenic amines may have certain therapeutic advantages (e.g., faster onset; superior side effect profile) than single or dual uptake inhibitors. [Skolnick, P. et al., Eur. J. Pharmacol. 461:99 (2003); Skolnick, P. et al., Life Sci. 73: 3175-3179 (2003); Skolnick, P. in "*Dopamine and glutamate in psychiatric disorders*," W. Schmidt, Editor; Humana Press, Totowa, Chapter 9, pp. 199-214 (2005)]

The ability of phenyl substituted azabicyclohexanes to inhibit biogenic amine uptake is effected through binding to a family of distinct but related transport proteins that have been identified and can readily be expressed as recombinant proteins. [Povlock, S. L. and Amara, S. G., in "*Neurotransmitter transporters: structure, function, and regulation*," Reith MEA, Editor, Humana Press, Totowa, pp. 1-28 (1997); Eshleman, A J. et al., Journal of Pharmacology & Experimental Therapeutics 289:877-885 (1999)] The potency of a compound to inhibit biogenic amine uptake can be measured by standard neurochemical techniques [Skolnick, P. et al., Eur. J. Pharmacol. 461:99 (2003)] including radioligand binding and [$^3$H]biogenic amine (e.g., serotonin) uptake using such recombinant proteins expressed in, for example, a mammalian cell line. Such techniques are well known to those skilled in the art.

Notwithstanding the foregoing, there remains a compelling need to identify additional compounds that inhibit the reuptake of one, two, or three of these biogenic amines for the treatment of a variety of neurological and psychiatric disorders.

SUMMARY OF EXEMPLARY EMBODIMENTS OF THE INVENTION

It is therefore an object of the present invention to provide novel compounds capable of inhibiting the reuptake of multiple biogenic amines linked to neurological and psychiatric disorders, and to provide related compositions and methods for treating and managing a variety of neurological and psychiatric disorders, including depression and anxiety.

It is a further object of the present invention to produce and select novel 1-heteroaryl-3-azabicyclo[3.1.0]hexanes as therapeutic agents.

It is another object of the invention to provide new synthetic methods and compositions useful for producing 1-heteroaryl-3-azabicyclo[3.1.0]hexanes and related compounds.

It is an additional object of the invention to provide novel 1-heteroaryl-3-azabicyclo[3.1.0]hexane compositions and methods useful to treat or manage neurological and psychiatric disorders by modulating transport of one or more biogenic amines, for example to simultaneously inhibit or block the reuptake of norepinephrine and/or serotonin and/or dopamine.

The invention achieves these objects and satisfies additional objects and advantages by providing novel 1-heteroaryl-3-azabicyclo-[3.1.0]hexanes that possess unexpected activities for modulating biogenic amine transport.

In exemplary embodiments, novel arylbicyclo[3.1.0]hexylamines are provided that have the following Formula I:

Formula I

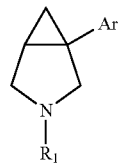

and enantiomers, polymorphs, solvates, hydrates, prodrugs and pharmaceutically acceptable salts thereof, wherein:

Ar is a heterocyclic aryl group selected from furan, thiophene, pyrrole, imidazole, pyrazole, triazole, tetrazole, thiazole, isothiazole, pyridine, pyridizine, pyrimidine, pyrazine, triazine, indole, benzofuran, benzothiophene, benzothiazole, quinoline, isoquinoline, cinnoline, phthalazine, quinazoline, quinoxaline, chromane and isochromane, and Ar is either unsubstituted or substituted with one or more substituents independently selected from fluoro, chloro, bromo, iodo, $-NO_2$, $-CN$, $-NH_2$, carboxy, $C_{1-8}$ alkyl, $C_{2-8}$ alkenyl, $C_{2-8}$ alkynyl, halo($C_{1-8}$)alkyl, hydroxy, trifluoromethyl, $C_{3-8}$ cycloalkyl, $C_{1-3}$ alkoxy, $C_{1-3}$ alkoxy($C_{1-3}$)alkyl, carboxy ($C_{1-3}$)alkyl, $C_{1-3}$ alkanoyl, halo($C_{1-3}$)alkoxyl, $C_{1-8}$ alkylamino, and di($C_{1-8}$)alkylamino; and $R_1$ is selected from hydrogen, unsubstituted $C_{1-10}$ alkyl, $C_{3-8}$ cycloalkyl, $C_{2-10}$alkenyl, and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy.

The invention also provides novel methods of making 1-heteroaryl-3-azabicyclo[3.1.0]hexanes, including synthetic methods that form novel intermediate compounds of the invention for producing 1-heteroaryl-3-azabicyclo-[3.1.0]hexanes. In related embodiments, the invention provides novel processes for preparing one or more 1-heteroaryl-3-azabicyclo-[3.1.0]hexanes, to yield novel compounds useful in biologically active and/or therapeutic compositions.

Useful 1-heteroaryl-3-azabicyclo[3.1.0]hexanes of the invention include the 1-heteroaryl-3-azabicyclo-[3.1.0]hexane compounds described herein, as well as their active, pharmaceutically acceptable salts, polymorphs, solvates, hydrates and/or prodrugs, or combinations thereof.

In yet additional embodiments, the invention provides pharmaceutical compositions and methods for treating disorders of the central nervous system (CNS), including a wide array of serious neurological or psychiatric conditions, in mammals that are amenable to treatment using agents that inhibit or otherwise modulate biogenic amine transport.

The forgoing objects and additional objects, features, aspects and advantages of the present invention are further exemplified and described in the following detailed description.

DETAILED DESCRIPTION OF EXEMPLARY EMBODIMENTS OF THE INVENTION

The instant invention provides novel, aryl-substituted and/or aza-substituted 1-heteroaryl-3-azabicyclo[3.1.0.]hexanes, as well as compositions and processes for producing these compounds. In exemplary embodiments, the invention provides compounds characterized in part by Formula II.

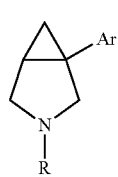

Formula II wherein Ar is a heterocyclic aryl group, optionally with or without substitution groups on the aryl ring, and wherein R is H or an optional substituent selected from, for example, hydrogen, $C_{1-6}$ alkyl, halo($C_{1-6}$)alkyl, $C_{3-9}$ cycloalkyl, $C_{1-5}$ alkoxy($C_{1-6}$)alkyl, carboxy($C_{1-3}$)alkyl, $C_{1-3}$ alkanoyl, carbamate, halo($C_{1-3}$)alkoxy($C_{1-6}$)alkyl, $C_{1-3}$ alkylamino($C_{1-6}$) alkyl, di($C_{1-3}$)alkylamino($C_{1-6}$)alkyl and cyano($C_{1-6}$)alkyl, more preferably, methyl, ethyl, trifluoromethyl, trifluoroethyl and 2-methoxyethyl.

The instant invention also provides novel 1-heteroaryl-3-azabicyclo-[3.1.0]hexanes having the following Formula I:

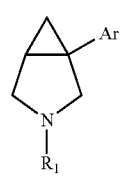

Formula I and enantiomers and pharmaceutically acceptable salts thereof, wherein:

Ar is a heterocyclic aryl group selected from furan, thiophene, pyrrole, imidazole, pyrazole, triazole, tetrazole, thiazole, isothiazole, pyridine, pyridizine, pyrimidine, pyrazine, triazine, indole, benzofuran, benzothiophene, benzothiazole, quinoline, isoquinoline, cinnoline, phthalazine, quinazoline, quinoxaline, chromane and isochromane, and Ar is either unsubstituted or substituted with one or more substituents independently selected from fluoro, chloro, bromo, iodo, $-NO_2$, $-CN$, $-NH_2$, carboxy, $C_{1-8}$ alkyl, $C_{2-8}$ alkenyl, $C_{2-8}$ alkynyl, halo($C_{1-8}$)alkyl, hydroxy, trifluoromethyl, $C_{3-8}$ cycloalkyl, $C_{1-3}$ alkoxy, $C_{1-3}$ alkoxy($C_{1-3}$)alkyl, carboxy ($C_{1-3}$)alkyl, $C_{1-3}$ alkanoyl, halo($C_{1-3}$)alkoxyl, $C_{1-8}$ alkylamino, and di($C_{1-8}$)alkylamino; and $R_1$ is selected from hydrogen, unsubstituted $C_{1-10}$ alkyl, $C_{3-8}$ cycloalkyl, $C_{2-10}$ alkenyl, and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy.

In certain embodiments, Ar is furane, thiophene, methyl furane, pyridine, methoxypyridine, benzofurane, benzothiophene, chlorobenzothiophene, quinoline, indole or methylindole and $R_1$ is hydrogen or unsubstituted $C_{1-10}$ alkyl.

In additional embodiments, $R_1$ is hydrogen, methyl, ethyl, propyl or isopropyl.

An illustrative assemblage of 1-heteroaryl-3-azabicyclo-[3.1.0]hexanes within this aspect of the invention is provided in Table 1.

TABLE 1

Exemplary 1-Heteroaryl-3-azabicyclo[3.1.0]hexanes

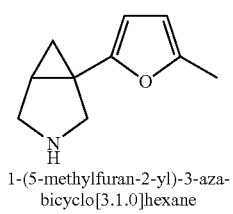

1-(5-methylfuran-2-yl)-3-aza-bicyclo[3.1.0]hexane

TABLE 1-continued

Exemplary 1-Heteroaryl-3-azabicyclo[3.1.0]hexanes

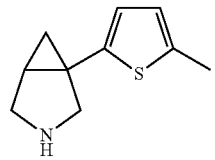

1-(5-methylthiophen-2-yl)-3-
aza-bicyclo[3.1.0]hexane

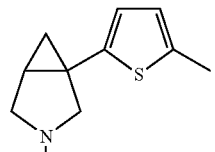

3-methyl-1-(5-methylthiophen-2-yl)-
3-aza-bicyclo[3.1.0]hexane

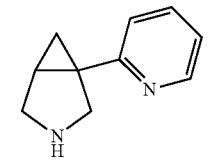 [SMILES: c1ccc(C23CNCC2C3)nc1]

1-(pyridin-2-yl)-3-aza-
bicyclo[3.1.0]hexane

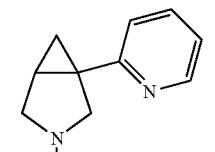

3-methyl-1-(pyridin-2-yl)-3-
aza-bicyclo[3.1.0]hexane

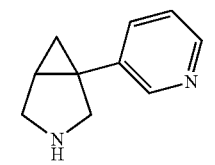 [SMILES: c1cncc(C23CNCC2C3)c1]

1-(pyridin-3-yl)-3-aza-
bicyclo[3.1.0]hexane

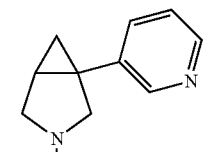

3-methyl-1-(pyridin-3-yl)-3-
aza-bicyclo[3.1.0]hexane

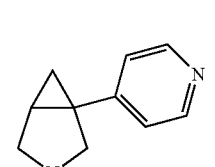

1-(pyridin-4-yl)-3-aza-
bicyclo[3.1.0]hexane

TABLE 1-continued

Exemplary 1-Heteroaryl-3-azabicyclo[3.1.0]hexanes

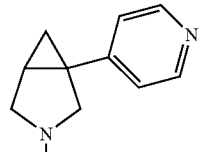

3-methyl-1-(pyridin-4-yl)-3-aza-
bicyclo[3.1.0]hexane

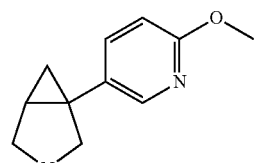

1-(6-methoxypyridin-3-yl)-3-
aza-bicyclo[3.1.0]hexane

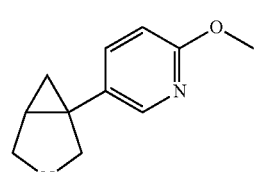

1-(6-methoxypyridin-3-yl)-3-
methyl-3-aza-bicyclo[3.1.0]hexane

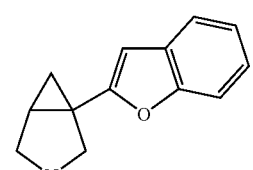

1-(benzofuran-2-yl)-3-methyl-3-
aza-bicyclo[3.1.0]hexane

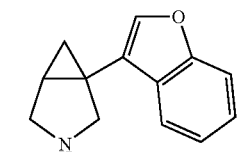

1-(benzofuran-3-yl)-3-aza-
bicyclo[3.1.0]hexane

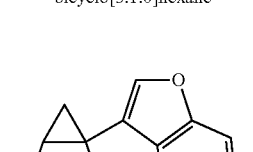

1-(benzofuran-3-yl)-3-methyl-3-
aza-bicyclo[3.1.0]hexane

TABLE 1-continued

Exemplary 1-Heteroaryl-3-azabicyclo[3.1.0]hexanes

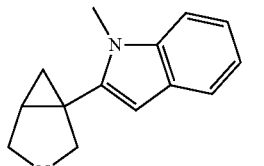

1-methyl-2-(3-methyl-3-aza-bicyclo[3.1.0]hexan-1-yl)-1H-indole

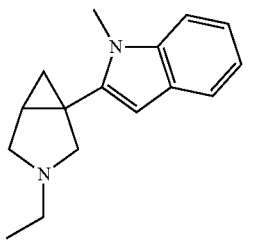 [SMILES: CCN1CC2CC2(c2cc3ccccc3n2C)C1]

2-(3-ethyl-3-aza-bicyclo[3.1.0]hexan-1-yl)-1-methyl-1H-indole

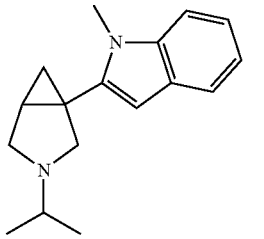 [SMILES: CC(C)N1CC2CC2(c2cc3ccccc3n2C)C1]

2-(3-isopropyl-3-aza-bicyclo[3.1.0]hexan-1-yl)-1-methyl-1H-indole

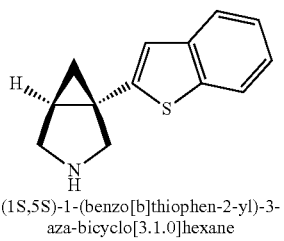

(1S,5S)-1-(benzo[b]thiophen-2-yl)-3-aza-bicyclo[3.1.0]hexane

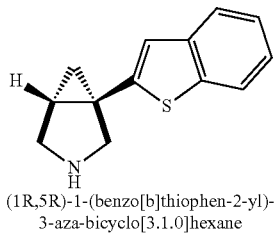

(1R,5R)-1-(benzo[b]thiophen-2-yl)-3-aza-bicyclo[3.1.0]hexane

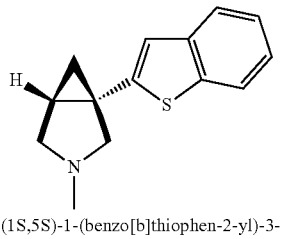

(1S,5S)-1-(benzo[b]thiophen-2-yl)-3-methyl-3-aza-bicyclo[3.1.0]hexane

TABLE 1-continued

Exemplary 1-Heteroaryl-3-azabicyclo[3.1.0]hexanes

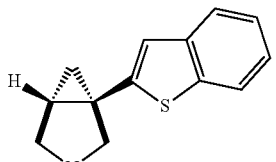

(1R,5R)-1-(benzo[b]thiophen-2-yl)-3-methyl-3-aza-bicyclo[3.1.0]hexane

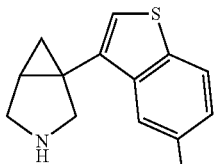

1-(5-chlorobenzo[b]thiophen-3-yl)-3-aza-bicyclo[3.1.0]hexane

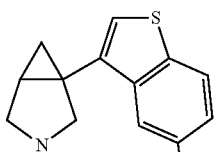

1-(5-chlorobenzo[b]thiophen-3-yl)-3-methyl-3-aza-bicyclo[3.1.0]hexane

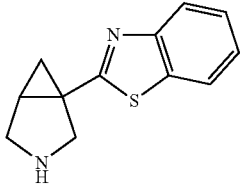

2-(3-aza-bicyclo[3.1.0]hexan-1-yl)benzo[d]thiazole

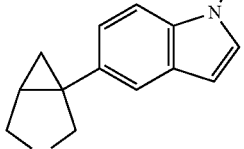

1-methyl-5-(3-methyl-3-aza-bicyclo[3.1.0]hexan-1-yl)-1H-indole

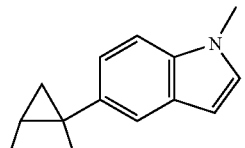

5-(3-ethyl-3-aza-bicyclo[3.1.0]hexan-1-yl)-1-methyl-1H-indole

TABLE 1-continued

Exemplary 1-Heteroaryl-3-azabicyclo[3.1.0]hexanes

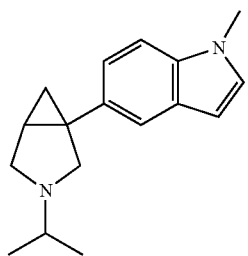 [SMILES: CC(C)N1CC2CC2(c2ccc3c(ccn3C)c2)C1]

5-(3-isopropyl-3-aza-
bicyclo[3.1.0]hexan-1-yl)-1-methyl-
1H-indole

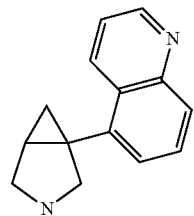

5-(3-aza-bicyclo[3.1.0]hexan-
1-yl)quinoline

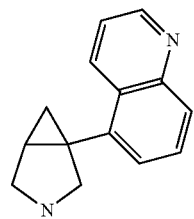

5-(3-methyl-3-aza-
bicyclo[3.1.0]hexan-1-yl)quinoline

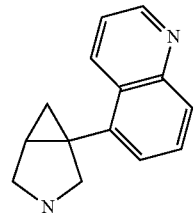

5-(3-ethyl-3-aza-bicyclo[3.1.0]hexan-
1-yl)quinoline

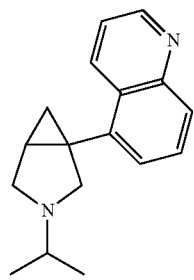 [SMILES: CC(C)N1CC2CC2(c2cccc3ncccc23)C1]

5-(3-isopropyl-3-aza-
bicyclo[3.1.0]hexan-1-yl)quinoline

TABLE 1-continued

Exemplary 1-Heteroaryl-3-azabicyclo[3.1.0]hexanes

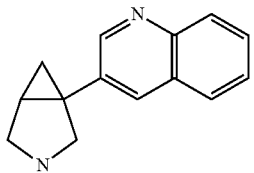

3-(3-aza-bicyclo[3.1.0]hexan-
1-yl)quinoline

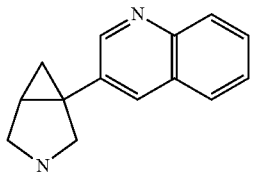

3-(3-methyl-3-aza-
bicyclo[3.1.0]hexan-1-yl)quinoline

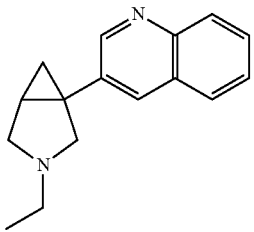 [SMILES: CCN1CC2CC2(c2cnc3ccccc3c2)C1]

3-(3-ethyl-3-aza-
bicyclo[3.1.0]hexan-1-yl)quinoline

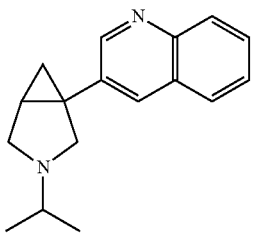 [SMILES: CC(C)N1CC2CC2(c2cnc3ccccc3c2)C1]

3-(3-isopropyl-3-aza-
bicyclo[3.1.0]hexan-1-yl)quinoline

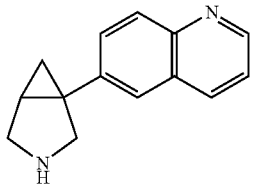 [SMILES: c1cnc2ccc(C34CNCC3C4)cc2c1]

6-(3-aza-bicyclo[3.1.0]hexan-1-
yl)quinoline

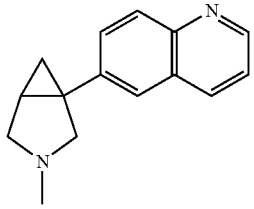 [SMILES: CN1CC2CC2(c2ccc3ncccc3c2)C1]

6-(3-methyl-3-aza-
bicyclo[3.1.0]hexan-1-yl)quinoline

TABLE 1-continued

Exemplary 1-Heteroaryl-3-azabicyclo[3.1.0]hexanes

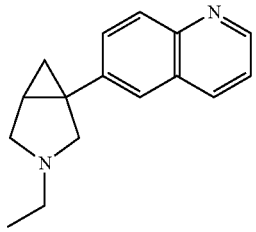 [SMILES: CCN1CC2CC2(c2ccc3ncccc3c2)C1]

6-(3-ethyl-3-aza-
bicyclo[3.1.0]hexan-1-yl)quinoline

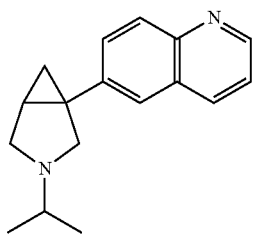 [SMILES: CC(C)N1CC2CC2(c2ccc3ncccc3c2)C1]

6-(3-isopropyl-3-aza-
bicyclo[3.1.0]hexan-1-yl)quinoline

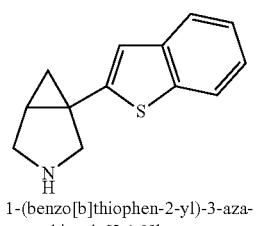

1-(benzo[b]thiophen-2-yl)-3-aza-
bicyclo[3.1.0]hexane

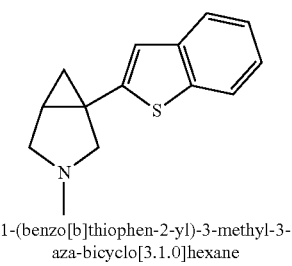

1-(benzo[b]thiophen-2-yl)-3-methyl-3-
aza-bicyclo[3.1.0]hexane

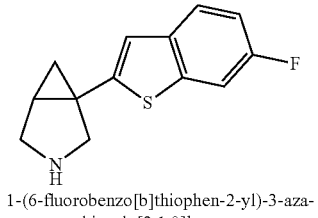

1-(6-fluorobenzo[b]thiophen-2-yl)-3-aza-
bicyclo[3.1.0]hexane

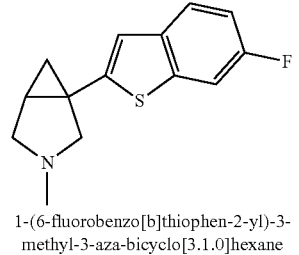

1-(6-fluorobenzo[b]thiophen-2-yl)-3-
methyl-3-aza-bicyclo[3.1.0]hexane

TABLE 1-continued

Exemplary 1-Heteroaryl-3-azabicyclo[3.1.0]hexanes

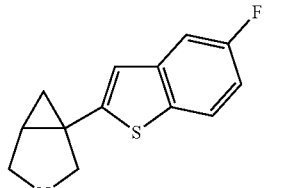

1-(5-fluorobenzo[b]thiophen-2-yl)-3-aza-
bicyclo[3.1.0]hexane

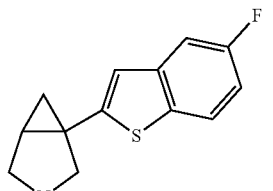

1-(5-fluorobenzo[b]thiophen-2-yl)-3-
methyl-3-aza-bicyclo[3.1.0]hexane

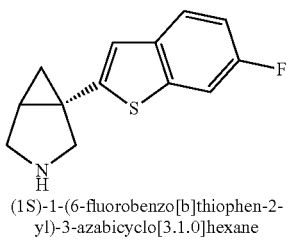

(1S)-1-(6-fluorobenzo[b]thiophen-2-
yl)-3-azabicyclo[3.1.0]hexane

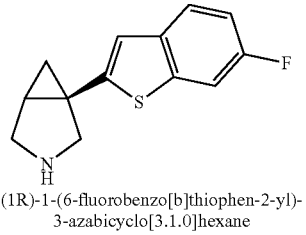

(1R)-1-(6-fluorobenzo[b]thiophen-2-yl)-
3-azabicyclo[3.1.0]hexane

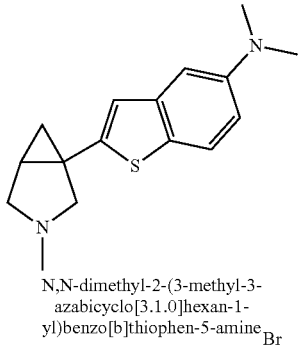

N,N-dimethyl-2-(3-methyl-3-
azabicyclo[3.1.0]hexan-1-
yl)benzo[b]thiophen-5-amine 1-(5-bromobenzo[b]thiophen-2-yl)-
3-azabicyclo[3.1.0]hexane

TABLE 1-continued

Exemplary 1-Heteroaryl-3-azabicyclo[3.1.0]hexanes

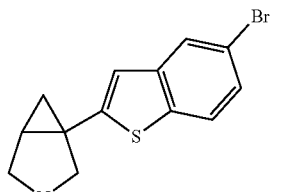

1-(5-bromobenzo[b]thiophen-2-yl)-3-
methyl-3-azabicyclo[3.1.0]hexane

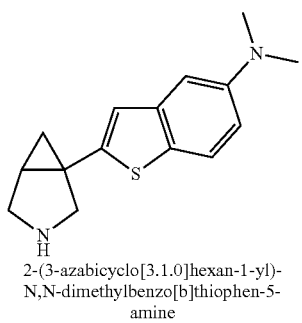

2-(3-azabicyclo[3.1.0]hexan-1-yl)-
N,N-dimethylbenzo[b]thiophen-5-
amine

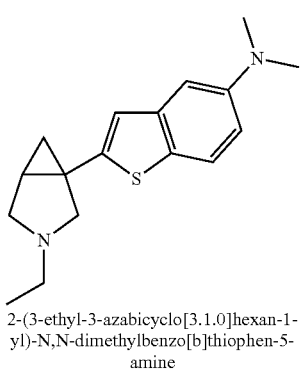

2-(3-ethyl-3-azabicyclo[3.1.0]hexan-1-
yl)-N,N-dimethylbenzo[b]thiophen-5-
amine

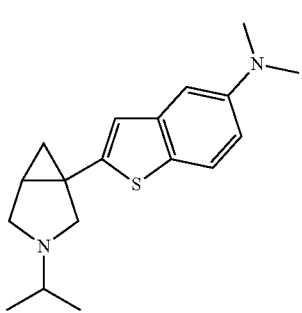 [SMILES: CC(C)N1CC2CC2(c2cc3cc(N(C)C)ccc3s2)C1]

2-(3-isopropyl-3-azabicyclo[3.1.0]hexan-
1-yl)-N,N-dimethylbenzo[b]thiophen-5-
amine

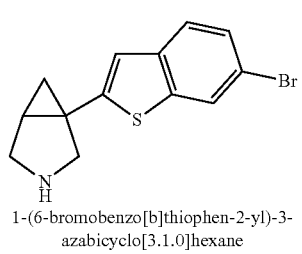

1-(6-bromobenzo[b]thiophen-2-yl)-3-
azabicyclo[3.1.0]hexane

TABLE 1-continued

Exemplary 1-Heteroaryl-3-azabicyclo[3.1.0]hexanes

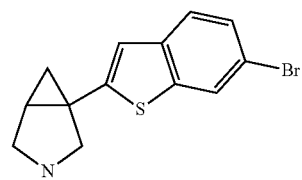

1-(6-bromobenzo[b]thiophen-2-yl)-3-methyl-
3-azabicyclo[3.1.0]hexane

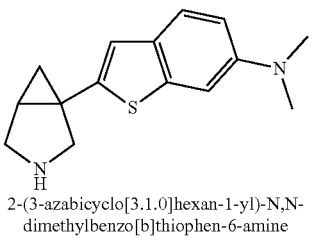

2-(3-azabicyclo[3.1.0]hexan-1-yl)-N,N-
dimethylbenzo[b]thiophen-6-amine

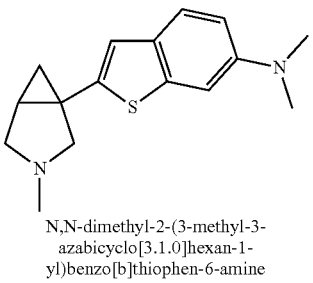

N,N-dimethyl-2-(3-methyl-3-
azabicyclo[3.1.0]hexan-1-
yl)benzo[b]thiophen-6-amine

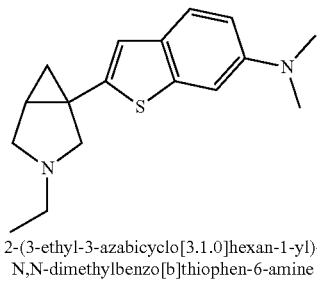

2-(3-ethyl-3-azabicyclo[3.1.0]hexan-1-yl)-
N,N-dimethylbenzo[b]thiophen-6-amine

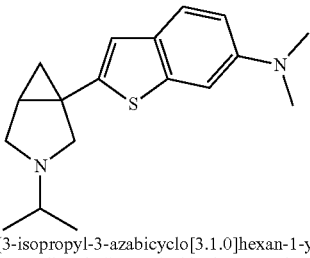

2-(3-isopropyl-3-azabicyclo[3.1.0]hexan-1-yl)-
N,N-dimethylbenzo[b]thiophen-6-amine The 1-heteroaryl-3-azabicyclo[3.1.0]hexanes of the invention are provided in any of a variety of forms, including pharmaceutically acceptable, active salts, solvates, hydrates, polymorphs, and/or prodrugs of the compounds disclosed herein, or any combination thereof.

It will be understood that the exemplary compounds identified in Table 1 are illustrative, and that the heteroaryl ring can be varied to comprise other substituents, and/or can include yet additional substituents (i.e., three or more substitutions on the heteroaryl ring), combined with one another, or additionally combined with or without substitutions on the nitrogen atom as described herein, to yield yet additional compounds within the invention for treating CNS disorders (including a range of neuropsychiatric disorders, such as depression and anxiety). For example, the invention provides an illustrative assemblage of novel 1-heteroaryl-3-azabicyclo [3.1.0]hexanes amines having multiple substitutions on the aryl ring, combined with or without substitution(s) on the nitrogen atom. Additionally, useful 1-heteroaryl-3-azabicyclo[3.1.0]hexanes of the invention include the substituted 1-heteroaryl-3-azabicyclo[3.1.0]hexanes compounds described herein, as well as their pharmaceutically acceptable salts, enantiomers, polymorphs, solvates, hydrate or prodrugs or combinations thereof.

Within related aspects of the invention, enantiomeric forms of the novel compounds described herein, having chiral symmetric structures, are provided, which provide yet additional drug candidates for treating CNS disorders. In certain embodiments, the invention provides enantiomers, diastereomers, and other stereoisomeric forms of the disclosed compounds, including racemic and resolved forms and mixtures thereof. The individual enantiomers may be separated according to methods that are well known to those of ordinary skill in the art. In other embodiments, the enantiomers, diastereomers and other stereoisomeric forms of the disclosed compounds contain no more than about 10%, about 5%, about 2% or about 1% of the corresponding enantiomers, diastereomers and stereoisomers. When the compounds described herein contain olefinic double bonds or other centers of geometric asymmetry, and unless specified otherwise, it is intended to include both E and Z geometric isomers. All tautomers are intended to be encompassed by the present invention as well.

As noted above, the compounds of the present invention can be can be prepared as both acid addition salts formed from an acid and the basic nitrogen group of 1-heteroaryl-3-azabicyclo[3.1.0.]hexanes and base salts. As further noted above, the methods of the present invention can be used to prepare compounds as both acid addition salts formed from an acid and the basic nitrogen group of 1-heteroaryl-3-azabicyclo [3.1.0.]hexanes and base salts. Suitable acid addition salts include, for example, hydrochloride, hydrobromide, hydroiodide, sulphate, hydrogen sulphate, nitrate, phosphate, and hydrogen phosphate salts. Other examples of pharmaceutically acceptable acid addition salts include inorganic and organic acid addition salts. Additional pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; organic acid salts such as acetate, citrate, lactate, succinate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate, tartrate, gluconate and the like. Suitable base salts are formed from bases, which form non-toxic salts and include, for example, aluminum, calcium, lithium, magnesium, potassium, sodium, zinc and diethanolamine salts. The hydrochloride salt formed with hydrochloric acid is an exemplary useful salt.

In other detailed embodiments, the invention provides prodrugs of the disclosed compounds. Prodrugs are considered to be any covalently bonded carriers which release the active parent drug in vivo. Examples of prodrugs include esters or amides of a compound of the present invention with hydroxyalkyl or aminoalkyl as a substituent. These may be prepared by reacting such compounds with anhydrides such as succinic anhydride.

The invention disclosed herein will also be understood to encompass in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein will also be understood to encompass the disclosed compounds isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

The compounds of the instant invention may be prepared using methods known to those skilled in the art, and in other embodiments by employing novel synthetic schemes as provided herein, which, along with the exemplified intermediate compounds, also fall within the scope of the invention. Accordingly, the present invention also provides novel methods and compositions for producing the compounds of the present invention as well as other 1-heteroaryl-3-azabicyclo [3.1.0]hexanes.

In certain embodiments, the present invention provides methods of making a 1-heteroaryl-3-azabicyclo[3.1.0]hexane of the following Formula III,

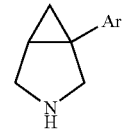

Formula III wherein Ar is a heterocyclic aryl group selected from furan, thiophene, pyrrole, imidazole, pyrazole, triazole, tetrazole, thiazole, isothiazole, pyridine, pyridizine, pyrimidine, pyrazine, triazine, indole, benzofuran, benzothiophene, benzothiazole, quinoline, isoquinoline, cinnoline, phthalazine, quinazoline, quinoxaline, chromane and isochromane, and Ar is either unsubstituted or substituted with one or more substituents independently selected from fluoro, chloro, bromo, iodo, —NO$_2$, —CN, —NH$_2$, carboxy, C$_{1-8}$ alkyl, C$_{2-8}$ alkenyl, C$_{2-8}$ alkynyl, halo(C$_{1-8}$)alkyl, hydroxy, trifluoromethyl, C$_{3-8}$ cycloalkyl, C$_{1-3}$ alkoxy, C$_{1-3}$ alkoxy(C$_{1-3}$)alkyl, carboxy (C$_{1-3}$)alkyl, C$_{1-3}$ alkanoyl, halo(C$_{1-3}$)alkoxyl, C$_{1-8}$ alkylamino, and di(C$_{1-8}$)alkylamino, comprising the steps of:

(a) reacting a compound of the following formula (i), Ar^CN, wherein Ar is defined as above, with epichlorhydrin or an enantiomer thereof, to produce a compound of the following formula (ii),

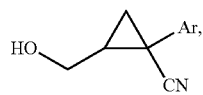

or an enantiomer or diastereomer thereof;

(b) reducing the compound of formula (ii) to produce a compound of the following formula (iii),

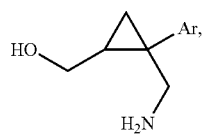

or an enantiomer or diastereomer thereof; and (c) causing cyclization of the compound of formula (iii) to produce the 1-heteroaryl-3-azabicyclo[3.1.0]hexane, or an enantiomer or diastereomer thereof.

In other embodiments, the present invention provides methods of making a 1-heteroaryl-3-azabicyclo[3.1.0]hexane of the following Formula I,

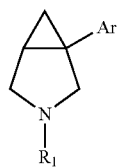

Formula I wherein Ar is a heterocyclic aryl group selected from furan, thiophene, pyrrole, imidazole, pyrazole, triazole, tetrazole, thiazole, isothiazole, pyridine, pyridizine, pyrimidine, pyrazine, triazine, indole, benzofuran, benzothiophene, benzothiazole, quinoline, isoquinoline, cinnoline, phthalazine, quinazoline, quinoxaline, chromane and isochromane, and Ar is either unsubstituted or substituted with one or more substituents independently selected from fluoro, chloro, bromo, iodo, —$NO_2$, —CN, —$NH_2$, carboxy, $C_{1-8}$ alkyl, $C_{2-8}$ alkenyl, $C_{2-8}$ alkynyl, halo($C_{1-8}$)alkyl, hydroxy, trifluoromethyl, $C_{3-8}$ cycloalkyl, $C_{1-3}$ alkoxy, $C_{1-3}$ alkoxy($C_{1-3}$)alkyl, carboxy($C_{1-3}$)alkyl, $C_{1-3}$ alkanoyl, halo($C_{1-3}$)alkoxyl, $C_{1-8}$ alkylamino, and di($C_{1-8}$)alkylamino and $R_1$ is selected from hydrogen, unsubstituted $C_{1-10}$ alkyl, $C_{3-8}$ cycloalkyl, $C_{2-10}$ alkenyl, and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy, comprising the steps of:

(a) reacting a compound of the following formula (iv),

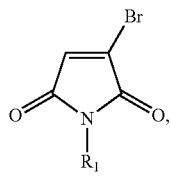

wherein $R_1$ is as defined above, with

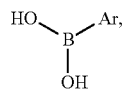

wherein Ar is as defined above, to produce a compound of the following formula (v),

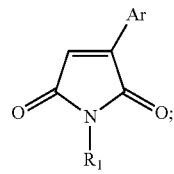

(b) causing cyclopropanation of the compound of formula (v) to produce a compound of the following formula (vi),

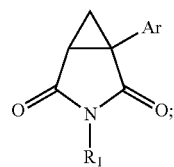

and (c) reducing the compound of formula (vi) to produce the 1-heteroaryl-3-azabicyclo[3.1.0]hexane.

In additional embodiments, the present invention provides methods of making a 1-heteroaryl-3-azabicyclo[3.1.0]hexane of the following Formula III,

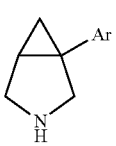

Formula III wherein Ar is a heterocyclic aryl group selected from furan, thiophene, pyrrole, imidazole, pyrazole, triazole, tetrazole, thiazole, isothiazole, pyridine, pyridizine, pyrimidine, pyrazine, triazine, indole, benzofuran, benzothiophene, benzothiazole, quinoline, isoquinoline, cinnoline, phthalazine, quinazoline, quinoxaline, chromane and isochromane, and Ar is either unsubstituted or substituted with one or more substituents independently selected from fluoro, chloro, bromo, iodo, —$NO_2$, —CN, —$NH_2$, carboxy, $C_{1-8}$ alkyl, $C_{2-8}$ alkenyl, $C_{2-8}$ alkynyl, halo($C_{1-8}$)alkyl, hydroxy, trifluoromethyl, $C_{3-8}$ cycloalkyl, $C_{1-3}$ alkoxy, $C_{1-3}$ alkoxy($C_{1-3}$)alkyl, carboxy($C_{1-3}$)alkyl, $C_{1-3}$ alkanoyl, halo($C_{1-3}$)alkoxyl, $C_{1-8}$ alkylamino, and di($C_{1-8}$)alkylamino, comprising the steps of:

(a) coupling a compound of the following formula (vii),

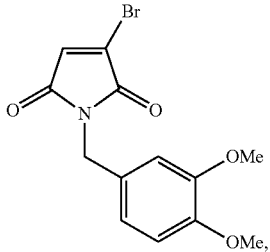

with

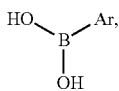

wherein Ar is as defined above, to produce a compound of the following formula (viii),

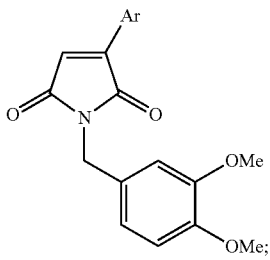

(b) causing cyclopropanation of the compound of formula (viii) to produce a compound of the following formula (ix),

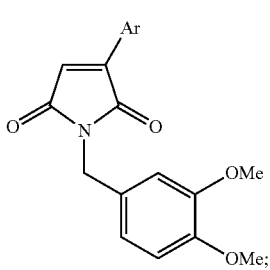

(c) reducing the compound of formula (ix) to produce a compound of the following formula (x),

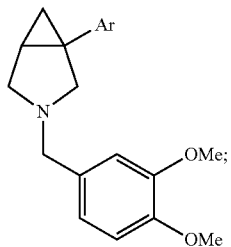

and (d) deprotecting the compound of formula (x) to produce the 1-heteroaryl-3-azabicyclo[3.1.0]hexane.

In practicing the methods of the present invention for making 1-heteroaryl-3-azabicyclo[3.1.0]hexanes, various reagents may be utilized for the different reaction steps. In general, suitable reagents for the various reaction steps may be selected by one of ordinary skill in the art based on the present disclosure.

Suitable reducing agents and methodologies include, for example, lithium aluminum hydride (LAH), sodium aluminum hydride (SAH), $NaBH_4$ with $ZnCl_2$ and catalytic hydrogenation.

Suitable nitrogen protecting groups include, for example, benzyl, allyl, tert-butyl and 3,4-dimethoxy-benzyl groups. In general, nitrogen protecting groups are well known to those skilled in the art, see for example, "Nitrogen Protecting Groups in Organic Synthesis", John Wiley and Sons, New York, N.Y., 1981, Chapter 7; "Nitrogen Protecting Groups in Organic Chemistry", Plenum Press, New York, N.Y., 1973, Chapter 2; T. W. Green and P. G. M. Wuts in "Protective Groups in Organic Chemistry", 3rd edition, John Wiley & Sons, New York, N.Y., 1999.

When the nitrogen protecting group is no longer needed, it may be removed by methods well known in the art. For example, benzyl or 3,4-dimethoxy-benzyl groups may be removed by catalytic hydrogenation. In general, methods of removing nitrogen protecting groups are well known to those skilled in the art, see for example, "Nitrogen Protecting Groups in Organic Synthesis", John Wiley and Sons, New York, N.Y., 1981, Chapter 7; "Nitrogen Protecting Groups in Organic Chemistry", Plenum Press, New York, N.Y., 1973, Chapter 2; T. W. Green and P. G. M. Wuts in "Protective Groups in Organic Chemistry", 3rd edition, John Wiley & Sons, Inc. New York, N.Y., 1999.

Suitable reagents for causing cyclization include, for example, $SOCl_2$, $POCl_3$, oxalyl chloride, phosphorous tribromide, triphenylphosphorous dibromide and oxalyl bromide.

Exemplary synthetic methods, starting materials, and intermediates useful in various aspects of the invention for producing novel compounds of the present invention are described below and in the examples.

Reaction Scheme 1 below generally sets forth an exemplary process for preparing 1-heteroaryl-3-azabicyclo[3.1.0]hexanes.

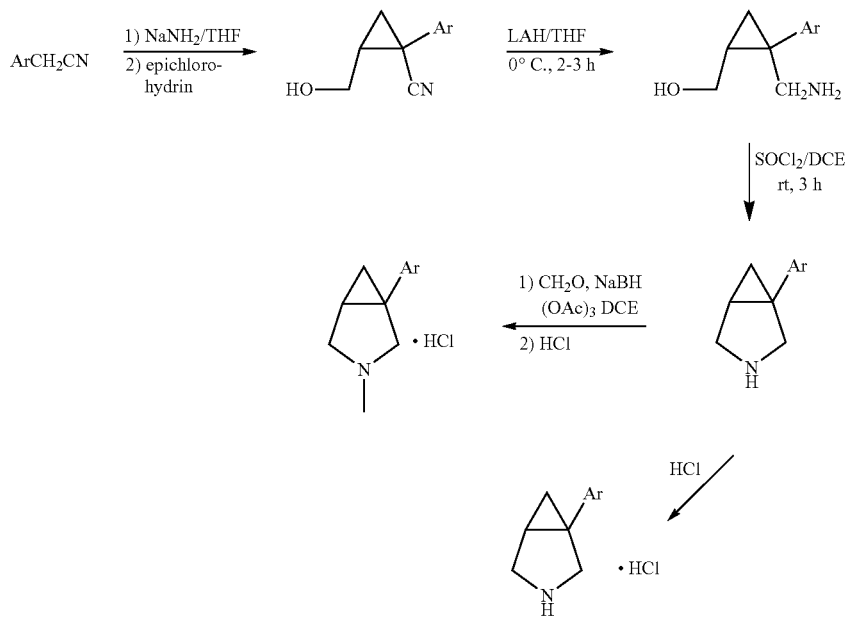

Ar = pyridinyl, thiophenyl, benzofuranyl, benzothiophenyl, benzothiazolyl, etc.

Reaction Scheme 2 below generally sets forth another exemplary process for preparing 1-heteroaryl-3-azabicyclo[3.1.0]hexanes.

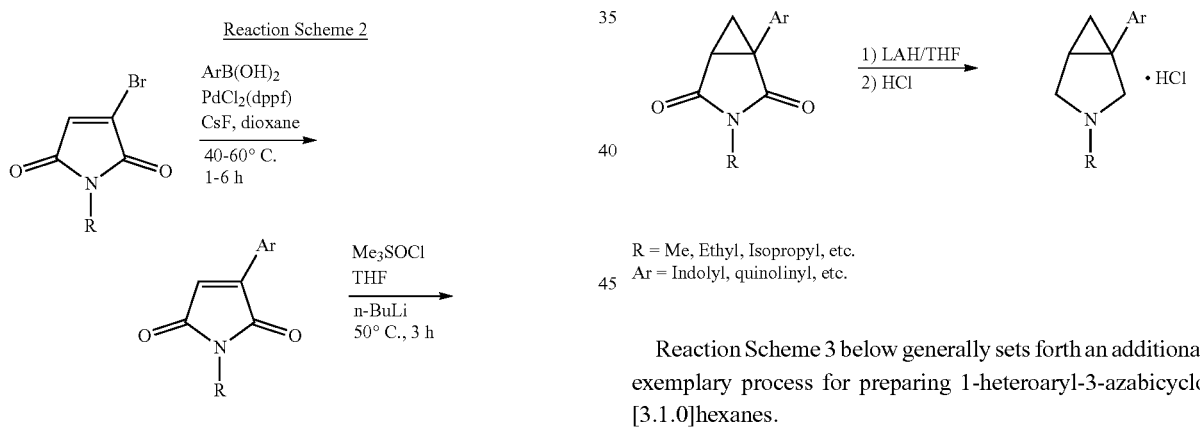

R = Me, Ethyl, Isopropyl, etc.
Ar = Indolyl, quinolinyl, etc.

Reaction Scheme 3 below generally sets forth an additional exemplary process for preparing 1-heteroaryl-3-azabicyclo[3.1.0]hexanes.

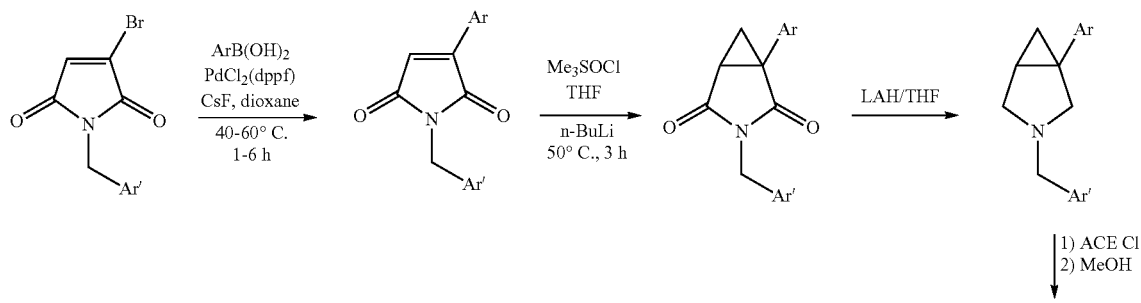

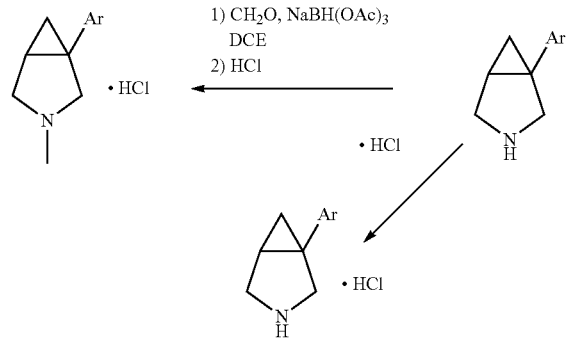

Ar' = 3,4-dimethoxyphenyl
Ar = benzothiphenyl, quinolinyl, etc.

Reaction Scheme 4 below generally sets forth an additional exemplary process for preparing chiral 1-heteroaryl-3-azabicyclo[3.1.0]hexanes.

Reaction Scheme 4

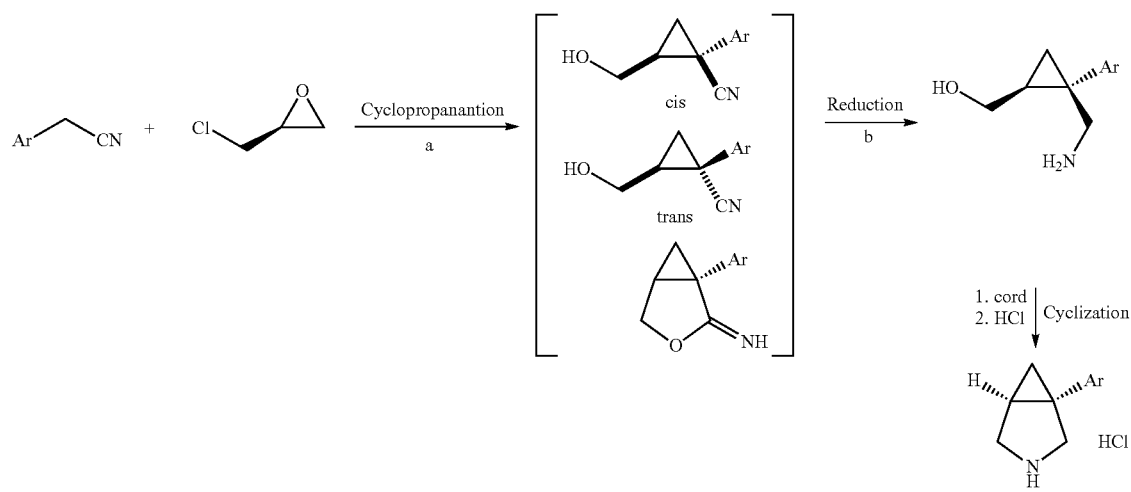

Ar = heterocycles
Reagents: (a) NaHMDS; (b) LAH or catalytic hydrogenation; (c) SOCl$_2$; (d) POCl$_3$ Reaction Scheme 5 below generally sets forth an additional exemplary process for preparing chiral 1-heteroaryl-3-azabicyclo[3.1.0]hexanes.

Reaction Scheme 5

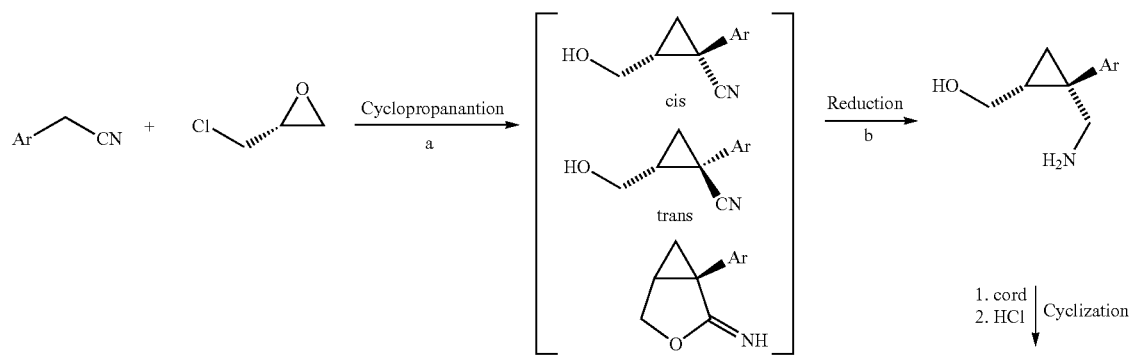

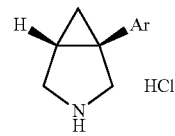

Ar = heterocycles
Reagents: (a) NaHMDS; (b) LAH or catalytic hydrogenation; (c) SOCl₂; (d) POCl₃

For the purposes of further describing the invention, including the novel compounds and synthetic methods disclosed herein, the following terms and definitions are provided by way of example.

The term "halogen" as used herein refers to bromine, chlorine, fluorine or iodine. In one embodiment, the halogen is chlorine. In another embodiment, the halogen is bromine.

The term "hydroxy" as used herein refers to —OH or —O⁻.

The term "alkyl" as used herein refers to straight- or branched-chain aliphatic groups containing 1-20 carbon atoms, preferably 1-7 carbon atoms and most preferably 1-4 carbon atoms. This definition applies as well to the alkyl portion of alkoxy, alkanoyl and aralkyl groups. In one embodiment, the alkyl is a methyl group.

The term "alkoxy" includes substituted and unsubstituted alkyl, alkenyl, and alkynyl groups covalently linked to an oxygen atom. In one embodiment, the alkoxy group contains 1 to 4 carbon atoms. Embodiments of alkoxy groups include, but are not limited to, methoxy, ethoxy, isopropyloxy, propoxy, butoxy, and pentoxy groups. Embodiments of substituted alkoxy groups include halogenated alkoxy groups. In a further embodiment, the alkoxy groups can be substituted with groups such as alkenyl, alkynyl, halogen, hydroxyl, alkylcarbonyloxy, phenylcarbonyloxy, alkoxycarbonyloxy, phenyloxycarbonyloxy, carboxylate, alkylcarbonyl, phenylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, phenylamino, diphenylamino, and alkylphenylamino), acylamino (including alkylcarbonylamino, phenylcarbonylamino, carbamoyl and ureido), amidino, imino, sulfhydryl, alkylthio, phenylthio, thiocarboxylate, sulfates, alkylsulfinyl, sulfonato, sulfamoyl, sulfonamido, nitro, trifluoromethyl, cyano, azido, heterocyclyl, alkylphenyl, or aromatic or heteroaromatic moieties. Exemplary halogen substituted alkoxy groups include, but are not limited to, fluoromethoxy, difluoromethoxy, trifluoromethoxy, chloromethoxy, dichloromethoxy, and trichloromethoxy.

The term "aryl" as used herein refers to monocyclic or bicyclic aromatic hydrocarbon groups having from 6 to 12 carbon atoms in the ring portion, for example, phenyl, naphthyl, biphenyl and diphenyl groups, each of which may be substituted with, for example, one to four substituents such as alkyl, substituted alkyl as defined above, halogen, trifluoromethyl, trifluoromethoxy, hydroxy, alkoxy, cycloalkyloxy, alkanoyl, alkanoyloxy, amino, alkylamino, dialkylamino, nitro, cyano, carboxy, carboxyalkyl, carbamyl, carbamoyl and aryloxy. Specific embodiments of aryl groups in accordance with the present invention include phenyl, substituted phenyl, naphthyl, biphenyl, and diphenyl.

The term "nitro", as used herein alone or in combination refers to a —NO₂ group.

The term "amino" as used herein refers to the group —NRR', where R and R' may independently be hydrogen, alkyl, phenyl, alkoxy, or heterophenyl. The term "aminoalkyl" as used herein represents a more detailed selection as compared to "amino" and refers to the group —NRR', where R and R' may independently be hydrogen or (C₁-C₄) alkyl.

The term "trifluoromethyl" as used herein refers to —CF₃.

The term "trifluoromethoxy" as used herein refers to —OCF₃.

The term "cycloalkyl" as used herein refers to a saturated cyclic hydrocarbon ring system containing from 3 to 7 carbon atoms that may be optionally substituted. Exemplary embodiments include, but are not limited to, cyclopropyl, cyclobutyl, cyclopentyl and cyclohexyl. In certain embodiments, the cycloalkyl group is cyclopropyl.

In another embodiment, the (cycloalkyl)alkyl groups contain from 3 to 7 carbon atoms in the cyclic portion and 1 to 4 carbon atoms in the alkyl portion. In certain embodiments, the (cycloalkyl)alkyl group is cyclopropylmethyl. The alkyl groups are optionally substituted with from one to three substituents selected from the group consisting of halogen, hydroxy and amino.

The terms "alkanoyl" and "alkanoyloxy" as used herein refer, respectively, to —C(O)-alkyl groups and —O—C(O)-alkyl groups, each optionally containing 2-5 carbon atoms. Specific embodiments of alkanoyl and alkanoyloxy groups are acetyl and acetoxy, respectively.

The term "aroyl," as used alone or in combination herein, refers to a phenyl radical derived from an aromatic carboxylic acid, such as optionally substituted benzoic or naphthoic acids.

The term "aralkyl" as used herein refers to a phenyl group bonded to an alkyl group, preferably one containing 1-4 carbon atoms. A preferred aralkyl group is benzyl.

The term "nitrile" or "cyano" as used herein refers to the group —CN.

The term "pyrrolidine-1-yl" as used herein refers to the structure:

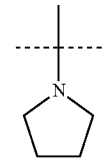

pyrrolidine-1-yl

The term "morpholino" as used herein refers to the structure:

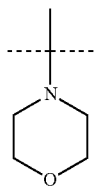

morpholino

The term "dialkylamino" refers to an amino group having two attached alkyl groups that can be the same or different.

The term "alkenyl" refers to a straight or branched alkenyl group of 2 to 10 carbon atoms having 1 to 3 double bonds. Preferred embodiments include ethenyl, 1-propenyl, 2-propenyl, 1-methylethenyl, 1-butenyl, 2-butenyl, 3-butenyl, 2-methyl-2-propenyl, 1-pentenyl, 2-pentenyl, 4-pentenyl, 3-methyl-2-butenyl, 1-hexenyl, 2-hexenyl, 1-heptenyl, 2-heptenyl, 1-octenyl, 2-octenyl, 1,3-octadienyl, 2-nonenyl, 1,3-nonadienyl, 2-decenyl, etc.

The term "alkynyl" as used herein refers to a straight or branched alkynyl group of 2 to 10 carbon atoms having 1 to 3 triple bonds. Exemplary alkynyls include, but are not limited to, ethynyl, 1-propynyl, 2-propynyl, 1-butynyl, 2-butynyl, 3-butynyl, 1-pentynyl, 2-pentynyl, 4-pentynyl, 1-octynyl, 6-methyl-1-heptynyl, and 2-decynyl.

The term "hydroxyalkyl" alone or in combination, refers to an alkyl group as previously defined, wherein one or several hydrogen atoms, preferably one hydrogen atom has been replaced by a hydroxyl group. Examples include hydroxymethyl, hydroxyethyl and 2-hydroxyethyl.

The term "aminoalkyl" and "alkylamino" as used herein refers to the group —NRR', where R and R' may independently be hydrogen or ($C_1$-$C_4$)alkyl.

The term "alkylaminoalkyl" refers to an alkylamino group linked via an alkyl group (i.e., a group having the general structure -alkyl-NH-alkyl or -alkyl-N(alkyl)(alkyl)). Such groups include, but are not limited to, mono- and di-($C_1$-$C_8$alkyl)amino$C_1$-$C_8$ alkyl, in which each alkyl may be the same or different.

The term "dialkylaminoalkyl" refers to alkylamino groups attached to an alkyl group. Examples include, but are not limited to, N,N-dimethylaminomethyl, N,N-dimethylaminoethyl, N,N-dimethylaminopropyl, and the like. The term dialkylaminoalkyl also includes groups where the bridging alkyl moiety is optionally substituted.

The term "haloalkyl" refers to an alkyl group substituted with one or more halo groups, for example chloromethyl, 2-bromoethyl, 3-iodopropyl, trifluoromethyl, perfluoropropyl, 8-chlorononyl and the like.

The term "carboxyalkyl" as used herein refers to the substituent —R'—COOH wherein R' is alkylene; and carbalkoxyalkyl refers to —R'—COOR wherein R' and R are alkylene and alkyl respectively. In certain embodiments, alkyl refers to a saturated straight- or branched-chain hydrocarbyl radical of 1-6 carbon atoms such as methyl, ethyl, n-propyl, isopropyl, n-butyl, t-butyl, n-pentyl, 2-methylpentyl, n-hexyl, and so forth. Alkylene is the same as alkyl except that the group is divalent.

The term "alkoxyalkyl" refers to an alkylene group substituted with an alkoxy group. For example, methoxyethyl [$CH_3OCH_2CH_2$—] and ethoxymethyl ($CH_3CH_2OCH_2$—] are both $C_3$ alkoxyalkyl groups.

The term "carboxy", as used herein, represents a group of the formula —COOH.

The term "alkanoylamino" refers to alkyl, alkenyl or alkynyl groups containing the group —C(O)— followed by —N(H)—, for example acetylamino, propanoylamino and butanoylamino and the like.

The term "carbonylamino" refers to the group —NR—CO—$CH_2$—R', where R and R' may be independently selected from hydrogen or ($C_1$-$C_4$)alkyl.

The term "carbamoyl" as used herein refers to —O—C(O)NH$_2$.

The term "carbamyl" as used herein refers to a functional group in which a nitrogen atom is directly bonded to a carbonyl, i.e., as in —NRC(=O)R' or —C(=O)NRR', wherein R and R' can be hydrogen, alkyl, substituted alkyl, alkenyl, substituted alkenyl, alkoxy, cycloalkyl, phenyl, heterocyclo, or heterophenyl.

The terms "heterocyclo" or "heterocyclic" refers to an optionally substituted, unsaturated, partially saturated, or fully saturated, aromatic or nonaromatic cyclic group that is a 4 to 7 membered monocyclic, or 7 to 11 membered bicyclic ring system that has at least one heteroatom in at least one carbon atom-containing ring. The substituents on the heterocyclo rings may be selected from those given above for the aryl groups. Each ring of the heterocyclo group containing a heteroatom may have 1, 2 or 3 heteroatoms selected from nitrogen atoms, oxygen atoms and sulfur atoms. Plural heteroatoms in a given heterocyclo ring may be the same or different.

The term "heteroaryl" refers to an optionally substituted monocyclic or bicyclic heterocyclic aryl group (ie., an aromatic heterocyclic group) that is a 4 to 7 membered monocyclic, or 7 to 11 membered bicyclic ring system that has at least one heteroatom in at least one carbon atom-containing ring. Each ring of the heteroaryl group containing a heteroatom may have 1, 2 or 3 heteroatoms selected from nitrogen atoms, oxygen atoms and sulfur atoms. Plural heteroatoms in a given heteroaryl group may be the same or different. Specific embodiments of heteroaryl groups in accordance with the present invention include furan, thiophene, pyrrole, imidazole, pyrazole, triazole, tetrazole, thiazole, isothiazole, pyridine, pyridizine, pyrimidine, pyrazine, triazine, indole, benzofuran, benzothiophene, benzothiazole, quinoline, isoquinoline, cinnoline, phthalazine, quinazoline, quinoxaline, chromane and isochromane groups.

The term "alkylsulfonylamino" refers to refers to the group —NHS(O)$_2$R$_a$ wherein R$_a$ is an alkyl as defined above.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

The compositions and methods of the instant invention comprising a 1-heteroaryl-3-azabicyclo[3.1.0]hexane are effective for treating or preventing a variety of central nervous system (CNS) disorders in mammals. In certain embodiments, pharmaceutical compositions and methods are provided for treating a CNS disorder in a mammalian subject. Mammalian subjects amenable for treatment using these compositions and methods include, but are not limited to, human and other mammalian subjects suffering from a CNS disorder that responds positively to intervention by inhibition of biogenic amine transport. In related embodiments, therapeutic compositions and methods are provided which employ an effective amount of one or more 1-heteroaryl-3-azabicyclo [3.1.0]hexane(s) described herein to treat or prevent a selected CNS disorder in a subject, wherein administration of the composition to the subject effectively inhibits the function of one or more, and in certain embodiments all three, norepinephrine, serotonin, and/or dopamine transport proteins in the subject, thereby preventing, or reducing the occurrence or severity of symptoms of, the targeted CNS disorder. Suitable forms of the compounds of the invention for use in biologically active compositions and methods of the invention include the compounds exemplified herein, as well as their pharmaceutically acceptable salts, polymorphs, solvates, hydrates and prodrugs.

In related embodiments, a biogenic amine transport inhibitory-effective amount of a 1-heteroaryl-3-azabicyclo[3.1.0.] hexane of the invention is administered to treat or prevent a CNS disorder, including neurological or psychiatric conditions, in a mammalian subject responsive to inhibition of biogenic amine transport. In more detailed aspects, administration of an active compound of the invention provides a therapeutic or prophylactic benefit by inhibiting or blocking reuptake of one or more, including any combination of two, or all three, biogenic amines selected from norepinephrine, serotonin, and dopamine.

Within more detailed treatment methods of the invention, administration of the active 1-heteroaryl-3-azabicyclo [3.1.0.]hexane(s) mediates a therapeutic effect via the active compound inhibiting reuptake of norepinephrine, serotonin, and/or dopamine. Biogenic amine reuptake inhibition in this context can optionally be determined and selected by using one or more 1-heteroaryl-3-azabicyclo[3.1.0.]hexane(s) of the invention to achieve variable selectivity and potency of transporter inhibition, wherein one or any combination of norepinephrine, serotonin and/or dopamine transporters can be inhibited, at pre-determined levels or ratios among or between different transporters. In this context, the various 1-heteroaryl-3-azabicyclo[3.1.0.]hexanes of the invention exhibit a wide range of potencies as inhibitors of one, two, or all three of the norepinephrine, serotonin and dopamine transporters-rendering them useful in a broad array of therapeutic applications.

In accordance with the invention, compounds disclosed herein, optionally formulated with additional ingredients in a pharmaceutically acceptable composition, are administered to mammalian subjects, for example a human patient, to treat or prevent one or more symptom(s) of a CNS disorder alleviated by inhibiting dopamine reuptake, and/or norepinephrine reuptake, and/or serotonin reuptake. In certain embodiments, "treatment" or "treating" refers to amelioration of one or more symptom(s) of a CNS disorder, whereby the symptom(s) is/are alleviated by inhibiting dopamine and/or norepinephrine and/or serotonin reuptake. In other embodiments, "treatment" or "treating" refers to an amelioration of at least one measurable physical parameter associated with a CNS disorder. In yet another embodiment, "treatment" or "treating" refers to inhibiting or reducing the progression or severity of a CNS disorder (or one or more symptom(s) thereof) alleviated by inhibiting dopamine and/or norepinephrine and/ or serotonin reuptake, e.g., as discerned based on physical, physiological, and/or psychological parameters. In additional embodiments, "treatment" or "treating" refers to delaying the onset of a CNS disorder (or one or more symptom(s) thereof) alleviated by inhibiting dopamine and/or norepinephrine and/ or serotonin reuptake.

In certain embodiments, a compound of the present invention or a pharmaceutically acceptable salt thereof is administered to a mammalian subject, for example a human patient, as a preventative or prophylactic treatment against a CNS disorder (or one or more symptom(s) thereof) alleviated by inhibiting dopamine and/or norepinephrine and/or serotonin reuptake. As used herein, "prevention", "preventing", and prophylaxis refers to a reduction in the risk or likelihood that the subject will acquire a CNS disorder or one or more symptom(s) thereof, which risk or likelihood is reduced in the subject by inhibiting dopamine and/or norepinephrine and/or serotonin reuptake. Alternatively, prevention and prophylaxis may correlate with a reduced risk of recurrence of the CNS disorder or symptom(s) thereof in the subject once the subject has been cured, restored to a normal state, or placed in remission from the subject CNS disorder. In related embodiments, a compound or pharmaceutical composition of the invention is administered as a preventative measure to the subject. Exemplary subjects amenable to prophylactic treatment in this context may have a genetic predisposition to a CNS disorder amenable to treatment by inhibiting dopamine, and/ or serotonin, and/or norepinephrine reuptake, such as a family history of a biochemical imbalance in the brain, or a non-genetic predisposition to a disorder alleviated by inhibiting dopamine and/or norepinephrine and/or serotonin reuptake.

A compound of the present invention and pharmaceutically acceptable salts thereof are useful for treating or preventing endogenous disorders alleviated by inhibiting dopamine and/ or norepinephrine and/or serotonin reuptake. Such disorders include, but are not limited to, attention-deficit disorder, depression, anxiety, obesity, Parkinson's disease, tic disorders, and addictive and substance abuse disorders.

Disorders alleviated by inhibiting dopamine and/or norepinephrine and/or serotonin reuptake are not limited to the specific disorders described herein, and the compositions and methods of the invention will be understood or readily ascertained to provide effective treatment agents for treating and/or preventing a wide range of additional CNS disorders and associated symptoms. For example, the compounds of the invention will provide promising candidates for treatment and/or prevention of attention deficit hyperactivity disorder and related symptoms, as well as forms and symptoms of alcohol abuse, drug abuse, cognitive distorders, obsessive compulsive behaviors, learning disorders, reading problems, gambling addiction, manic symptoms, phobias, panic attacks, oppositional defiant behavior, conduct disorder, academic problems in school, smoking, abnormal sexual behaviors, schizoid behaviors, somatization, depression, sleep disorders, general anxiety, stuttering, and tic disorders (See, for example, U.S. Pat. No. 6,132,724). Other disorders for which the compounds of the present invention may be useful include irritable bowel syndrome; inflammatory bowel disease; urinary tract disorders, such as stress urinary incontinence; PMDD (Premenstrual dysphoric disorder), degenerative diseases, including Alzheimers disease, and amyotrophic lateral sclerosis; and pyretic conditions (including fevers, and post and peri-menopausal hot flashes). These and other symptoms, regardless of the underlying CNS disorder, are each targets for the novel compositions and methods of the invention that mediate therapeutic benefits by inhibiting dopamine and/or norepinephrine and/or serotonin reuptake. Additional CNS disorders contemplated for treatment employing the compositions and methods of the invention are described, for example, in the Quick Reference to the Diagnostic Criteria From DSM-IV (Diagnostic and Statistical Manual of Mental Disorders, Fourth Edition), The American Psychiatric Association, Washington, D.C., 1994, 358 pages. Cognitive disorders for treatment and/or prevention according to the invention, include, but are not limited to, Attention-Deficit/Hyperactivity Disorder, Predominately Inattentive Type; Attention-Deficit/Hyperactivity Disorder, Predominately Hyperactivity-Impulsive Type; Attention-Deficit/Hyperactivity Disorder, Combined Type; Attention-Deficit/Hyperactivity Disorder not otherwise specified (NOS); Conduct Disorder; Oppositional Defiant Disorder; and Disruptive Behavior Disorder not otherwise specified (NOS).

Depressive disorders amenable for treatment and/or prevention according to the invention include, but are not limited to, Major Depressive Disorder, Recurrent; Dysthymic Disorder; Depressive Disorder not otherwise specified (NOS); and Major Depressive Disorder, Single Episode.

Addictive disorders amenable for treatment and/or prevention employing the methods and compositions of the invention include, but are not limited to, eating disorders, impulse control disorders, alcohol-related disorders, nicotine-related disorders, amphetamine-related disorders, *cannabis*-related disorders, cocaine-related disorders, hallucinogen use disorders, inhalant-related disorders, and opioid-related disorders, all of which are further sub-classified as listed below.

Eating disorders include, but are not limited to, Bulimia Nervosa, Nonpurging Type; Bulimia Nervosa, Purging Type; and Eating Disorder not otherwise specified (NOS).

Impulse control disorders include, but are not limited to, Intermittent Explosive Disorder, Kleptomania, Pyromania, Pathological Gambling, Trichotillomania, and Impulse Control Disorder not otherwise specified (NOS). Alcohol-related disorders include, but are not limited to, Alcohol-induced Psychotic Disorder, with delusions; Alcohol Abuse; Alcohol Intoxication; Alcohol Withdrawal; Alcohol Intoxication Delirium; Alcohol Withdrawal Delirium; Alcohol-Induced Persisting Dementia; Alcohol-Induced Persisting Amnestic Disorder; Alcohol Dependence; Alcohol-Induced Psychotic Disorder, with hallucinations; Alcohol-Induced Mood Disorder; Alcohol-Induced Anxiety Disorder; Alcohol-Induced Sexual Dysfunction; Alcohol-Induced Sleep Disorders; Alcohol-Related Disorders not otherwise specified (NOS); Alcohol Intoxication; and Alcohol Withdrawal.

Nicotine-related disorders include, but are not limited to, Nicotine Dependence, Nicotine Withdrawal, and Nicotine-Related Disorder not otherwise specified (NOS).

Amphetamine-related disorders include, but are not limited to, Amphetamine Dependence, Amphetamine Abuse, Amphetamine Intoxication, Amphetamine Withdrawal, Amphetamine Intoxication Delirium, Amphetamine-Induced Psychotic Disorder with delusions, Amphetamine-Induced Psychotic Disorders with hallucinations, Amphetamine-Induced Mood Disorder, Amphetamine-Induced Anxiety Disorder, Amphetamine-Induced Sexual Dysfunction, Amphetamine-Induced Sleep Disorder, Amphetamine Related Disorder not otherwise specified (NOS), Amphetamine Intoxication, and Amphetamine Withdrawal.

*Cannabis*-related disorders include, but are not limited to, *Cannabis* Dependence; *Cannabis* Abuse; *Cannabis* Intoxication; *Cannabis* Intoxication Delirium; *Cannabis*-Induced Psychotic Disorder, with delusions; *Cannabis*-Induced Psychotic Disorder with hallucinations; *Cannabis*-Induced Anxiety Disorder; *Cannabis* Related Disorder not otherwise specified (NOS); and *Cannabis* Intoxication.

Cocaine-related disorders include, but are not limited to, Cocaine Dependence, Cocaine Abuse, Cocaine Intoxication, Cocaine Withdrawal, Cocaine Intoxication Delirium, Cocaine-Induced Psychotic Disorder with delusions, Cocaine-Induced Psychotic Disorders with hallucinations, Cocaine-Induced Mood Disorder, Cocaine-Induced Anxiety Disorder, Cocaine-Induced Sexual Dysfunction, Cocaine-Induced Sleep Disorder, Cocaine Related Disorder not otherwise specified (NOS), Cocaine Intoxication, and Cocaine Withdrawal.

Hallucinogen-use disorders include, but are not limited to, Hallucinogen Dependence, Hallucinogen Abuse, Hallucinogen Intoxication, Hallucinogen Withdrawal, Hallucinogen Intoxication Delirium, Hallucinogen-Induced Psychotic Disorder with delusions, Hallucinogen-Induced Psychotic Disorders with hallucinations, Hallucinogen-Induced Mood Disorder, Hallucinogen-Induced Anxiety Disorder, Hallucinogen-Induced Sexual Dysfunction, Hallucinogen-Induced Sleep Disorder, Hallucinogen Related Disorder not otherwise specified (NOS), Hallucinogen Intoxication, and Hallucinogen Persisting Perception Disorder (Flashbacks).

Inhalant-related disorders include, but are not limited to, Inhalant Dependence; Inhalant Abuse; Inhalant Intoxication; Inhalant Intoxication Delirium; Inhalant-Induced Psychotic Disorder, with delusions; Inhalant-Induced Psychotic Disorder with hallucinations; Inhalant-Induced Anxiety Disorder; Inhalant Related Disorder not otherwise specified (NOS); and Inhalant Intoxication.

Opioid-related disorders include, but are not limited to, Opioid Dependence, Opioid Abuse, Opioid Intoxication, Opioid Intoxication Delirium, Opioid-Induced Psychotic Disorder, with delusions, Opioid-Induced Psychotic Disorder with hallucinations, Opioid-Induced Anxiety Disorder, Opioid Related Disorder not otherwise specified (NOS), Opioid Intoxication, and Opioid Withdrawal.

Tic disorders include, but are not limited to, Tourette's Disorder, Chronic Motor or Vocal Tic Disorder, Transient Tic Disorder, Tic Disorder not otherwise specified (NOS), Stuttering, Autistic Disorder, and Somatization Disorder.

By virtue of their multiple reuptake inhibitory activity, the novel compounds of the present invention are thus useful in a wide range of veterinary and human medical applications, in particular for treating and/or preventing a wide array of CNS disorders and/or associated symptom(s) alleviated by by inhibiting dopamine and/or norepinephrine and/or serotonin reuptake.

Within additional aspects of the invention, combinatorial formulations and coordinate administration methods are provided which employ an effective amount of a compound of the invention (or a pharmaceutically effective enantiomer, salt, solvate, hydrate, polymorph, or prodrug thereof), and one or more additional active agent(s) that is/are combinatorially formulated or coordinately administered with the compound of the invention—yielding a combinatorial formulation or coordinate administration method that is effective to modulate, alleviate, treat or prevent a targeted CNS disorder, or one or more symptom(s) thereof, in a mammalian subject.

Exemplary combinatorial formulations and coordinate treatment methods in this context comprise a therapeutic compound of the invention in combination with one or more additional or adjunctive treatment agents or methods for treating the targeted CNS disorder or symptom(s), for example one or more antidepressant or anxiolytic agent(s) and/or therapeutic method(s).

In related embodiments of the invention, the compounds disclosed herein can be used in combination therapy with at least one other therapeutic agent or method. In this context, compounds of the invention can be administered concurrently or sequentially with administration of a second therapeutic agent, for example a second agent that acts to treat or prevent the same, or different, CNS disorder or symptom(s) for which the compound of the invention is administered. The compound of the invention and the second therapeutic agent can be combined in a single composition or adminstered in different compositions. The second therapeutic agent may also be effective for treating and/or preventing a CNS disorder or associated symptom(s) by inhibiting dopamine and/or norepinephrine and/or serotonin reuptake. The coordinate administration may be done simultaneously or sequentially in either order, and there may be a time period while only one or both (or all) active therapeutic agents, individually and/or collectively, exert their biological activities and therapeutic effects. A distinguishing aspect of all such coordinate treatment methods is that the compound of the invention exerts at least some detectable therapeutic activity toward alleviating or preventing the targeted CNS disorder or symptom(s), as described herein, and/or elicit a favorable clinical response, which may or may not be in conjunction with a secondary clinical response provided by the secondary therapeutic agent. Often, the coordinate administration of a compound of the invention with a secondary therapeutic agent as contemplated herein will yield an enhanced therapeutic response beyond the therapeutic response elicited by either or both the compound of the invention and/or secondary therapeutic agent alone.

As many of the CNS disorders and symptoms treatable or preventable using compounds of the present invention are chronic, in one embodiment combination therapy involves alternating between administering a compound of the present invention and a second therapeutic agent (i.e., alternating therapy regimens between the two drugs, e.g., at one week, one month, three month, six month, or one year intervals). Alternating drug regimens in this context will often reduce or even eliminate adverse side effects, such as toxicity, that may attend long-term administration of one or both drugs alone.

In certain embodiments of combinatorial formulations and coordinate treatment methods of the invention, the secondary therapeutic is a norepinephrine reuptake inhibitor. Examples of norepinephrine reuptake inhibitors useful in this context include tertiary amine tricyclics such as amitriptyline, clomipramine, doxepin, imipramine, (+)-trimipramine, and secondary amine tricyclics including amoxapine, atomoxetine, desipramine, maprotiline, nortriptyline, and protriptyline.

In certain embodiments of combinatorial formulations and coordinate treatment methods of the invention, the secondary therapeutic is a serotonin reuptake inhibitor. Examples of other serotonin reuptake inhibitors useful in this context include citalopram, fluoxetine, fluvoxamine, (−)-paroxetine, sertraline, and venlafaxine.

In other embodiments of combinatorial formulations and coordinate treatment methods provided herein, the secondary therapeutic agent is an anti-attention-deficit-disorder treatment agent. Examples of useful anti-attention-deficit-disorder agents for use in these embodiments include, but are not limited to, methylphenidate; dextroamphetamine; tricyclic antidepressants, such as imipramine, desipramine, and nortriptyline; and psychostimulants, such as pemoline and deanol.

In additional embodiments of combinatorial formulations and coordinate treatment methods provided herein, the secondary therapeutic agent is an anti-addictive-disorder agent. Examples of useful anti-addictive-disorder agents include, but are not limited to, tricyclic antidepressants; glutamate antagonists, such as ketamine HCl, dextromethorphan, dextrorphan tartrate and dizocilpine (MK801); degrading enzymes, such as anesthetics and aspartate antagonists; GABA agonists, such as baclofen and muscimol HBr; reuptake blockers; degrading enzyme blockers; glutamate agonists, such as D-cycloserine, carboxyphenylglycine, L-glutamic acid, and cis-piperidine-2,3-dicarboxylic acid; aspartate agonists; GABA antagonists such as gabazine (SR-95531), saclofen, bicuculline, picrotoxin, and (+) apomorphine HCl; and dopamine antagonists, such as spiperone HCl, haloperidol, and (−) sulpiride.

In other embodiments of combinatorial formulations and coordinate treatment methods provided herein, the secondary therapeutic agent is an anti-alcohol agent. Examples of useful anti-alcohol agents include, but are not limited to, disulfiram and naltrexone.

In other embodiments of combinatorial formulations and coordinate treatment methods provided herein, the secondary therapeutic agent is an anti-nicotine agent. Examples of useful anti-nicotine agents include, but are not limited to, clonidine.

In other embodiments of combinatorial formulations and coordinate treatment methods provided herein, the secondary therapeutic agent is an anti-opiate agent. Examples of useful anti-opiate agents include, but are not limited to, methadone, clonidine, lofexidine, levomethadyl acetate HCl, naltrexone, and buprenorphine.

In other embodiments of combinatorial formulations and coordinate treatment methods provided herein, the secondary therapeutic agent is anti-cocaine agent. Examples of useful anti-cocaine agents include, but are not limited to, desipramine, amantadine, fluoxidine, and buprenorphine.

In other embodiments of combinatorial formulations and coordinate treatment methods provided herein, the secondary therapeutic agent is an anti-lysergic acid diethylamide ("anti-LSD") agent. Examples of useful anti-LSD agents include, but are not limited to, diazepam.

In other embodiments of combinatorial formulations and coordinate treatment methods provided herein, the secondary therapeutic agent is an anti-phencyclidine ("anti-PCP") agent. Examples of useful anti-PCP agents include, but are not limited to, haloperidol.

In other embodiments of combinatorial formulations and coordinate treatment methods provided herein, the secondary therapeutic agent is an appetite suppressant. Examples of useful appetite suppressants include, but are not limited to, fenfluramine, phenylpropanolamine, and mazindol.

In yet additional embodiments of combinatorial formulations and coordinate treatment methods provided herein, the secondary therapeutic agent is an anti-Parkinson's-disease agent. Examples of useful anti-Parkinson's-disease agents include, but are not limited to dopamine precursors, such as levodopa, L-phenylalanine, and L-tyrosine; neuroprotective agents; dopamine agonists; dopamine reuptake inhibitors; anticholinergics such as amantadine and memantine; and 1,3,5-trisubstituted adamantanes, such as 1-amino-3,5-dimethyl-adamantane. (See, U.S. Pat. No. 4,122,193)

Administration of an effective amount of a 1-heteroaryl-3-azabicyclo[3.1.0.]hexane of the invention to a mammalian subject presenting with one or more symptoms of a CNS disorder or other neurological or psychiatric condition will detectably decrease, eliminate, or prevent the targeted CNS disorder and/or associated symptom(s). In exemplary embodiments, administration of a 1-heteroaryl-3-azabicyclo [3.1.0.]hexane composition to a suitable test subject will yield a reduction in one or more target symptom(s) associated with a selected CNS disorder, such as pain, by at least 10%, 20%, 30%, 50% or greater, up to a 75-90%, or 95% or greater, reduction in the targeted CNS disorder or one or more target symptom(s), compared to placebo-treated or other suitable control subjects. Comparable levels of efficacy are contemplated for the entire range of CNS disorders, including all contemplated neurological and psychiatric disorders, and related conditions and symptoms, for treatment or prevention using the compositions and methods of the invention.

The active compounds of the invention may be optionally formulated with a pharmaceutically acceptable carrier and/or various excipients, vehicles, stabilizers, buffers, preservatives, etc. An "effective amount," "therapeutic amount," "therapeutically effective amount," or "effective dose" is an effective amount or dose of an active compound as described herein sufficient to elicit a desired pharmacological or therapeutic effect in a mammalian subject-typically resulting in a measurable reduction in an occurrence, frequency, or severity of one or more symptom(s) of a CNS disorder, including any combination of neurological and/or psychological symptoms, diseases, or conditions, associated with or caused by the targeted CNS disorder, in the subject. In certain embodiments, when a compound of the invention is administered to treat a CNS disorder, for example a pain disorder, an effective amount of the compound will be an amount sufficient in vivo to delay or eliminate onset of symptoms of the targeted condition or disorder. Therapeutic efficacy can alternatively be demonstrated by a decrease in the frequency or severity of symptoms associated with the treated condition or disorder, or by altering the nature, recurrence, or duration of symptoms associated with the treated condition or disorder. Therapeutically effective amounts, and dosage regimens, of the 1-heteroaryl-3-azabicyclo[3.1.0.]hexane compositions of the invention, including pharmaceutically effective salts, solvates, hydrates, polymorphs or prodrugs thereof, will be readily determinable by those of ordinary skill in the art, often based on routine clinical or patient-specific factors.

Suitable routes of administration for a 1-heteroaryl-3-azabicyclo[3.1.0.]hexane of the invention include, but are not limited to, oral, buccal, nasal, aerosol, topical, transdermal, mucosal, injectable, slow release, controlled release, iontophoresis, sonophoresis, and other conventional delivery routes, devices and methods. Injectable delivery methods are also contemplated, including but not limited to, intravenous, intramuscular, intraperitoneal, intraspinal, intrathecal, intracerebroventricular, intraarterial, and subcutaneous injection.

Suitable effective unit dosage amounts of a 1-heteroaryl-3-azabicyclo[3.1.0.]hexane of the invention for mammalian subjects may range from about 25 to 1800 mg, 50 to 1000 mg, 75 to 900 mg, 100 to 750 mg, or 150 to 500 mg. In certain embodiments, the effective dosage will be selected within narrower ranges of, for example, 10 to 25 mg, 30-50 mg, 75 to 100 mg, 100 to 250 mg, or 250 to 500 mg. These and other effective unit dosage amounts may be administered in a single dose, or in the form of multiple daily, weekly or monthly doses, for example in a dosing regimen comprising from 1 to 5, or 2-3, doses administered per day, per week, or per month. In exemplary embodiments, dosages of 10 to 25 mg, 30-50 mg, 75 to 100 m& 100 to 250 mg, or 250 to 500 mg, are administered one, two, three, or four times per day. In more detailed embodiments, dosages of 50-75 mg, 100-200 mg, 250-400 mg, or 400-600 mg are administered once or twice daily. In alternate embodiments, dosages are calculated based on body weight, and may be administered, for example, in amounts from about 0.5 mg/kg to about 20 mg/kg per day, 1 mg/kg to about 15 mg/kg per day, 1 mg/kg to about 10 mg/kg per day, 2 mg/kg to about 20 mg/kg per day, 2 mg/kg to about 10 mg/kg per day or 3 mg/kg to about 15 mg/kg per day.

The amount, timing and mode of delivery of compositions of the invention comprising an effective amount of a 1-heteroaryl-3-azabicyclo[3.1.0.]hexane of the invention will be routinely adjusted on an individual basis, depending on such factors as weight, age, gender, and condition of the individual, the acuteness of the condition to be treated and/or related symptoms, whether the administration is prophylactic or therapeutic, and on the basis of other factors known to effect drug delivery, absorption, pharmacokinetics, including half-life, and efficacy. An effective dose or multi-dose treatment regimen for the compounds of the invention will ordinarily be selected to approximate a minimal dosing regimen that is necessary and sufficient to substantially prevent or alleviate one or more symptom(s) of a neurological or psychiatric condition in the subject, as described herein. Thus, following administration of a 1-heteroaryl-3-azabicyclo[3.1.0.]hexane of the invention according to the formulations and methods herein, test subjects will exhibit a 10%, 20%, 30%, 50% or greater reduction, up to a 75-90%, or 95% or greater, reduction, in one or more symptoms associated with a targeted CNS disorder or other neurological or psychiatric condition, compared to placebo-treated or other suitable control subjects.

Pharmaceutical dosage forms of the 1-heteroaryl-3-azabicyclo[3.1.0.]hexanes of the present invention may optionally include excipients recognized in the art of pharmaceutical compounding as being suitable for the preparation of dosage units as discussed above. Such excipients include, without limitation, binders, fillers, lubricants, emulsifiers, suspending agents, sweeteners, flavorings, preservatives, buffers, wetting agents, disintegrants, effervescent agents and other conventional excipients and additives.

The compositions of the invention for treating CNS disorders, including depression, anxiety, and/or pain, can thus include any one or combination of the following: a pharmaceutically acceptable carrier or excipient; other medicinal agent(s); pharmaceutical agent(s); adjuvants; buffers; preservatives; diluents; and various other pharmaceutical additives and agents known to those skilled in the art. These additional formulation additives and agents will often be biologically inactive and can be administered to patients without causing unacceptable deleterious side effects or serious adverse interactions with the active agent.

If desired, the substituted 1-heteroaryl-3-azabicyclo[3.1.0.]hexanes of the invention can be administered in a controlled release form, for example by use of a slow release carrier such as a hydrophilic, slow release polymer. Exemplary controlled release agents in this context include, but are not limited to, hydroxypropyl methyl cellulose, having a viscosity in the range of about 100 cps to about 100,000 cps.

1-heteroaryl-3-azabicyclo[3.1.0.]hexane compositions of the invention will often be formulated and administered in an oral dosage form, optionally in combination with a carrier or other additive(s). Suitable carriers common to pharmaceutical formulation technology include, but are not limited to, microcrystalline cellulose, lactose, sucrose, fructose, glucose, dextrose, or other sugars, di-basic calcium phosphate, calcium sulfate, cellulose, methylcellulose, cellulose derivatives, kaolin, mannitol, lactitol, maltitol, xylitol, sorbitol, or other sugar alcohols, dry starch, dextrin, maltodextrin or other polysaccharides, inositol, or mixtures thereof. Exemplary unit oral dosage forms for use in this invention include tablets, which may be prepared by any conventional method of preparing pharmaceutical oral unit dosage form. Oral unit dosage forms, such as tablets, may contain one or more conventional additional formulation ingredients, including, but not limited to, release modifying agents, glidants, compression aides, disintegrants, lubricants, binders, flavors, flavor enhancers, sweeteners and/or preservatives.

Suitable lubricants include stearic acid, magnesium stearate, talc, calcium stearate, hydrogenated vegetable oils, sodium benzoate, leucine carbowax, magnesium lauryl sulfate, colloidal silicon dioxide and glyceryl monostearate. Suitable glidants include colloidal silica, fumed silicon dioxide, silica, talc, fumed silica, gypsum and glyceryl monostearate. Substances which may be used for coating include hydroxypropyl cellulose, titanium oxide, talc, sweeteners and colorants. The aforementioned effervescent agents and disintegrants are useful in the formulation of rapidly disintegrating tablets known to those skilled in the art. These typically disintegrate in the mouth in less than one minute, and preferably in less than thirty seconds. By effervescent agent is meant a couple, typically an organic acid and a carbonate or bicarbonate. Such rapidly acting dosage forms would be useful, for example, in the prevention or treatment of acute attacks of panic disorder.

Additional 1-heteroaryl-3-azabicyclo[3.1.0.]hexane compositions of the invention can be prepared and administered in any of a variety of inhalation or nasal delivery forms known in the art. Devices capable of depositing aerosolized substituted 1-heteroaryl-3-azabicyclo[3.1.0.]hexane formulations in the sinus cavity or pulmonary alveoli of a patient include metered dose inhalers, nebulizers, dry powder generators, sprayers, and the like. Pulmonary delivery to the lungs for rapid transit across the alveolar epithelium into the blood stream may be particularly useful in treating impending episodes of seizures or panic disorder. Methods and compositions suitable for pulmonary delivery of drugs for systemic effect are well known in the art. Suitable formulations, wherein the carrier is a liquid, for administration, as for example, a nasal spray or as nasal drops, may include aqueous or oily solutions of a 1-heteroaryl-3-azabicyclo[3.1.0.]hexane, and any additional active or inactive ingredient(s).

Intranasal and pulmonary delivery permits the passage of active compounds of the invention into the blood stream directly after administering an effective amount of the compound to the nose or lung. In the case of intranasal delivery, this mode of administration can achieve direct, or enhanced, delivery of the active compound to the CNS. For intranasal and pulmonary administration, a liquid aerosol formulation will often contain an active compound of the invention combined with a dispersing agent and/or a physiologically acceptable diluent. Alternatively, dry powder aerosol formulations may contain a finely divided solid form of the subject compound and a dispersing agent allowing for the ready dispersal of the dry powder particles. With either liquid or dry powder aerosol formulations, the formulation must be aerosolized into small, liquid or solid particles in order to ensure that the aerosolized dose reaches the mucous membranes of the nasal passages or the lung. The term "aerosol particle" is used herein to describe a suitable liquid or solid particle of a sufficiently small particle diameter, e.g., in a range of from about 2-5 microns, for nasal or pulmonary distribution to targeted mucous or alveolar membranes. Other considerations include the construction of the delivery device, additional components in the formulation, and particle characteristics. These aspects of nasal or pulmonary administration of drugs are well known in the art, and manipulation of formulations, aerosolization means, and construction of delivery devices, is within the level of ordinary skill in the art.

Yet additional compositions and methods of the invention are provided for topical administration of 1-heteroaryl-3-azabicyclo[3.1.0.]hexanes for treating CNS disorders, including pain. Topical compositions may comprise a 1-heteroaryl-3-azabicyclo[3.1.0.]hexane and any other active or inactive component(s) incorporated in a dermatological or mucosal acceptable carrier, including in the form of aerosol sprays, powders, dermal patches, sticks, granules, creams, pastes, gels, lotions, syrups, ointments, impregnated sponges, cotton applicators, or as a solution or suspension in an aqueous liquid, non-aqueous liquid, oil-in-water emulsion, or water-in-oil liquid emulsion. These topical compositions may comprise a 1-heteroaryl-3-azabicyclo[3.1.0.]hexane dissolved or dispersed in a portion of a water or other solvent or liquid to be incorporated in the topical composition or delivery device. Transdermal administration may be enhanced by the use of dermal penetration enhancers known to those skilled in the art.

Yet additional 1-heteroaryl-3-azabicyclo[3.1.0.]hexane formulations are provided for parenteral administration, including aqueous and non-aqueous sterile injection solutions which may optionally contain anti-oxidants, buffers, bacteriostats and/or solutes which render the formulation isotonic with the blood of the mammalian subject; and aqueous and non-aqueous sterile suspensions which may include suspending agents and/or thickening agents. The formulations may be presented in unit-dose or multi-dose containers.

1-heteroaryl-3-azabicyclo[3.1.0.]hexane formulations of the invention may also include polymers for extended release following parenteral administration. Extemporaneous injection solutions, emulsions and suspensions may be prepared from sterile powders, granules and tablets of the kind previously described. Preferred unit dosage formulations are those containing a daily dose or unit, daily sub-dose, as described herein above, or an appropriate fraction thereof, of the active ingredient(s).

In more detailed embodiments, 1-heteroaryl-3-azabicyclo[3.1.0.]hexanes may be encapsulated for delivery in microcapsules, microparticles, or microspheres, prepared, for example, by coacervation techniques or by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nanoparticles and nanocapsules) or in macroemulsions.

The invention also provides pharmaceutical packs or kits comprising one or more containers holding a 1-heteroaryl-3-azabicyclo[3.1.0.]hexane, or any composition comprising a 1-heteroaryl-3-azabicyclo[3.1.0.]hexane as described herein, including pharmaceutically acceptable salts and other forms of 1-heteroaryl-3-azabicyclo[3.1.0.]hexanes as described, in a pharmaceutically acceptable, stable form. Optionally packaged with these packs and kits can be a notice, e.g., in a form prescribed by a governmental agency regulating pharmaceuticals or biological products, reflecting approval by the agency of the manufacture, use and/or sale of the product contained in the pack or kit for human administration (optionally specifying one or more approved treatment indications as described herein).

The pharmaceutical agents of the invention may be administered parenterally, e.g. intravenously, intramuscularly, subcutaneously or intraperitoneally. The parenteral preparations may be solutions, dispersions or emulsions suitable for such administration. The subject agents may also be formulated into polymers for extended release following parenteral administration. Pharmaceutically acceptable formulations and ingredients will typically be sterile or readily sterilizable, biologically inert, and easily administered. Such polymeric materials are well known to those of ordinary skill in the pharmaceutical compounding arts. Parenteral preparations typically contain buffering agents and preservatives, and may be lyophilized to be re-constituted at the time of administration.

Compounds and compositions of the present invention are also useful in a variety of in vitro applications, including a range of diagnostic uses. In exemplary in vitro assays, compounds and compositions of the invention can be used as CNS imaging agents. In other embodiments, the compounds of the invention can be used in a variety of conventional, clinical assays to determine whether it is desired to administer a compound of the present invention, or a particular dosage form or quantity of the compound, to a particular patient as a therapeutic agent. For example, assays employing cell cultures, tissue cultures, or animal model systems can be used to demonstrate safety and efficacy of the compounds and pharmaceutical formulations described herein. Additional uses of the compounds of the invention, e.g., in radiolabeled or other labeled form, can be used to study biochemical mechanisms, metabolic processes, pharmacokinetics, etc. of the subject compounds and/or their targets in a diverse array of in vitro, ex vivo, and in vivo assays. Each of the foregoing general applications of the subject compounds will be understood by those skilled in the art to have many corresponding embodiments and modified formats following conventional methods and procedures widely known in the art.

The following examples illustrate certain embodiments of the present invention, and are not to be construed as limiting the present disclosure.

Example I

Preparation of 1-heteroaryl-3-azabicyclo[3.1.0]hexanes using Reaction Scheme 1

A. Synthesis of 1-(pyridine-2-yl)-3-azabicyclo[3.1.0]hexane, dihydrochloride

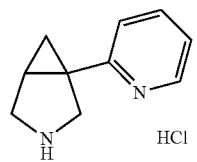 [SMILES: c1ccc(C23CNCC2C3)nc1 ; Cl]

A cooled (−25° C.) stirred suspension of sodium amide (0.43 g, 11 mmol) in anhydrous THF (20 mL) under nitrogen was treated with a solution of pyridine-2-acetonitrile (591 mg, 5.0 mmol) in anhydrous THF (5 mL) and stirred at room temperature for 3 h. The mixture was cooled (−25° C.) and treated with a solution of epichlorohydrin (0.52 mL, 6.0 mmol) in anhydrous THF (2 mL) in one portion, then stirred at room temperature for 1.5 h. Reaction was incomplete, so the solution was heated to 35° C. for 1.5 h, then cooled on an ice bath. Saturated aqueous ammonium chloride (5 mL) was added, followed by ethyl acetate (70 mL). The organic layer was separated, the aqueous extracted with more ethyl acetate (30 mL), and the combined organic layers dried (MgSO$_4$) and concentrated in vacuo. The residue was dissolved in methylene chloride and loaded onto a silica gel column (~150 cc) and eluted with 1:1 methylene chloride/ethyl acetate to afford the intermediate cyanocyclopropanemethanol (447 mg, 51%) as a 4:1 E/Z mixture of isomers (by NMR).

An ice-cooled (3° C.) stirred solution of lithium aluminum hydride/THF (3.0 mL, 3.0 mmol) under nitrogen was treated dropwise with a solution of the above cyanocyclopropanemethanol (348 mg, 2.0 mmol) in THF (3 mL), and the mixture stirred on an ice bath for 2 h and carefully quenched dropwise by successive addition of water (0.115 mL), 15% aqueous sodium hydroxide (0.115 mL), and water (0.35 mL). The suspension was diluted with THF to loosen it up, stirred a few minutes, filtered, and the filtrate concentrated in vacuo (toluene added to ensure water removal). The residual oil was dissolved in anhydrous 1,2-dichloroethane (DCE, 12 mL), cooled (3° C.), and treated with thionyl chloride (0.175 mL, 2.4 mmol). The mixture was warmed to room temperature, stirred 3 h, concentrated in vacuo, and the residue taken up in water (10 mL). The aqueous solution was made basic with 5N NaOH (~2 mL), extracted with methylene chloride containing a little 2-propanol (5×15 mL), and the combined extracts dried (Na$_2$SO$_4$) and concentrated in vacuo. The residue was dissolved in methylene chloride and loaded onto a silica gel column (~50 cc) and eluted with 80:18:2 methylene chloride/ethanol/ammonium hydroxide to afford 1-(pyridine-2-yl)-3-azabicyclo[3.1.0]hexane (225 mg, 70%) as a pale amber oil. MS (M+1) 161.0. $^1$H NMR (CDCl$_3$) δ 8.48 (m, 1H), 7.56 (m, 1H), 7.03-7.12 (m, 2H), 3.40 (m, 1H), 3.31 (d, 1H, J=11 Hz), 3.11 (dd, 1H, J=11 Hz, 3 Hz), 3.04 (d, 1H, J=11 Hz), 1.98 (m, 1H), 1.31 (m, 1H), 0.97 (t, 1H, J=5 Hz).

The above free base (190 mg, 1.18 mmol) was dissolved in methanol (5 mL) and treated with 2N HCl/ether (1.5 mL, 3 mmol) and the resulting solution was concentrated in vacuo. The residue was triturated from a mixture of ethanol and acetonitrile to afford 1-(pyridine-2-yl)-3-azabicyclo[3.1.0]-hexane, dihydrochloride (184 mg, 67%) as a pale tan solid. MS (M+1) 161.0. $^1$H NMR (DMSO-d$_6$) δ 10.21 (br s, 1H), 9.98 (br s, 1H), 8.64 (m, 1H), 8.24 (t, 1H, J=8 Hz), 7.75 (d, 1H, J=8 Hz), 7.67 (t, 1H, J=7 Hz), 3.73 (m, 2H), 3.45-3.57 (m, 1H), 3.38 (m, 1H), 2.51 (m, 1H), 1.74 (t, 1H, J=6 Hz), 1.50 (dd, 1H, J=6 Hz, 9 Hz). $^{13}$C NMR (DMSO-d$_6$) δ 155.19, 144.08, 142.81, 124.12, 123.87, 47.84, 46.34, 30.39, 25.75, 16.55.

Synthesis of 3-methyl-1-(pyridine-2-yl)-3-azabicyclo[3.1.0]hexane, dihydrochloride

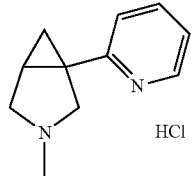

A solution of 1-(pyridine-2-yl)-3-azabicyclo[3.1.0]hexane (240 mg, 1.5 mmol) in anhydrous methylene chloride (10 mL) was treated with di-tert-butyl dicarbonate (382 mg, 1.75 mmol), stirred for 2 h, and concentrated in vacuo (with toluene added late). An ice-cooled stirred solution of 1N LAH/THF (4.5 mL, 4.5 mmol) under nitrogen was treated dropwise with a solution of the above residue in anhydrous THF (3.5 mL), then the mixture was stirred for 1 h at room temperature and for 5 h at reflux, cooled on an ice bath, and carefully quenched dropwise successively with water (0.17 mL), 15% aqueous sodium hydroxide (0.17 mL), and water (0.50 mL). The suspension was diluted with THF to loosen it up, stirred a few minutes, filtered, and the filtrate concentrated in vacuo.

The residue was dissolved in methylene chloride, loaded onto a silica gel column (~75 cc), and eluted with 95:4.5:0.5, then 90:9:1 methylene chloride/ethanol/ammonium hydroxide to afford a colorless oil. This was dissolved in methanol (5 mL), treated with 2N HCl/ether (1.5 mL, 3.0 mL), and concentrated in vacuo to a solid. Trituration from ether afforded 3-methyl-1-(pyridine-2-yl)-3-azabicyclo[3.1.0]hexane, dihydrochloride (214 mg, 58%) as a white solid. MS (M+1) 175.1. $^1$H NMR (DMSO-$d_6$) δ 11.63 (br s, 1H), 8.64 (m, 1H), 8.23 (t, 1H, J=8 Hz) 7.73 (d, 1H, J=8 Hz), 7.66 (t, 1H, J=7 Hz), 3.82-3.97 (m, 2H), 3.61 (m, 2H), 2.81 (br s, 3H), 2.45 (m, 1H), 2.03 (t, 1H, J=6 Hz), 1.52 (m, 1H). $^{13}$C NMR (DMSO-$d_6$) δ 154.90, 144.42, 142.52, 123.94, 57.18, 55.65, 30.25, 25.69, 15.93.

Synthesis of
1-(pyridine-3-yl-3-azabicyclo[3.1.0]hexane,d dihydrochloride

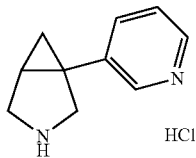 [SMILES: c1cncc(C23CNCC2C3)c1 ; Cl]

A cooled (−25° C.) stirred solution of pyridine-3-acetonitrile (1.18 g, 10 mmol) in anhydrous THF (25 mL) under nitrogen was treated with 1.0N sodium bis(trimethylsilyl)amide (11 mL, 11 mmol), warmed to room temperature, stirred 10 min, then recooled (−25° C.). More base (12 mL, 12 mmol) was added, followed by epichlorohydrin (1.04 mL, 12 mmol) in one portion, and the mixture was stirred at room temperature for 2 h, cooled on an ice bath, and quenched (10 mL saturated aqueous ammonium chloride), followed by dilution with ethyl acetate (100 mL). The organic layer was separated and the aqueous extracted with ethyl acetate (25 mL). The combined organic solution was dried (MgSO$_4$) and concentrated in vacuo, and the residual brown solid dissolved in methylene chloride and loaded onto a silica gel column (~250 cc). This was eluted with ethyl acetate, then 5% ethanol/ethyl acetate, then 10% ethanol/ethyl acetate to afford an orange solid, which was recrystallized from ethyl acetate/heptane to afford the intermediate cyanocyclopropanemethanol (625 mg, 36%) as a 3.5:1 E/Z mixture of isomers (by NMR). An ice-cooled (3° C.) stirred solution of lithium aluminum hydride/THF (4.1 mL, 4.1 mmol) under nitrogen was treated dropwise with a solution of the above cyanocyclopropanemethanol (470 mg, 2.7 mmol) in THF (4 mL), and the mixture stirred on an ice bath for 2 h and carefully quenched dropwise successively with water (0.16 mL), 15% aqueous sodium hydroxide (0.16 mL), and water (0.48 mL). The suspension was diluted with THF/isopropanol to loosen it up, stirred a few minutes, filtered, and the filtrate concentrated in vacuo (toluene added to ensure water removal). The residual oil was dissolved in anhydrous 1,2-dichloroethane (DCE, 12 mL), cooled (3° C.), and treated with thionyl chloride (0.22 mL, 3.0 mmol). The mixture was warmed to room temperature, stirred 3 h, concentrated in vacuo, and the residue taken up in water (10 mL). The aqueous solution was basified with 5N NaOH (~3 mL), extracted with methylene chloride containing a little 2-propanol (4×25 mL), and the combined extracts dried (MgSO$_4$) and concentrated in vacuo. The residue was dissolved in methylene chloride and loaded onto a silica gel column (~50 cc) and eluted with 80:18:2 methylene chloride/ethanol/ammonium hydroxide to afford 1-(pyridine-3-yl)-3-azabicyclo[3.1.0]hexane (156 mg, 36%) as a pale yellow oil. The above free base (68 mg, 0.424 mmol) was dissolved in methanol (2 mL) and treated with 2N HCl/ether (1.0 mL, 2.0 mmol), then the solution was concentrated in vacuo. The residue was rinsed with ether and triturated from acetonitrile to afford 1-(pyridine-3-yl)-3-azabicyclo[3.1.0]-hexane, dihydrochloride (67 mg, 68%) as a pale tan solid. MS (M+1) 161.0. $^1$H NMR (DMSO-$d_6$) δ 10.20 (br s, 1H), 9.95 (br s, 1H), 8.87 (m, 1H), 8.74 (d, 1H, J=5 Hz), 8.41 (m, 1H), 7.94 (dd, 1H, J=6 Hz, 9 Hz), 3.74 (m, 1H), 3.42-3.60 (m, 2H), 3.37 (m, 1H), 2.37 (m, 1H), 1.64 (t, 1H, J=6 Hz), 1.30 (m, 1H). $^{13}$C NMR (DMSO-$d_6$) δ 143.15, 141.00, 140.31, 139.35, 126.38, 48.27, 46.41, 28.42, 24.30, 16.15.

D. Synthesis of 3-Methyl-1-(pyridine-3-yl)-3-azabicyclo[3.1.0]hexane, dihydrochloride

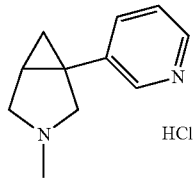

A solution of 1-(pyridine-3-yl)-3-azabicyclo[3.1.0]hexane (81.7 mg, 0.51 mmol) in anhydrous methylene chloride (3 mL) was treated with di-tert-butyl dicarbonate (120 mg, 0.55 mmol), stirred for 2 h, and concentrated in vacuo (with toluene added late). An ice-cooled stirred solution of 1N LAH/THF (1.5 mL, 1.5 mmol) under nitrogen was treated dropwise with a solution of the above residue in anhydrous THF (1.5 mL), then the mixture was stirred for 1 h at room temperature and for 5 h at reflux, cooled on an ice bath, and carefully quenched dropwise successively with water (0.07 mL), 15% aqueous sodium hydroxide (0.07 mL), and water (0.22 mL). The suspension was diluted with THF/isopropanol to loosen it up, stirred a few minutes, filtered, and the filtrate concentrated in vacuo. The residue was dissolved in methylene chloride, loaded onto a silica gel column (~70 cc), and eluted with 95:4.5:0.5, then 90:9:1 methylene chloride/ethanol/ammonium hydroxide to afford a pale tan oil. This was dissolved in methanol (5 mL), treated with 2N HCl/ether (0.75 mL, 1.5 mL), and concentrated in vacuo to a solid. Trituration from ether afforded 3-methyl-1-(pyridine-3-yl)-3-azabicyclo[3.1.0]hexane, dihydrochloride (73 mg, 58%) as a pale tan solid. MS (M+1) 175.0. $^1$H NMR (DMSO-$d_6$) δ 11.59 (br s, 1H), 8.91 (m, 1H), 8.76 (d, 1H, J=5 Hz), 8.43 (m, 1H), 7.94 (dd, 1H, J=6 Hz, 9 Hz), 3.93 (m, 1H), 3.58-3.70 (m, 2H), 3.50 (m, 1H), 2.79 (br s, 3H), 2.33 (m, 1H), 1.97 (t, 1H, J=6 Hz), 1.34 (m, 3H). $^{13}$C NMR (DMSO-$d_6$) δ 143.13, 141.39, 140.63, 138.89, 126.34, 57.54, 55.71, 28.27, 24.37, 15.39.

E. Synthesis of
1-(pyridine-4-yl)-3-azabicyclo[3.1.0]hexane, dihydrochloride

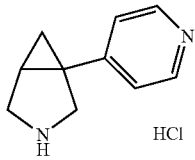 [SMILES: c1cc(C23CNCC2C3)ccn1 ; Cl]

A cooled (−25° C.) stirred solution of pyridine-4-acetonitrile (1.83 g, 15.5 mmol) in anhydrous THF (40 mL) under nitrogen was treated with 1.0N sodium bis(trimethylsilyl)amide (16 mL, 16 mmol), warmed to room temperature, stirred 15 min, then recooled (−25° C.). More base (17 mL, 17 mmol) was added, followed by epichlorohydrin (1.56 mL, 18 mmol) in one portion, and the mixture was stirred at room temperature for 18 h, cooled on an ice bath, and quenched (15 mL saturated aqueous ammonium chloride), followed by dilution with ethyl acetate (200 mL). The organic layer was separated and the aqueous extracted with ethyl acetate (50 mL). The combined organic solution was dried (MgSO$_4$) and concentrated in vacuo, and the residual brown oil dissolved in methylene chloride and loaded onto a silica gel column (~300 cc). This was eluted with 10% ethanol/methylene chloride to afford the intermediate cyanocyclopropanemethanol (750 mg, 28%) as a viscous amber oil, a 5:1 E/Z mixture of isomers (by NMR).

An ice-cooled (3° C.) stirred solution of lithium aluminum hydride/THF (6.5 mL, 6.5 mmol) under nitrogen was treated dropwise with a solution of the above cyanocyclopropanemethanol (740 mg, 4.25 mmol) in THF (6 mL), and the mixture stirred on an ice bath for 2 h and carefully quenched dropwise successively with water (0.25 mL), 15% aqueous sodium hydroxide (0.25 mL), and water (0.75 mL). The suspension was diluted with THF/isopropanol to loosen it up, stirred a few minutes, filtered, and the filtrate concentrated in vacuo (toluene added to ensure water removal). The residual oil was dissolved in anhydrous 1,2-dichloroethane (DCE, 20 mL), cooled (3° C.), and treated with thionyl chloride (0.33 mL, 4.5 mmol). The mixture was warmed to room temperature, stirred 3 h, concentrated in vacuo, and the residue taken up in water (10 mL). The aqueous solution was basified with 5N NaOH (~4 mL), extracted with methylene chloride containing a little 2-propanol (5×25 mL), and the combined extracts dried (Na$_2$SO$_4$) and concentrated in vacuo. The residue was dissolved in methylene chloride and loaded onto a silica gel column (~100 cc) and eluted with 90:9:1, then 85:13.5:1.5 methylene chloride/ethanol/ammonium hydroxide to afford 1-(pyridine-4-yl)-3-azabicyclo[3.1.0]hexane (175 mg, 26%) as an amber oil.

The above free base (101 mg, 0.63 mmol) was dissolved in methanol (5 mL) and treated with 2N HCl/ether (1.0 mL, 2.0 mmol), then the solution was concentrated in vacuo. The residue was triturated from ether to afford 1-(pyridine-4-yl)-3-azabicyclo[3.1.0]hexane, dihydrochloride (130 mg, 88%) as a white solid. MS (M+1) 161.0. $^1$H NMR (DMSO-d$_6$) δ 10.33 (br s, 1H), 10.10 (br s, 1H), 8.79 (d, 2H, J=7 Hz), 7.82 (d, 2H, J=7 Hz), 3.78 (m, 1H), 3.64 (m, 1H), 3.41 (m, 2H), 2.58 (m, 1H), 1.94 (t, 1H, J=6 Hz), 1.49 (m, 1H). $^{13}$C NMR (DMSO-d$_6$) δ 161.21, 141.84, 124.18, 47.35, 46.78, 31.72, 28.81, 21.28.

F. Synthesis of 3-methyl-1-(pyridine-4-yl)-3-azabicyclo[3.1.0]hexane, dihydrochloride

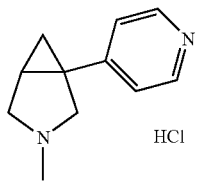

A stirred solution of 1-(pyridine-4-yl)-3-azabicyclo[3.1.0]hexane (272 mg, 1.7 mmol) in DCE (50 mL) was treated with 37% aqueous formaldehyde (1.02 mL, 13.6 mmol), then with sodium triacetoxyborohydride (1.44 g, 6.8 mmol) and stirred at room temperature for 3 h. 1N sodium hydroxide (25 mL) was added, stirring continued for 15 min, the organic layer was separated, and the aqueous solution extracted with methylene chloride (2×50 mL). The combined organic extracts were dried (MgSO$_4$), concentrated in vacuo, dissolved in methylene chloride, and loaded onto a silica gel column (~100 cc). This was eluted with 95:4.5:0.5, then 90:10:1 methylene chloride/ethanol/ammonium hydroxide to afford product free base as a colorless oil. This was dissolved in methanol, treated with 2N HCl/ether (2 mL, 4 mmol), concentrated in vacuo, and the residual solid triturated from ether to afford 3-methyl-1-(pyridine-4-yl)-3-azabicyclo[3.1.0]hexane, dihydrochloride (285 mg, 68%) as a white solid. MS (M+1) 175.0. $^1$H NMR (DMSO-d$_6$) δ 11.76 (br s, 1H), 8.80 (d, 2H, J=7 Hz), 7.78 (d, 2H, J=7 Hz), 3.99 (m, 1H), 3.76 (m, 1H), 3.64 (m, 1H), 3.46 (m, 1H), 2.79 (br s, 3H), 2.57 (m, 1H), 2.25 (t, 1H, J=6 Hz), 1.49 (m, 1H). $^{13}$C NMR (DMSO-d$_6$) δ 159.52, 141.58, 123.31, 55.82, 55.29, 30.63, 27.94, 19.99.

G. Synthesis of 1-(6-methoxypyridine-3-yl)-3-azabicyclo[3.1.0]hexane, dihydrochloride

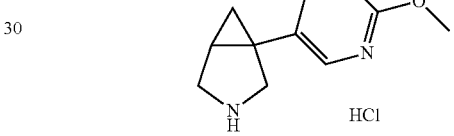

A cooled (−25° C.) stirred solution of 6-methoxypyridine-3-acetonitrile (1.48 g, 10.0 mmol) in anhydrous THF (25 mL) under nitrogen was treated with 1.0N sodium bis(trimethylsilyl)amide (11 mL, 11 mmol), warmed to room temperature, stirred 15 min, then recooled (−25° C.). More base (12 mL, 12 mmol) was added, followed by epichlorohydrin (1.04 mL, 12 mmol) in one portion, and the mixture was stirred at room temperature for 2 h, cooled on an ice bath, and quenched (10 mL saturated aqueous ammonium chloride), followed by dilution with ethyl acetate (100 mL). The organic layer was separated and the aqueous extracted with ethyl acetate (25 mL). The combined organic solution was dried (MgSO$_4$) and concentrated in vacuo, and the residue dissolved in ethyl acetate and loaded onto a silica gel column (~150 cc). This was eluted with ethyl acetate to afford the intermediate cyanocyclopropanemethanol (970 mg, 47%) as a viscous pale yellow oil, a 5:2 E/Z mixture of isomers (by NMR).

An ice-cooled (3° C.) stirred solution of the above cyanocyclopropanemethanol (960 mg, 4.7 mmol) in anhydrous THF (8 mL) under nitrogen was treated dropwise with 1N LAH/THF (7.1 mL, 7.1 mmol) at a rate to keep pot temp<8° C., then stirred at 3° C. for 2 h and carefully dropwise quenched with water (0.27 mL), 15% aqueous sodium hydroxide (0.27 mL), and water (0.80 mL). The thick suspension was diluted with THF to facilitate stirring, stirred for 15 min, then filtered through Celite® (filter cake rinsed with THF). The filtrate was concentrated in vacuo and the residue was dissolved in methylene chloride and loaded onto a column of silica gel (~130 cc), then eluted with 80:18:2 methylene chloride/ethanol/ammonium hydroxide to afford the intermediate aminomethylcyclopropanemethanol (496 mg, 51%) as a pale yellow oil.

An ice-cooled (3° C.) stirred solution of the above aminomethylcyclopropanemethanol (489 mg, 2.35 mmol) in anhydrous DCE (12 mL) under nitrogen was treated dropwise with thionyl chloride (0.205 mL, 2.8 mmol), then stirred for 3 h at room temperature and concentrated in vacuo. The residue was taken up in water (10 mL), stirred for 15 min, basified with 5N NaOH (3 mL), and extracted with methylene chloride containing a little isopropanol (4×25 mL). The combined organic solution was rinsed with water (30 mL), dried (MgSO$_4$), and concentrated in vacuo. The residue was dissolved in methylene chloride, loaded onto a silica gel column (~75 cc), and eluted with 90:9:1, then 80:18:2 methylene chloride/ethanol/ammonium hydroxide to afford bicyclic amine free base (192 mg, 43%) as a pale yellow viscous oil.

A solution of the above bicyclic amine free base (70 mg, 0.368 mmol) in methanol (5 mL) was treated with 2N HCl/ether (0.5 mL, 1.0 mmol), the solution concentrated in vacuo, and the residual solid triturated successively with ether and acetonitrile to afford 1-(6-methoxypyridine-3-yl)-3-azabicyclo[3.1.0]hexane, dihydrochloride (82 mg, 85%) as a white solid. MS (M+1) 190.9. $^1$H NMR (DMSO-d$_6$) 9.96 (br s, 1H), 9.71 (br s, 1H), 8.11 (m, 1H), 7.67 (m, 1H), 6.81 (m, 1H), 3.82 (s, 3H), 3.61 (m, 1H), 3.45 (m, 1H), 3.28-3.40 (m, 2H), 2.05 (m, 1H), 1.39 (m, 1H), 1.04 (m, 1H). $^{13}$C NMR (DMSO-d) δ 162.27, 144.91, 138.90, 128.04, 110.23, 53.49, 49.40, 46.68, 27.93, 22.48, 14.45.

H. Synthesis of 1-(6-methoxypyridine-3-yl)-3-methyl-3-azabicyclo[3.1.0]hexane, dihydrochloride

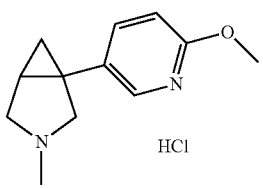

A stirred solution of 1-(6-methoxypyridine-3-yl)-3-azabicyclo[3.1.0]hexane (90 mg, 0.473 mmol) in DCE (15 mL) was treated with 37% aqueous formaldehyde (0.29 mL, 3.8 mmol), followed by sodium triacetoxyborohydride (0.403 g, 1.9 mmol), and stirred at room temperature for 3 h. 1N sodium hydroxide (6 mL) was added, stirring continued for 15 min, and the organic layer was separated and the aqueous solution extracted with methylene chloride (3×15 mL). The combined organic extracts were dried (Na$_2$SO$_4$), concentrated in vacuo, dissolved in methylene chloride, and loaded onto silica gel (~50 cc). This was eluted with 95:4.5:0.5, then 85:13.5:1.5 methylene chloride/ethanol/ammonium hydroxide to afford the above free base as a colorless oil, which was dissolved in methanol (5 mL). The stirred solution was treated with 2N HCl/ether (0.5 mL, 1.0 mmol), concentrated in vacuo, and the residual solid triturated with ether to afford 1-(6-methoxypyridine-3-yl)-3-methyl-3-azabicyclo[3.1.0]hexane, dihydrochloride (101 mg, 77%) as a white solid. MS (M+1) 204.9. $^1$H NMR (DMSO-d) δ 11.36 (br s, 1H), 8.12 (m, 1H), 7.71 (m, 1H), 6.82 (m, 1H), 3.82 (s, 3H), 3.77-3.87 (m, 1H), 3.57 (m, 1H), 3.45 (m, 2H), 2.76 (br s, 3H), 2.04 (m, 1H), 1.76 (m, 1H), 1.05 (m, 1H). $^{13}$C NMR (DMSO-d$_6$) δ 162.36, 145.07, 138.91, 127.78, 110.21, 58.50, 55.93, 53.47, 27.78, 22.54, 14.13.

I. Synthesis of 1-(5-methylfuran-2-yl)-3-azabicyclo[3.1.0]hexane, hydrochloride

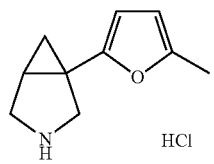

A cooled (3° C.) stirred suspension of sodium amide (1.37 g, 35 mmol) in anhydrous THF (40 mL) under nitrogen was treated with a solution of 5-methylfuran-2-acetonitrile (1.82 g, 15 mmol) in anhydrous THF (20 mL), stirred 1.5 h at room temperature, and recooled (3° C.). Epichlorohydrin (1.53 mL, 19.5 mmol) was added, and the mixture stirred at room temperature for 2 h, then cooled on an ice bath and quenched with saturated aqueous ammonium chloride (15 mL). After stirring for 15 min, the mixture was taken up in ethyl acetate (150 mL) and the organic layer separated. The aqueous solution was extracted with ethyl acetate (30 mL) and the combined organic solution was dried (MgSO$_4$) and concentrated in vacuo. The residue was dissolved in methylene chloride and loaded onto a silica gel column (~150 cc) and eluted with methylene chloride, 5% ethyl acetate/methylene chloride, and 10% ethyl acetate/methylene chloride to afford the intermediate cyanocyclopropanemethanol (1.25 g, 47%) as an amber oil, a 2:1 E/Z mixture of isomers (by NMR).

A cooled (−25° C.) stirred solution of the intermediate cyanocyclopropanemethanol (1.24 g, 7.00 mmol) in anhydrous THF (15 mL) was carefully treated dropwise with 1.0N LAH/THF (14 mL, 14 mmol), then stirred for 3 h on an ice bath. The solution was cooled (−25° C.) and carefully treated dropwise with water (0.53 mL), 15% NaOH (0.53 mL), and water (1.6 mL), diluted with THF to facilitate stirring, stirred 15 min, and filtered through Celite® (filter cake rinsed with THF). The filtrate was concentrated in vacuo and the residue dissolved in methylene chloride and loaded onto a silica gel column (~150 cc). This was eluted with 9:1 methylene chloride/ethanol, 95:4.5:0.5 methylene chloride/ethanol/ammonium hydroxide, and 90:9:1 methylene chloride/ethanol/ammonium hydroxide to afford the intermediate aminomethylcyclopropanemethanol (453 mg, 38%) as a pale amber oil. MS (M+1) 181.9. $^1$H NMR (CDCl$_3$) δ 5.91 (m, 1H), 5.83 (m, 1H), 4.08 (dd, 1H, J=12 Hz, 5 Hz), 3.67 (d, 1H, J=13 Hz), 3.28 (dd, 1H, J=13 Hz, 11 Hz), 2.48 (d, 1H, J=12 Hz), 2.23 (s, 3H), 1.78 (m, 1H), 1.08 (dd, 1H, J=9 Hz, 5 Hz), 0.68 (t, 1H, J=5 Hz).

A cooled (3° C.) stirred solution of the intermediate aminomethylcyclopropanemethanol (435 mg, 2.4 mmol) in anhydrous DCE (15 mL) was treated dropwise with thionyl chloride (0.22 mL, 3.0 mmol). The solution was stirred 3 h at room temperature, then concentrated in vacuo, taken up in water (15 mL), stirred 15 min, and basified (3 mL of 5N NaOH). The dark aqueous mixture was extracted with methylene chloride (3×40 mL) and the combined extracts washed with brine (50 mL), dried (Na$_2$SO$_4$) and concentrated in vacuo. The residue was dissolved in methylene chloride, loaded onto a silica gel column (~75 cc), and eluted with 90:9:1 methylene chloride/ethanol/ammonium hydroxide to afford the bicyclic amine free base (158 mg, 40%) as an amber glass. MS (M+) 163.9.

A solution of the bicyclic amine free base (70 mg, 0.429 mmol) in methylene chloride (5 mL) was treated with 2N HCl/ether (0.25 mL, 0.50 mmol), stirred a few minutes, then concentrated in vacuo. The residue was triturated from ether to afford 1-(5-methylfuran-2-yl)-3-azabicyclo[3.1.0]hexane, hydrochloride (65 mg, 76%) as a brown solid. MS (M+1) 163.9. $^1$H NMR (CDCl$_3$) δ 10.26 (br s, 1H), 9.75 (br s, 1H), 5.90 (m, 2H), 3.45-3.75 (m, 4H), 2.23 (s, 3H), 1.89 (m, 1H), 1.50 (m, 1H), 1.36 (m, 1H). $^{13}$C NMR (CDCl$_3$) δ 151.59, 149.26, 106.89, 106.28, 48.37, 47.26, 25.71, 23.46, 13.45, 13.35.

J. Synthesis of 1-(benzofuran-3-yl)-3-azabicyclo[3.1.0]hexane hydrochloride

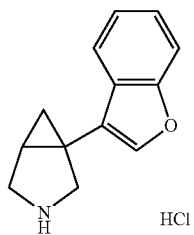 [SMILES: c1ccc2c(C34CNCC3C4)coc2c1 ; Cl]

A cooled (3° C.) stirred suspension of sodium amide (1.37 g, 35 mmol) in anhydrous THF (45 mL) under nitrogen was treated with a solution of benzofuran-3-acetonitrile (2.36 g, 15 mmol) in anhydrous THF (15 mL), stirred 1 h at room temperature, and recooled (3° C.). Epichlorohydrin (1.53 mL, 19.5 mmol) was added, and the mixture stirred at room temperature for 1 h, then cooled on an ice bath and quenched with saturated aqueous ammonium chloride (15 mL). After stirring for 15 min, the mixture was taken up in ethyl acetate (150 mL) and the organic layer separated. The aqueous solution was extracted with ethyl acetate (2×20 mL) and the combined organic solution was dried (MgSO$_4$) and concentrated in vacuo. The residue was dissolved in methylene chloride and loaded onto a silica gel column (~150 cc) and eluted with 5% ethyl acetate/methylene chloride, then 10% ethyl acetate/methylene chloride to afford the intermediate cyanocyclopropanemethanol (1.83 g, 57%) as a pale amber oil, a 2:1 E/Z mixture of isomers (by NMR).

A cooled (−25° C.) stirred solution of the intermediate cyanocyclopropanemethanol (1.80 g, 8.44 mmol) in anhydrous THF (15 mL) was carefully treated dropwise with 1.0N LAH/THF (14.8 mL, 14.8 mmol), then stirred for 3 h on an ice bath. The solution was carefully treated dropwise with water (0.60 mL), 15% NaOH (0.60 mL), and water (1.7 mL), diluted with THF to facilitate stirring, stirred 15 min, and filtered through Celite® (filter cake rinsed with THF). The filtrate was concentrated in vacuo and the residue dissolved in methylene chloride and loaded onto a silica gel column (~125 cc). This was eluted with 90:9:1, then 85:13.5:1.5 methylene chloride/ethanol/ammonium hydroxide to afford the intermediate aminomethylcyclopropanemethanol (1.06 g, 58%) as a viscous colorless oil. MS (M+1) 217.9. $^1$H NMR (CDCl$_3$) δ 7.76 (m, 1H), 7.59 (s, 1H), 7.47 (m, 1H), 7.23-7.33 (m, 2H), 4.16 (dd, 1H, J=13 Hz, 5 Hz), 3.57 (d, 1H, J=12 Hz), 3.38 (dd, 1H, J=13 Hz, 11 Hz), 2.59 (d, 1H, J=12 Hz), 1.76 (m, 1H), 0.99 (dd, 1H, J=9 Hz, 5 Hz), 0.80 (t, 1H, J=5 Hz).

A cooled (3° C.) stirred solution of the intermediate aminomethylcyclopropanemethanol (1.03 g, 4.75 mmol) in anhydrous DCE (25 mL) was treated dropwise with thionyl chloride (0.44 mL, 6.0 mmol). The solution was stirred 3 h at room temperature, then concentrated in vacuo, taken up in water (15 mL), stirred 25 min, and basified (6 mL of 5N NaOH). The aqueous mixture was extracted with methylene chloride (4×50 mL) and the combined extracts washed with brine (50 mL), dried (Na$_2$SO$_4$) and concentrated in vacuo. The residue was dissolved in methylene chloride, loaded onto a silica gel column (~150 cc), and eluted with 95:4.5:0.5, then 90:9:1, then 85:13.5:1.5 methylene chloride/ethanol/ammonium hydroxide to afford the bicyclic amine free base (709 mg, 75%) as a pale tan solid. MS (M+1) 180.0. $^1$H NMR (CDCl$_3$) δ 7.55 (m, 1H), 7.46 (m, 1H), 7.44 (s, 1H), 7.20-7.32 (m, 2H), 3.15-3.26 (m, 3H), 3.09 (d, 1H, J=11 Hz), 1.76 (m, 1H), 1.05 (dd, 1H, J=8 Hz, 5 Hz), 0.83 (t, 1H, J=5 Hz).

A stirred solution of the above bicyclic amine free base (240 mg, 1.205 mmol) in anhydrous ether (5 mL) was treated with 2.0N HCl/ether (1.0 mL, 2.0 mmol), stirred until a solid formed and for a few minutes more, filtered, and the solid rinsed with ether, collected, and dried in vacuo to afford 1-(benzofuran-3-yl)-3-azabicyclo[3.1.0]hexane, hydrochloride (266 mg, 94%) as a white solid. MS (M+1) 199.9. $^1$H NMR (CDCl$_3$) δ 10.35 (br s, 1H), 9.89 (br s, 1H), 7.53 (d, 1H, J=8 Hz), 7.50 (s, 1H), 7.48 (d, 1H, J=8 Hz), 7.23-7.35 (m, 2H), 3.60-3.80 (m, 4H), 2.01 (m, 1H), 1.62 (m, 1H), 1.32 (d, 1H, J=8 Hz). $^{13}$C NMR (CDCl$_3$) δ 155.49, 142.93, 126.52, 124.93, 123.04, 119.43, 117.80, 111.98, 49.98, 47.56, 22.74, 21.54, 13.44.

K. Synthesis of 1-(benzofuran-3-yl)-3-methyl-3-azabicyclo[3.1.0]hexane, hydrochloride

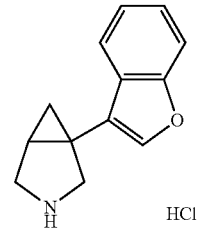 [SMILES: c1ccc2c(C34CNCC3C4)coc2c1 ; Cl]

A stirred solution of 1-(benzofuran-3-yl)-3-azabicyclo [3.1.0]hexane (199 mg, 1.00 mmol) in DCE (25 mL) was treated with 37% aqueous formaldehyde (0.61 mL, 8.0 mmol), then with sodium triacetoxyborohydride (850 mg, 4.0 mmol), and stirred at room temperature for 3 h. 1N Sodium hydroxide (15 mL) was added, stirring was continued for a few minutes, and the organic layer was separated. The aqueous layer was extracted with methylene chloride (2×25 mL) and the combined organic solution was washed with brine (50 mL), dried (Na$_2$SO$_4$) and concentrated in vacuo. The residue was dissolved in methylene chloride, loaded onto a silica gel column (~60 cc), and eluted with 95:4.5:0.5 methylene chloride/ethanol/ammonium hydroxide to afford the bicyclic amine free base. This was dissolved in anhydrous ether (5 mL) and treated with 2N HCl/ether (0.8 mL, 1.6 mmol) and stirred until several minutes after a solid formed, then filtered, rinsed with ether, and the solid collected and dried in vacuo to afford 1-(benzofuran-3-yl)-3-methyl-3-azabicyclo[3.1.0] hexane, hydrochloride (226 mg, 94%) as a white solid. MS (M+1) 213.9. $^1$H NMR (CDCl$_3$) δ 12.64 (br s, 1H), 7.45-7.55 (m, 3H), 7.23-7.25 (m, 2H), 4.08 (m, 1H), 3.96 (m, 1H), 3.41

(m, 1H), 3.29 (m, 1H), 2.92 (br s, 3H), 2.23 (m, 1H), 2.06 (m, 1H), 1.27 (t, 1H, J=8 Hz). $^{13}$C NMR (CDCl$_3$) 155.45, 143.01, 126.44, 125.03, 123.05, 119.11, 117.61, 112.09, 59.57, 57.09, 41.24, 22.65, 21.45, 13.87.

L. Synthesis of 1-(5-methylthiophen-2-yl)-3-azabicyclo[3.1.0]hexane, hydrochloride

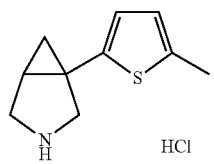

A cooled (3° C.) stirred suspension of sodium amide (1.25 g, 32 mmol) in anhydrous THF (35 mL) under nitrogen was treated with a solution of 5-methylthiophen-2-acetonitrile[1,2] (1.85 g, 13.5 mmol) in anhydrous THF (15 mL), stirred 1.5 h at room temperature, and recooled (3° C.). Epichlorohydrin (1.40 mL, 17.8 mmol) was added, and the mixture stirred at room temperature for 2 h, then cooled on an ice bath and quenched with saturated aqueous ammonium chloride (15 mL). After stirring for 15 min, the mixture was taken up in ethyl acetate (125 mL) and the organic layer separated. The aqueous solution was extracted with ethyl acetate (25 mL) and the combined organic solution was dried (MgSO$_4$) and concentrated in vacuo. The residue was dissolved in methylene chloride and loaded onto a silica gel column (~150 cc) and eluted with 10% ethyl acetate/methylene chloride, then 20% ethyl acetate/methylene chloride to afford the intermediate cyanocyclopropanemethanol (1.74 g, 67%) as an amber oil, a 2:1 E/Z mixture of isomers (by NMR).

A cooled (−20° C.) stirred solution of the intermediate cyanocyclopropanemethanol (1.64 g, 8.50 mmol) in anhydrous THF (15 mL) was carefully treated dropwise with 1.0N LAH/THF (17 mL, 17 mmol), then stirred for 3 h on an ice bath. The solution was cooled (−20° C.) and carefully treated dropwise with water (0.65 mL), 15% NaOH (0.65 mL), and water (2.0 mL), diluted with THF to facilitate stirring, stirred 15 min, and filtered through Celite® (filter cake rinsed with THF). The filtrate was concentrated in vacuo and the residue dissolved in methylene chloride and loaded onto a silica gel column (~125 cc). This was eluted with 90:9:1 methylene chloride/ethanol/-ammonium hydroxide to afford the intermediate aminomethylcyclopropanemethanol (584 mg, 35%) as a pale yellow oil. MS (M+1) 198.1. $^1$H NMR (CDCl$_3$) δ 6.73 (m, 1H), 6.54 (m, 1H), 4.09 (dd, 1H, J=12 Hz, 5 Hz), 3.52 (d, 1H, J=13 Hz), 3.29 (dd, 1H, J=13 Hz, 11 Hz), 2.56 (d, 1H, J=12 Hz), 2.42 (br s, 3H), 1.84 (m, 1H), 1.03 (dd, 1H, J=9 Hz, 5 Hz), 0.77 (t, 1H, J=5 Hz).

A cooled (3° C.) stirred solution of the intermediate aminomethylcyclopropanemethanol (572 mg, 2.90 mmol) in anhydrous DCE (15 mL) was treated dropwise with thionyl chloride (0.27 mL, 3.7 mmol). The solution was stirred 3 h at room temperature, then concentrated in vacuo, taken up in water (15 mL), stirred 15 min, and basified (4 mL of 5N NaOH). The aqueous mixture was extracted with methylene chloride (4×30 mL) and the combined extracts washed with brine (50 mL), dried (Na$_2$SO$_4$) and concentrated in vacuo. The residue was dissolved in methylene chloride, loaded onto a silica gel column (~150 cc), and eluted with 95:4.5:0.5, then 90:9:1 methylene chloride/ethanol/ammonium hydroxide to afford the bicyclic amine free base (308 mg, 59%) as a brown oil. MS (M+1) 180.0. $^1$H NMR (CDCl$_3$) δ 6.59 (m, 1H), 6.54 (m, 1H), 3.10-3.22 (m, 3H), 2.99 (d, 1H, J=12 Hz), 2.41 (s, 3H), 1.61 (m, 1H), 1.04 (m, 1H), 0.88 (t, 1H, J=5 Hz).

A solution of the bicyclic amine free base (163 mg, 0.909 mmol) in anhydrous ether (5 mL) was treated with 2N HCl/ether (0.75 mL, 1.50 mmol), stirred a few hours, the solid filtered, rinsed with ether, collected, and dried in vacuo to afford 1-(5-methylthiophen-2-yl)-3-azabicyclo[3.1.0]hexane, hydrochloride (174 mg, 89%) as a pale gray solid. MS (M+1) 179.9. $^1$H NMR (CDCl$_3$) δ 10.22 (br s, 1H), 9.74 (br s, 1H), 6.65 (m, 1H), 6.55 (m, 1H), 3.50-3.75 (m, 4H), 2.41 (s, 3H), 1.87 (m, 1H), 1.59 (m, 1H), 1.30 (m, 1H). $^{13}$C NMR (CDCl$_3$) δ 139.00, 138.98, 125.15, 125.04, 50.83, 47.40, 27.39, 24.89, 15.97, 15.26.

M. Synthesis of 1-(5-methylthiophen-2-yl)-3-methyl-3-azabicyclo[3.1.0]hexane, hydrochloride

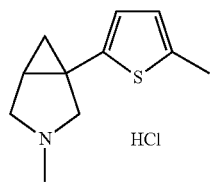

A stirred solution of 1-(5-methylthiophen-2-yl)-3-azabicyclo[3.1.0]hexane (126 mg, 0.70 mmol) in DCE (15 mL) was treated with 37% aqueous formaldehyde (0.43 mL, 5.0 mmol), then with sodium triacetoxyborohydride (594 mg, 2.8 mmol), and stirred at room temperature for 3 h. 1N Sodium hydroxide (12 mL) was added, stirring was continued for a few minutes, and the organic layer was separated. The aqueous layer was extracted with methylene chloride (2×15 mL) and the combined organic solution was washed with brine (20 mL), dried (Na$_2$SO$_4$) and concentrated in vacuo. The residue was dissolved in methylene chloride, loaded onto a silica gel column (~50 cc), and eluted with 95:4.5:0.5 methylene chloride/ethanol/ammonium hydroxide to afford the bicyclic amine free base. This was dissolved in anhydrous ether (5 mL) and treated with 2N HCl/ether (0.6 mL, 1.2 mmol) and stirred for 2 h, then filtered, rinsed with ether, and the solid collected and dried in vacuo to afford 1-(5-methylthiophen-2-yl)-3-methyl-3-azabicyclo[3.1.0]hexane, hydrochloride (133 mg, 82%) as a pale tan solid. MS (M+1) 193.9. $^1$H NMR (CDCl$_3$) δ 12.51 (br s, 1H), 6.65 (m, 1H), 6.55 (m, 1H), 4.02 (m, 1H), 3.85 (m, 1H), 3.18-3.36 (m, 2H), 2.87 (br s, 3H), 2.40 (s, 3H), 2.21 (m, 1H), 1.91 (m, 1H), 1.28 (m, 1H). $^{13}$C NMR (CDCl$_3$) δ 139.22, 138.64, 125.35, 125.09, 60.54, 57.06, 41.31, 27.43, 24.91, 16.54, 15.25.

N. Synthesis of 1-(benzothiazol-2-yl)-3-azabicyclo[3.1.0]hexane, hydrochloride

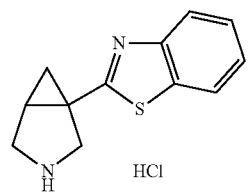 [SMILES: c1ccc2sc(C34CNCC3C4)nc2c1 ; Cl]

An ice-cooled (3° C.) stirred suspension of sodium amide (1.80 g, 46 mmol) in anhydrous THF (50 mL) under nitrogen was treated with a solution of benzothiazole-2-acetonitrile (3.49 g, 20 mmol) in anhydrous THF (20 mL), then stirred at room temperature for 2.5 h. The mixture was recooled (3° C.), treated in one portion with epichlorohydrin (2.1 mL, 26.9 mmol), and stirred at room temperature for 20 h, then cooled on an ice bath and quenched with saturated aqueous ammonium chloride (20 mL). The mixture was extracted with ethyl acetate (200 mL, then 50 mL), and the combined extracts were dried (MgSO$_4$) and concentrated in vacuo. The residue was dissolved in methylene chloride, loaded onto a silica gel column (~250 cc), and eluted with 4:1 methylene chloride/ethyl acetate to afford the intermediate cyanocyclopropanemethanol (1.00 g, 22%) as a pale tan foam, a somewhat still crude mixture of isomers (by NMR). MS (M+1) 231.7.

A cooled (−25° C.) stirred solution of the intermediate cyanocyclopropanemethanol (1.00 g, 4.34 mmol) in anhydrous THF (7 mL) under nitrogen was treated dropwise with 1N LAH/THF (6.5 mL, 6.5 mmol), stirred at 3° C. for 2 h, recooled (−25° C.), and carefully quenched dropwise with water (0.25 mL), 15% NaOH 0.25 mL), and water (0.75 mL). Extra THF was added to facilitate stirring, and after a few minutes the mixture was filtered through Celite® (filter cake rinsed with THF). The filtrate was concentrated in vacuo, and the residue dissolved in methylene chloride and loaded onto a silica gel column (~125 cc) and eluted with 90:9:1, then 85:13.5:1.5 methylene chloride/ethanol/ammonium hydroxide to afford the intermediate aminomethylcyclopropanemethanol (137 mg, 13%) as an orange viscous oil. MS (M+1) 234.7. $^1$H NMR (CDCl$_3$) δ 7.88 (d, 1H, J=8 Hz), 7.77 (d, 1H, J=8 Hz), 7.41 (t, 1H, J=8 Hz), 7.30 (t, 1H, J=8 Hz), 4.10-4.18 (m, 2H), 3.37 (t, 1H, J=12 Hz), 2.58 (d, 1H, J=−12 Hz), 2.02 (m, 1H), 1.43 (dd, 1H, J=9 Hz, 5 Hz), 1.12 (t, 1H, J=6 Hz).

An ice-cooled (3° C.) stirred solution of the intermediate aminomethylcyclopropanemethanol (137 mg, 0.585 mmol) in anhydrous DCE (3 mL) under nitrogen was treated with thionyl chloride (87 mg, 0.73 mmol) and stirred at room temperature for 3 h, then concentrated in vacuo. Water (2 mL) was added, stirring continued for 15 min, then the solution was basified with 5N sodium hydroxide (1 mL) and extracted with 5:1 methylene chloride/isopropanol (3×15 mL). The combined extracts were dried (MgSO$_4$), concentrated in vacuo, and the residue dissolved in methylene chloride and loaded onto a silica gel column (~50 cc). This was eluted with 90:9:1, then 85:13.5:1.5 methylene chloride/ethanol/ammonium hydroxide to afford 1-(benzothiazol-2-yl)-3-azabicyclo[3.1.0]hexane (88 mg, 70%) as an amber solid. This was dissolved in ether containing a little methanol (5 mL), treated with 2.0N HCl/ether (0.40 mL, 0.80 mmol), the solvent evacuated from the flask, and the residual solid triturated from ether to afford 1-(benzothiazol-2-yl)-3-azabicyclo[3.1.0]hexane, hydrochloride (99 mg, 96% from free base) as a pale brick-colored powder. MS (M+1) 216.8. $^1$H NMR (DMSO-d$_6$) δ 10.20 (br s, 1H), 9.95 (br s, 1H), 8.05 (d, 1H, J=8 Hz), 7.91 (d, 1H, J=8 Hz), 7.48 (t, 1H, J=8 Hz), 7.39 (t, 1H, J=8 Hz), 3.88 (m, 1H), 3.73 (m, 1H), 3.50 (m, 1H), 3.38 (m, 1H), 2.35 (m, 1H), 1.88 (t, 1H, J=6 Hz), 1.59 (m, 1H). $^{13}$C NMR (DMSO-d$_6$) δ 170.19, 152.52, 133.73, 126.46, 125.09, 122.20, 121.98, 47.52, 46.39, 31.07, 28.61, 18.23.

O. Synthesis of 1-(5-chlorothiophen-3-yl)-3-azabicyclo[3.1.0]hexane, hydrochloride

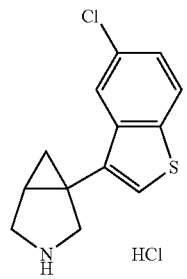 [SMILES: Clc1ccc2scc(C34CNCC3C4)c2c1 ; Cl]

A cooled (3° C.) stirred suspension of sodium amide (0.90 g, 23 mmol) in anhydrous THF (30 mL) under nitrogen was treated with a solution/suspension of 5-chlorobenzothiophen-3-acetonitrile (2.08 g, 10 mmol) in anhydrous THF (10 mL), stirred 1 h at room temperature, and recooled (3° C.). Epichlorohydrin (1.04 mL, 12 mmol) was added, and the mixture stirred at room temperature for 4 h, then cooled on an ice bath and quenched with saturated aqueous ammonium chloride (10 mL). After stirring for 15 min, the mixture was taken up in ethyl acetate (100 mL) and the organic layer separated. The aqueous solution was extracted with ethyl acetate (50 mL) and the combined organic solution was dried (MgSO$_4$) and concentrated in vacuo. The residue was dissolved in methylene chloride and loaded onto a silica gel column (~150 cc) and eluted with 10% ethyl acetate/methylene chloride to afford the intermediate cyanocyclopropanemethanol (1.51 g, 57%) as a tan solid, a 4:1 E/Z mixture of isomers (by NMR).

A ice-cooled (3° C.) stirred solution of 1.0N LAH/THF (5.25 mL, 5.25 mmol) under nitrogen was treated dropwise with a solution of the intermediate cyanocyclopropanemethanol (932 mg, 3.5 mmol) in anhydrous THF (5 mL), and the mixture was stirred 2 h at 3° C. Water (0.2 mL), 15% NaOH (0.2 mL), and water (0.6 mL) were carefully added dropwise, and the mixture was diluted with THF and stirred 15 min at room temperature, filtered through Celite® (filter cake rinsed with THF), and the filtrate concentrated in vacuo. The residue was dissolved in methylene chloride, loaded onto a silica gel column (~60 cc), and eluted with 10% EtOH/CH$_2$Cl$_2$, then 90:9:1 methylene chloride/ethanol/ammonium hydroxide to afford the intermediate aminomethylcyclopropanemethanol (650 mg, 69%) as a white solid. MS (M+1) 267.7. $^1$H NMR (CDCl$_3$) δ 7.94 (d, 1H, J=2 Hz), 7.76 (d, 1H, J=9 Hz), 7.46 (s, 1H), 7.32 (dd, 1H, J=9 Hz, 2 Hz), 4.18 (dd, 1H, J=12 Hz, 5.5 Hz), 3.54 (d, 1H, J=12 Hz), 3.39 (t, 1H, J=11 Hz), 2.60 (d, 1H, J=12 Hz), 1.80 (m, 1H), 1.01 (dd, 1H, J=9 Hz, 5 Hz), 0.89 (t, 1H, J=5 Hz).

A cooled (3° C.) stirred solution of the intermediate aminomethylcyclopropanemethanol (0.65 g, 2.43 mmol) in anhydrous DCE (12 mL) was treated dropwise with thionyl chloride (0.20 mL, 2.70 mmol). The solution was stirred 3 h at room temperature, then concentrated in vacuo, taken up in water (10 mL), stirred 15 min, and basified (3 mL of 5N NaOH). The aqueous mixture was extracted with methylene chloride (4×25 mL) and the combined extracts washed with brine (30 mL), dried (Na$_2$SO$_4$) and concentrated in vacuo. The residue was dissolved in methylene chloride, loaded onto a silica gel column (~75 cc), and eluted with 95:4.5:0.5, then 90:9:1 methylene chloride/ethanol/ammonium hydroxide to afford the bicyclic amine free base (435 mg, 72%) as a white solid. MS (M+1) 249.7. $^1$H NMR (CDCl$_3$) δ 7.79 (d, 1H, J=2 Hz), 7.75 (d, 1H, J=9 Hz), 7.30 (dd, 1H, J=9 Hz, 2 Hz), 7.27 (s, 1H), 3.33 (dd, 1H, J=12 Hz, 2.5 Hz), 3.24 (d, 1H, J=11 Hz), 3.14 (d, 1H, J=12 Hz), 3.09 (d, 1H, 0.1=12 Hz), 1.71 (m, 1H), 0.96 (m, 1H), 0.89 (t, 1H, J=5 Hz).

A stirred solution of the above bicyclic amine free base (150 mg, 0.60 mmol) in anhydrous ether (6 mL) was treated with 2.0N HCl/ether (0.5 mL, 1.0 mmol), stirred for 2 h, filtered, and the solid rinsed with ether, collected, and dried in vacuo to afford 1-(5-chlorothiophen-3-yl)-3-azabicyclo[3.1.0]hexane, hydrochloride (166 mg, 97%) as a white solid. MS (M+1) 249.7. $^1$H NMR (CDCl$_3$) δ 10.23 (br s, 1H), 9.83 (br s, 1H), 7.69 (d, 1H, J=9 Hz), 7.67 (d, 1H, J=2 Hz), 7.33 (s, 1H), 7.27 (dd, 1H, J=9 Hz, 2 Hz), 3.74 (m, 2H), 3.65 (m, 1H), 3.45 (m, 1H), 1.97 (m, 1H), 1.61 (m, 1H), 1.17 (m, 1H). $^{13}$C NMR (CDCl$_3$) δ 139.41, 138.71, 132.01, 131.09, 127.97, 125.36, 124.22, 121.37, 50.52, 47.64, 26.29, 21.50, 13.68.

P. Synthesis of 1-(5-chlorothiophen-3-yl)-3-methyl-3-azabicyclo[3.1.0]hexane, hydrochloride

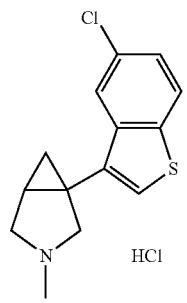 [SMILES: CN1CC2CC2(c2csc3ccc(Cl)cc23)C1 ; Cl]

A stirred solution of 1-(5-chlorothiophen-3-yl)-3-azabicyclo[3.1.0]hexane (150 mg, 0.60 mmol) in DCE (20 mL) was treated with 37% aqueous formaldehyde (0.37 mL, 4.8 mmol), then with sodium triacetoxyborohydride (510 mg, 2.4 mmol), and stirred at room temperature for 3 h. 1N Sodium hydroxide (8 mL) was added, stirring was continued for 15 min, and the organic layer was separated. The aqueous layer was extracted with methylene chloride (2×25 mL) and the combined organic solution was washed with brine (50 mL), dried (Na$_2$SO$_4$) and concentrated in vacuo. The residue was dissolved in methylene chloride, loaded onto a silica gel column (~75 cc), and eluted with 95:4.5:0.5 methylene chloride/ethanol/ammonium hydroxide to afford the bicyclic amine free base. This was dissolved in anhydrous ether (5 mL) and treated with 2N HCl/ether (0.5 mL, 1.0 mmol) and stirred for 30 min, then filtered, rinsed with ether, and the solid collected and dried in vacuo to afford 1-(5-chlorothiophen-3-yl)-3-methyl-3-azabicyclo[3.1.0]hexane, hydrochloride (153 mg, 85%) as a white solid. MS (M+1) 263.8. $^1$H NMR (CDCl$_3$) δ 12.68 (br s, 1H), 7.77 (d, 1H, J=9 Hz), 7.70 (d, 1H, J=2 Hz), 7.44 (s, 1H), 7.34 (dd, 1H, J=9 Hz, 2 Hz), 4.10 (dd, 1H, J=11 Hz, 5 Hz), 4.02 (dd, 1H, J=1 Hz, 5 Hz), 3.50 (m, 1H), 3.20 (t, 1H, J=10 Hz), 2.94 (br s, 3H), 2.30 (m, 1H), 2.08 (m, 1H), 1.21 (t, 1H, J=8 Hz). $^{13}$C NMR (CDCl$_3$) δ 139.22, 138.75, 131.64, 131.12, 128.30, 125.41, 124.38, 121.05, 59.88, 57.15, 41.26, 26.24, 21.49, 13.96.

Example II

Preparation of 1-heteroaryl-3-methyl-3-azabicyclo[3.1.0]hexanes using Reaction Scheme 2

A. Synthesis of 3-methyl-(1-methylindol-2-yl)-3-azabicyclo[3.1.0]bicyclohexane, hydrochloride

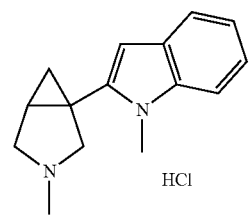 [SMILES: CN1CC2CC2(c2cc3ccccc3n2C)C1 ; Cl]

A stirred solution of N-methylbromomaleimide (1.9 g 10 mmol) and 1-methyl-2-(tributhyltin)indole (5.25 g, 12.5 mmol) in anhydrous dioxane (60 mL) was degassed under a stream of nitrogen for 10 minutes, then treated with cesium fluoride (3.6 g, 23.6 mmol) and Cl$_2$Pd(PPh$_3$)$_2$ (0.4 g 0.6 mmol), stirred at room temperature for 0.5 h, then at 40° C. for 1 h and at 50° C. for 2 h. Then the reaction mixture was cooled to room temperature, methylene chloride (100 ml) added, and the mixture was filtered through celite, concentrated and purified by silica gel chromatography (2% ethyl acetate/methylene chloride) to afford maleimide intermediate (1.2 g, 98%). $^1$H NMR (CDCl$_3$) δ 7.72-7.68 (m, 1H), 7.62-7.61 (m, 1H), 7.36-7.33 (m, 2H), 7.17-7.12 (m, 1H) 6.59-6.57 (m, 1H), 3.89 (s, 3H) 3.11 (s, 3H).

A cooled (−20° C.) stirred solution of trimethylsulfoxonium chloride (0.892 g, 6.96 mmol) in anhydrous tetrahydrofuran (30 mL) under nitrogen was treated with n-butyllithium/hexane (2.5N, 2.2 mL, 5.5 mmol) and warmed to 50° C. over 30 minutes. A solution of the above maleimide intermediate (1.2 g, 5 mmol) in anhydrous tetrahydrofuran (25 mL) was warmed to 50° C. and added all at once. After 2 h at 50° C., the mixture was cooled on ice and quenched with saturated aqueous ammonium chloride (2 mL). The mixture was stirred at room temperature for 15 minutes, then it was added to methylene chloride (100 mL) and the organic solution was dried (Na$_2$SO$_4$) and concentrated in vacuo. The residue was dissolved in methylene chloride, loaded onto a silica gel column and eluted with 2% ethyl acetate/methylene chloride to afford diimide intermediate (140 mg, 12%). $^1$H NMR (CDCl$_3$) δ 7.59-7.54 (m, 11H), 7.35-7.30 (m, 1H), 7.28-7.23 (m, 1H), 7.14-7.08 (m, 1H), 6.46-6.43 (m, 1H), 3.82 (s, 3H), 2.96 (s, 3H), 2.83-2.78 (m, 1H), 1.99-1.96 (m, 1H) 1.92-1.87 (m, 1H).

A stirred, ice-cooled (2° C.) solution of 1N lithium aluminum hydride/THF (3.43 mL, 3.43 mmol) under nitrogen was treated dropwise with a solution of the above diimide intermediate (140 mg, 0.55 mmol) in anhydrous tetrahydrofuran (20 mL), stirred for 1 h at room temperature and 7 h at reflux, then cooled on an ice bath. Water (0.30 mL), 15% NaOH (0.30 mL) and water (0.90 mL) were added dropwise together with more tetrahydrofuran to facilitate stirring. The mixture was stirred at room temperature for 15 minutes, filtered through celite, and the filtrate concentrated in vacuo. The residue was dissolved in methylene chloride, loaded onto a silica gel column, and eluted with 3:1 methylene chloride/ethyl acetate to afford 3-methyl-1-(1-methylindol-2-yl)-3-azabicyclo[3.1.0]bicyclohexane (100 mg, 80%), which was then converted to the hydrochloride salt by treating with 2N HCl/ether (82 mg, 80%). MS (M+1) 226.8 $^1$H NMR (DMSO-d$_6$) δ 11.35-11.12 (br s, 1H), 7.52-7.34 (m, 2H), 7.15-6.93 (m, 2H), 6.45-6.34 (m, 1H), 3.92-3.84 (m, 1H), 3.79-3.75 (s, 3H), 3.71-3.64 (m, 1H), 3.63-3.56 (m, 1H), 3.39-3.26 (m, 1H), 2.81 (d, 3H), 2.24-2.16 (m, 1H), 1.91-1.83 (m, 1H), 1.11-1.01 (m, 1H). $^{13}$C NMR (DMSO-d$_6$) δ 138.06, 137.98, 127.38, 122.00, 14.21, 120.67, 119.98, 110.28, 102.01, 59.38, 56.47, 40.36, 30.96, 24.26, 22.51.

B. Synthesis of 3-methyl-1-(1-methylindol-5-yl)-3-azabicyclo[3.1.0]bicyclohexane, hydrochloride

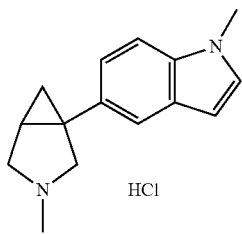 [SMILES: CN1CC2CC2(c2ccc3c(ccn3C)c2)C1 ; Cl]

A stirred solution of N-methylbromomaleimide (1.8 g, 9.5 mmol) and 1-methylindole-5-boronic acid (2 g, 11.4 mmol) in dioxane (50 mL) was degassed under a stream of nitrogen for 10 minutes, then treated with cesium fluoride (3.8 g, 24.7 mmol) and Cl$_2$Pd(dppf).CH$_2$Cl$_2$ (0.475 g, 0.58 mmol), then stirred at room temperature for 1 hour and at 40° C. for 1 h. The mixture was cooled and diluted with methylene chloride, stirred a few minutes and filtered through celite. The filtrate was concentrated in vacuo and purified by silica gel chromatography using 2% ethyl acetate/methylene chloride as an eluting solvent to afford maleimide intermediate (2.17 g, 95%). $^1$H NMR (CDCl$_3$) δ 8.43 (d, 1H, J=1.5 Hz), 7.74 (dd, 1H, J=8.5 Hz, 1.5 Hz), 7.37 (d, 1H, J=9 Hz), 6.66 (s, 1H), 6.60 (d, 1H, J=3 Hz), 3.83 (s, 3H), 3.10 (s, 3H).

A cooled (−20° C.) stirred solution of trimethylsulfoxonium chloride (1.4 g, 11.25 mmol) in anhydrous tetrahydrofuran (40 mL) under nitrogen was treated with n-butyllithium/hexane (2.5N, 3.6 mL, 9 mmol) and warmed to 50° C. over 30 minutes. A solution of the above maleimide intermediate (2 g, 8.3 mmol) in anhydrous tetrahydrofuran (40 mL) was warmed to 50° C. and added all at once. After 2 h at 50° C., the mixture was cooled on ice and quenched with saturated aqueous ammonium chloride. The mixture was stirred at room temperature for 15 minutes, then it was added to methylene chloride (150 mL) and the organic solution was dried (Na$_2$SO$_4$) and concentrated in vacuo. The residue was purified by silica gel chromatography, using ethyl acetate/methylene chloride to afford bicyclic diimide intermediate (500 mg, 25%). $^1$H NMR (CDCl$_3$) δ 7.61-7.65 (m, 1H), 7.30-7.34 (m, 1H), 7.23-7.26 (m, 1H), 7.07 (d, 1H, =3 Hz), 6.46 (dd, 1H, J=3 Hz, 1 Hz,), 3.79 (s, 1H), 2.94 (s, 3H), 1.90 (dd, 1H, J=8 Hz, 4.5 Hz), 1.84-1.87 (m, 1H).

A stirred, ice-cooled (2° C.) solution of 1N lithium aluminum hydride/THF (12 mL, 12 mmol) under nitrogen was treated dropwise with a solution of the above bicyclic diimide intermediate (0.5 g, 1.96 mmol) in anhydrous tetrahydrofuran (10 mL), stirred for 1 h at room temperature and 2 h at reflux, then cooled on an ice bath. Water (0.4 mL), 15% NaOH (0.4 mL), and water (1.2 mL) were added dropwise together with more tetrahydrofuran to facilitate stirring. The mixture was stirred at room temperature for 15 minutes, filtered through celite, and the filtrate concentrated in vacuo. The residue was purified by silica gel chromatography, using methylene chloride/methanol as an eluting solvent to afford 3-methyl-1-(1-methylindol-5-yl)-3-azabicyclo[3.1.0]bicyclo-hexane, hydrochloride (0.262 g, 60%), which was converted to the hydrochloride salt by treating with 2N HCl/ether (270 mg, 90%). MS (M+1) 227. $^1$H NMR (CDCl$_3$) δ 12.21 (br s, 1H), 7.45 (s, 1H), 7.22-7.28 (m, 1H), 7.02-7.07 (m, 2H), 6.40 (d, 1H, J=2.5 Hz), 4.05 (dd, 1H, J=10.5 Hz, 5 Hz), 3.88 (dd, 1H, J=10 Hz, 4.5 Hz), 3.74 (s, 3H), 3.62-3.71 (m, 1H), 3.32-3.40 (m, 1H), 3.27 (t, 1H, J=9.5 Hz), 2.87 (d, 3H, J=4 Hz), 2.06-2.11 (m, 1H), 1.93-1.99 (m, 1H). $^{13}$C NMR (CDCl$_3$) 136.19, 130.17, 128.82, 128.50, 121.34, 120.10, 109.91, 100.99, 61.73, 57.75, 41.43, 33.17, 32.18, 22.95, 15.68.

C. Synthesis of 1-(quinolin-5-yl)-3-methyl-3-azabicyclo[3.1.0]hexane hydrochloride

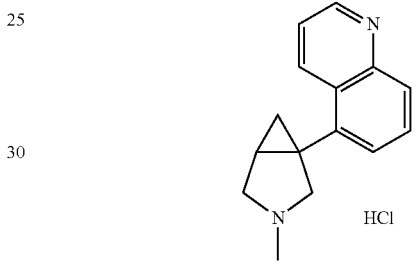

A stirred solution/suspension of N-methylbromomaleimide (0.78 g, 4.1 mmol) and quinoline-5-boronic acid (1.1 g, 2.6 mmol) in dioxane (15 mL) under nitrogen was degassed with a stream of nitrogen for 10 min, treated with cesium fluoride (1.6 g, 10.8 mmol) and Cl$_2$Pd(dppf).CH$_2$Cl$_2$ (0.25 g, 0.3 mmol), then stirred at room temperature for 0.5 h and at 45° C. for 30 min then at 65° C. for 45 min. The mixture was cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride 60% and ethyl acetate 40%) to afford a yellowish solid, which was triturated from cold petroleum ethers to afford the arylmaleimide intermediate (0.48 g, 50%) as a pale yellow solid.

A cooled (−20° C.) stirred solution of trimethylsulfoxonium chloride (290 mg, 2.2 mmol) in anhydrous tetrahydrofuran (15 mL) under nitrogen was treated dropwise with n-butyllithium/hexane (2.4N, 1.1 mL, 2.03 mmol) and gradually warmed to 50° C. over 30 minutes. Meanwhile, a solution of the intermediate arylmaleimide (0.690 g, 2.6 mmol) in anhydrous THF (10 mL) was heated to 50° C., then added quickly in one portion to the above heated suspension, and the mixture was stirred at 50° C. for 2 h, then cooled on an ice bath. Saturated aqueous ammonium chloride (1 mL) was added to quench, and the mixture was diluted with methylene chloride (75 mL), dried (MgSO$_4$), filtered through Celite® (rinse with methylene chloride), and concentrated in vacuo. The residue was dissolved in methylene chloride, loaded onto a silica gel column, and the product eluted with 3% ethyl acetate/methylene chloride to afford the intermediate bicyclic diimide (120 mg, 24%) as a very pale yellow viscous oil.

A stirred ice-cooled solution of 1.0N borane/THF (10.5 mL, 10.5 mmol) under nitrogen was treated dropwise with a solution of the above bicyclic diimide intermediate (120 mg, 0.48 mmol) in anhydrous THF (10 mL). The solution was stirred at room temperature for 15 min, refluxed for 4 h, cooled on an ice bath, and carefully treated dropwise with 6N HCl (10 mL, vigorous evolution of gas). The solution was concentrated to a white solid, which was partitioned between 5N sodium hydroxide (25 mL) and ether (50 mL). The organic layer was separated and the aqueous extracted with ether (50 mL). The combined organic solution was washed with water (25 mL), dried ($Mg_2SO_4$), and concentrated in vacuo. The residue was dissolved in methanol (23 mL), treated with 4N HCl/dioxane (7 mL), then stirred at room temperature for 16 h and at 55° C. for 4 h. The solution was concentrated in vacuo and the residue triturated from ether to afford 1-(quinolin-5-yl)-3-methyl-3-azabicyclo[3.1.0]hexane, hydrochloride (50 mg, 20%) as a white solid. MS (M+1) 225.1. $^1$H NMR (CDCl$_3$) δ 7.23 (dd, 1H, J=6.5 Hz, 2 Hz), 7.01-7.15 (m, 2H), 4.10 (dd, 1H, J=11 Hz, 5 Hz), 3.92 (dd, 1H, J=11 Hz, 5 Hz), 2.95-3.30 (m, 4H), 2.36 (dd, 1H, J=6.5 Hz, 4.5 Hz), 1.93-2.02 (m, 1H), 1.51 (t, 3H, J=7 Hz), 1.13-1.20 (m, 1H). $^{13}$C NMR (DMSO-d$_6$) δ 146.98, 141.45, 140.98, 137.01, 133.53, 131.50, 128.73, 127.46, 123.07, 61.39, 60.37, 56.60, 29.59, 22.58, 14.35.

D. Synthesis of 1-(quinolin-3-yl)-3-methyl-3-azabicyclo[3.1.0]hexane, hydrochloride

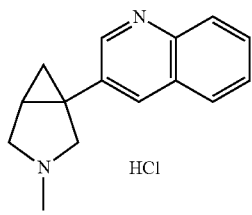 [SMILES: CN1CC2CC2(c2cnc3ccccc3c2)C1 ; Cl]

A stirred solution/suspension of 3-bromo-1-methylmaleimide (2.0 g. 10.5 mmol) and quinoline-3-boronic acid (2.2 g, 12.6 mmol) in dioxane (50 mL) under nitrogen was degassed with a stream of nitrogen for 10 min, treated with cesium fluoride (3.5 g, 22.0 mmol) and Cl$_2$Pd(dppf).CH$_2$Cl$_2$ (0.5 g, 0.6 mmol), then stirred at room temperature for 0.5 h, at 45° C. for 30 min, and at 65° C. for 45 min. The mixture was cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride 60% and ethyl acetate 40%) to afford a tan solid, which was triturated from cold petroleum ethers to afford arylmaleimide intermediate (880 mg, 15%) as a tan solid.

A cooled (−20° C.) stirred solution of trimethylsulfoxonium chloride (261 mg, 2.03 mmol) in anhydrous tetrahydrofuran (15 mL) under nitrogen was treated dropwise with n-butyllithium/hexane (2.4N, 1.1 mL, 2.03 mmol) and gradually warmed to 50° C. over 30 minutes. Meanwhile, a solution of the intermediate arylmaleimide (0.350 g, 1.5 mmol) in anhydrous THF (10 mL) was heated to 50° C., then added quickly in one portion to the above heated suspension, and the mixture was stirred at 50° C. for 2 h, then cooled on an ice bath. Saturated aqueous ammonium chloride (1 mL) was added to quench, and the mixture was diluted with methylene chloride (75 mL), dried (MgSO$_4$), filtered through Celite® (rinse with methylene chloride), and concentrated in vacuo. The residue was dissolved in methylene chloride, loaded onto a silica gel column, and the product eluted with 3% ethyl acetate/methylene chloride to afford the intermediate bicyclic diimide (148 mg, 50%) as a very pale yellow viscous oil. $^1$H NMR (CDCl$_3$) δ 7.74-7.90 (m, 3H), 7.38-7.55 (m, 3H), 4.54 (dd, 2H), 3.86 (d, 6H, J=4.5 Hz), 2.81 (dd, 1H, J=8 Hz, 3.5 Hz), 1.91 (dd, 1H, J=8 Hz, 4.5 Hz), 1.78 (dd, 1H, J=—4.5, 3.5 Hz).

A stirred ice-cooled solution of 1.0N borane/THF (10.5 mL, 10.5 mmol) under nitrogen was treated dropwise with a solution of the above bicyclic diimide intermediate (560 mg, 2.1 mmol) in anhydrous THF (10 mL). The solution was stirred at room temperature for 15 min, refluxed for 4 h, cooled on an ice bath, and carefully treated dropwise with 6N HCl (10 mL, vigorous evolution of gas). The solution was concentrated to a white solid, which was partitioned between 5N sodium hydroxide (25 mL) and ether (50 mL). The organic layer was separated and the aqueous extracted with ether (50 mL). The combined organic solution was washed with water (25 mL), dried (Mg$_2$SO$_4$), and concentrated in vacuo. The residue was dissolved in methanol (23 mL), treated with 4N HCl/dioxane (7 mL), then stirred at room temperature for 16 h and at 55° C. for 4 h. The solution was concentrated in vacuo and the residue triturated from ether to afford 1-(quinolin-3-yl)-3-methyl-3-azabicyclo[3.1.0]hexane, hydrochloride (100 mg, 20%) as a white solid. MS (M+1) 240.1. $^1$H NMR (CDCl$_3$) δ 7.23 (dd, 1H, J=6.5 Hz, 2 Hz), 7.01-7.15 (m, 2H), 4.10 (dd, 1H, J=11 Hz, 5 Hz), 3.92 (dd, 1H, J=11 Hz, 5 Hz), 2.95-3.30 (m, 4H), 2.36 (dd, 1H, J=6.5 Hz, 4.5 Hz), 1.93-2.02 (m, 1H), 1.51 (t, 3H, J=7 Hz, 3 Hz), 1.13-1.20 (m, 1H). $^{13}$C NMR (DMSO-d$_6$) δ 146.98, 141.45, 140.98, 137.01, 133.53, 131.50, 128.73, 127.46, 123.07, 61.39, 60.37, 56.60, 29.59, 22.58, 14.35.

Example III

Preparation of 1-heteroaryl-3-ethyl-3-azabicyclo[3.1.0]hexanes using Reaction Scheme 2

A. Synthesis of 3-bromo-1-ethylmaleimide

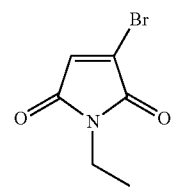

A cooled (5° C.) solution of N-ethylmaleimide (20 g, 0.16 mole) in carbon tetrachloride (20 mL) under nitrogen was treated dropwise over 45 min with bromine (23 g, 0.14 mole) at a rate to keep the pot temp <10° C. The mixture was stirred at 5° C. for 2 hours. Dichloromethane (20 mL) was added to the reaction and N$_2$ was bubbled through the reaction for 15 min to remove excess bromine. The reaction was blown dry with a steady stream of N$_2$ and then brought up in ethanol. Anhydrous sodium acetate (12.3 g, 0.15 mole) was added and the reaction was refluxed for 4 hours. The reaction was concentrated in vacuo and the residue taken up in methylene chloride (300 mL), filtered and concentrated in vacuo to yield an orange oil. Pure 3-bromo-1-ethylmaleimide was obtained from recrystallization in chloroform to yield a yellowish solid (26 g, 82%). $^1$H NMR (CDCl$_3$) δ 1.20 (t, J=7.22 Hz, 3H) 3.62 (q, 0.1=7.22 Hz, 2H) 6.85 (s, 1H).

B. Synthesis of 1-(quinolin-3-yl)-3-ethyl-3-azabicyclo[3.1.0]hexane, hydrochloride

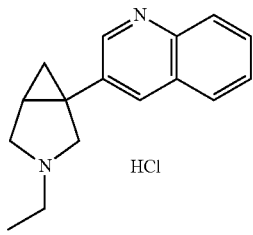 [SMILES: CCN1CC2CC2(c2cnc3ccccc3c2)C1 ; Cl]

A stirred solution/suspension of 3-bromo-1-ethylmaleimide (2.4 g, 5.9 mmol) and 3-quinolineboronic acid (2.2 g, 6.5 mmol) in dioxane (15 mL) under nitrogen was degassed with a stream of nitrogen for 10 min, treated with cesium fluoride (3.2 g, 10.8 mmol) and POPd (Combiphos, cat#AC1000) (0.500 g, 0.5 mmol), then stirred at room temperature for 0.5 h and at 45° C. for 30 min then at 65° C. for 45 min. The mixture was cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride 60% and ethyl acetate 40%) to afford a light gray solid, which was triturated from cold petroleum ethers to afford the arylmaleimide intermediate (300 mg, 10%) as a gray solid.

A stirred solution of sodium hydride oil dispersion (60%, 140 mg, 3.5 mmol) in anhydrous tetrahydrofuran (30 mL) under nitrogen was treated with trimethyl-sulfoxonium chloride (0.55 g, 4.25 mmol), then refluxed for 2.5 h and cooled (50° C.). The above arylmaleimide (937 mg, 3.5 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual solid was dissolved in 1:1 methylene chloride/heptane and loaded onto a silica gel column and eluted with 1:1, 2:1, then 3:1 methylene chloride/heptane to afford the bicyclic diimide intermediate (250 mg, 64%) as a very pale yellow oil. $^1$H NMR (CDCl$_3$) δ 1.18 (t, 3H) 1.89-1.96 (m, 2H) 2.91 (dd, J=6.44, 5.47 Hz, 1H) 3.46-3.59 (m, 2H) 7.55-7.65 (m, 1H) 7.69-7.81 (m, 1H) 7.84 (d, J=8.20 Hz, 1H) 8.16 (d, J=8.40 Hz, 1H) 8.30 (d, J=1.76 Hz, 1H) 8.92 (d, J=2.34 Hz, 1H).

A stirred ice-cooled solution of 2.0N LAH/THF (1.9 mL, 3.76 mmol) under nitrogen was treated dropwise with a solution of the above bicyclic diimide intermediate (250 mg, 0.94 mmol) in anhydrous THF (10 mL). The solution was stirred at room temperature for 15 min, refluxed for 4 h, cooled on an ice bath, and carefully treated dropwise with 30% NaOH (1.3 mL, vigorous evolution of gas). The solution was filtered and the filtrate was reduced to a clear oil. The residue was dissolved in methanol (23 mL), treated with 4N HCl/dioxane (7 mL), then stirred at room temperature for 3 h. The solution was concentrated in vacuo and the residue triturated from ether to afford 1-(quinolin-3-yl)-3-ethyl-3-azabicyclo[3.1.0]hexane, hydrochloride (105 mg, 43%) as a white solid. MS (M+1) 239. $^1$H NMR (CDCl$_3$) δ 7.25 (m, 1H), 7.08 (m, 2H), 4.04 (m, 1H), 3.85 (m, 1H), 3.35 (m, 2H), 3.21 (m, 1H), 2.39 (m, 1H), 1.97 (m, 1H), 1.50 (d, 6H, J=7 Hz), 1.10 (m, 1H). $^{13}$C NMR (CDCl$_3$) δ 158.83, 156.34, 135.62, 129.93, 127.57, 121.54, 117.17, 59.78, 57.35, 53.99, 30.68, 23.06, 19.05, 16.29.

C. Synthesis of 1-(1-methyl-1H-indol-5-yl)-3-ethyl-3-azabicyclo[3.1.0]hexane, hydrochloride

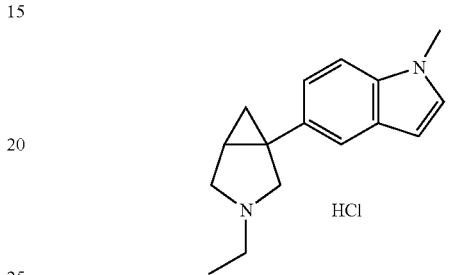

A stirred solution/suspension of 3-bromo-1-ethylmaleimide (0.7 g, 3.43 mmol) and 1-methyl-1H-indol-5-ylboronic acid (0.65 g, 3.7 mmol) in dioxane (15 mL) under nitrogen was degassed with a stream of nitrogen for 10 min, treated with cesium fluoride (1.6 g, 10.8 mmol) and Cl$_2$Pd(dppf) .CH$_2$Cl$_2$ (0.25 g, 0.3 mmol), then stirred at room temperature for 0.5 h and at 45° C. for 30 min then at 65° C. for 45 min. The mixture was cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride 60% and ethyl acetate 40%) to afford an orange solid, which was triturated from cold petroleum ethers to afford arylmaleimide intermediate (585 mg, 67%) as an orange solid.

A stirred suspension of sodium hydride oil dispersion (60%, 140 mg, 3.5 mmol) in anhydrous tetrahydrofuran (30 mL) under nitrogen was treated with trimethyl-sulfoxonium chloride (0.55 g, 4.25 mmol), then refluxed for 2.5 h and cooled (50° C.). The above arylmaleimide (937 mg, 3.5 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual solid was dissolved in 1:1 methylene chloride/heptane and loaded onto a silica gel column and eluted with 1:1, 2:1, then 3:1 methylene chloride/heptane to afford the bicyclic diimide intermediate (628 mg, 64%) as a very pale yellow oil. $^1$H NMR (CDCl$_3$) δ 1.14 (t, 3H) 1.79 (dd, J=4.39, 3.61 Hz, 1H) 1.89 (dd, J=8.10, 4.39 Hz, 1H) 2.70 (dd, J=8.10, 3.61 Hz, 1H) 3.42-3.56 (m, 2H) 3.78-3.81 (m, 1H) 6.46 (dd, J=3.12, 0.78 Hz, 1H) 7.07 (d, J=2.93 Hz, 1H) 7.26 (d, J=1.76 Hz, 1H) 7.29-7.37 (m, 1H) 7.63 (d, J=0.98 Hz, 1H).

A stirred ice-cooled solution of 2.0N LAH/THF (2.2 mL, 2.23 mmol) under nitrogen was treated dropwise with a solution of the above bicyclic diimide intermediate (150 mg, 0.6 mmol) in anhydrous THF (10 mL). The solution was stirred at room temperature for 15 min, refluxed for 4 h, cooled on an ice bath, and carefully treated dropwise with 30% NaOH (1.3 mL, vigorous evolution of gas). The solution was filtered and the filtrate was reduced to a clear oil. The residue was dissolved in methanol (23 mL), treated with 4N HCl/dioxane (7 mL), then stirred at room temperature for 3 h. The solution was concentrated in vacuo and the residue triturated from ether to afford 1-(1-methyl-1H-indol-5-yl)-3-ethyl-3-azabicyclo[3.1.0]hexane, hydrochloride (76 mg, 53%) as a white solid. MS (M+1) 241. $^1$H NMR (CDCl$_3$) δ 1.10 (d, J=6.44 Hz, 1H) 1.48 (t, 3H) 1.92-2.02 (m, 1H) 2.19 (dd, J=6.54, 4.59 Hz, 1H) 3.13-3.25 (m, 3H) 3.25-3.36 (m, 1H) 3.74-3.79 (m, 3H) 3.91 (dd, J=11.03, 5.37 Hz, 1H) 4.10 (dd, J=10.84, 5.37 Hz, 1H) 6.38-6.47 (m, 1H) 6.98-7.12 (m, 2H) 7.26-7.33 (m, 1H) 7.40-7.54 (m, 1H). $^{13}$C NMR (CDCl$_3$) 811.12, 22.47, 31.79, 33.16, 51.48, 55.69, 59.78, 66.05, 100.44, 109.10, 120.10, 121.37, 122.56, 123.34, 129.62.

D. Synthesis of 2-(3-ethyl-3-azabicyclo[3.1.0]hex-1-yl)-1-methyl-1H-indole, hydrochloride

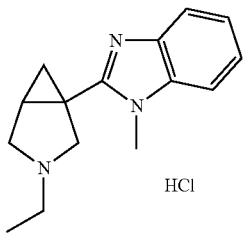 [SMILES: CCN1CC2CC2(c2nc3ccccc3n2C)C1 ; Cl]

A stirred solution/suspension of 3-bromo-1-ethylmaleimide (1.0 g, 4.9 mmol) and 1-methyl-2-tributylstannylindole (2.3 g, 5.4 mmol) in dioxane (15 mL) under nitrogen was degassed with a stream of nitrogen for 10 min, treated with cesium fluoride (1.6 g, 10.8 mmol) and Cl$_2$Pd(dppf).CH$_2$Cl$_2$ (0.25 g, 0.3 mmol), then stirred at room temperature for 0.5 h and at 45° C. for 30 min then at 65° C. for 45 min. The mixture was cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride 60% and ethyl acetate 40%) to afford a yellowish solid, which was triturated from cold petroleum ethers to afford the arylmaleimide intermediate (1.32 g, 87%) as a yellowish solid.

A stirred suspension of sodium hydride oil dispersion (60%, 140 mg, 3.5 mmol) in anhydrous tetrahydrofuran (30 mL) under nitrogen was treated with trimethyl-sulfoxonium chloride (0.495 g, 3.85 mmol), then refluxed for 2.5 h and cooled (50° C.). The above arylmaleimide (900 mg, 3.5 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual solid was dissolved in 1:1 methylene chloride/heptane and loaded onto a silica gel column and eluted with 1:1, 2:1, then 3:1 methylene chloride/heptane to afford the bicyclic diimide intermediate (370 mg, 40%) as a very pale yellow oil. $^1$H NMR (CDCl$_3$) δ 1.15 (t, 3H) 1.86 (dd, 0.1=4.88, 3.71 Hz, 1H) 1.93 (dd, J=8.20, 4.88 Hz, 1H) 2.57 (dd, J=8.30, 3.81 Hz, 1H) 3.44-3.53 (m, 2H) 7.29 (d, J=1.17 Hz, 2H) 7.45 (t, =1.17 Hz, 1H).

A stirred ice-cooled solution of 2.0N LAH/THF (6.0 mL, 5.8 mmol) under nitrogen was treated dropwise with a solution of the above bicyclic diimide intermediate (370 mg, 1.45 mmol) in anhydrous THF (10 mL). The solution was stirred at room temperature for 15 min, refluxed for 4 h, cooled on an ice bath, and carefully treated dropwise with 30% NaOH (1.3 mL, vigorous evolution of gas). The solution was filtered and the filtrate was reduced to a clear oil. The residue was dissolved in methanol (23 mL), treated with 4N HCl/dioxane (7 mL), then stirred at room temperature for 3 h. The solution was concentrated in vacuo and the residue triturated from ether to afford 2-(3-ethyl-3-aza-bicyclo[3.1.0]hex-1-yl)-1-methyl-1H-indole, hydrochloride (262 mg, 75%) as a white solid. MS (M+1) 241. $^1$H NMR (CDCl$_3$) δ 1.12-1.19 (m, 1H) 1.48 (t, J=7.13 Hz, 3H) 2.10-2.20 (m, 1H) 2.39 (dd, 0.1=6.25, 4.69 Hz, 1H) 3.04-3.26 (m, 3H) 3.28-3.42 (m, 1H) 3.78 (s, 3H) 3.93 (dd, 0.1=10.93, 5.27 Hz, 1H) 4.10 (dd, J=10.93, 5.27 Hz, 1H) 6.36 (s, 1H) 7.02-7.15 (m, 1H) 7.15-7.31 (m, 2H) 7.52 (d, J=8.00 Hz, 1H). $^{13}$C NMR (CDCl$_3$) δ|| 11.11, 15.28, 22.42, 24.24, 30.74, 51.55, 54.91, 58.62, 101.39, 109.43, 120.30, 120.78, 122.50, 127.21, 136.70, 137.94.

E. Synthesis of 1-(quinolin-5-yl)-3-ethyl-3-azabicyclo[3.1.0]hexane, hydrochloride

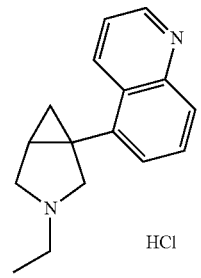 [SMILES: CCN1CC2CC2(c2cccc3ncccc23)C1 ; Cl]

A stirred solution/suspension of 3-bromo-1-ethylmaleimide (0.7 g, 3.43 mmol) and 5-quinolineboronic acid (1.2 g, 5.9 mmol) in dioxane (15 mL) under nitrogen was degassed with a stream of nitrogen for 10 min, treated with cesium fluoride (1.6 g, 10.8 mmol) and Cl$_2$Pd(dppf).CH$_2$Cl$_2$ (0.25 g, 0.3 mmol then stirred at room temperature for 0.5 h and at 45° C. for 30 min then at 65° C. for 45 min. The mixture was cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride 60% and ethyl acetate 40%) to afford a tan solid, which was triturated from cold petroleum ethers to afford the arylmaleimide intermediate (430 mg, 30%) as a tan solid.

A stirred suspension of sodium hydride oil dispersion (60%, 140 mg, 3.5 mmol) in anhydrous tetrahydrofuran (30 mL) under nitrogen was treated with trimethyl-sulfoxonium chloride (0.55 g, 4.25 mmol), then refluxed for 2.5 h and cooled (50° C.). The above arylmaleimide (937 mg, 3.5 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual solid was dissolved in 1:1 methylene chloride/heptane and loaded onto a silica gel column and eluted with 1:1, 2:1, then 3:1 methylene chloride/heptane to afford bicyclic diimide intermediate (628 mg, 64%) as a very pale yellow oil. $^1$H NMR (CDCl$_3$) δ 1.19 (t, 3H) 1.85-1.95 (m, 1H) 1.97-2.08 (m, 1H) 2.82 (dd, =8.40, 3.51 Hz, 1H) 3.47-3.64 (m, 2H) 7.35-7.87 (m, 4H) 8.17 (dd, J=8.49, 3.81 Hz, 1H) 8.82-9.03 (m, 1H).

A stirred ice-cooled solution of 2.0N LAH/THF (0.58 mL, 1.1 mmol) under nitrogen was treated dropwise with a solution of the above bicyclic diimide intermediate (77 mg, 0.29 mmol) in anhydrous THF (10 mL). The solution was stirred at room temperature for 15 min, refluxed for 4 h, cooled on an ice bath, and carefully treated dropwise with 30% NaOH (1.3 mL, vigorous evolution of gas). The solution was filtered and the filtrate was reduced to a clear oil. The residue was dissolved in methanol (23 mL), treated with 4N HCl/dioxane (7 mL), then stirred at room temperature for 3 h. The solution was concentrated in vacuo and the residue triturated from ether to afford 1-(quinolin-5-yl)-3-ethyl)-3-azabicyclo[3.1.0]hexane, hydrochloride (55 mg, 81%) as a white solid. MS (M+1) 239. $^1$H NMR (CDCl$_3$) δ 1.07 (t, J=7.03 Hz, 1H) 1.27 (t, =7.22 Hz, 3H) 1.31-1.38 (m, 1H) 1.61-1.82 (m, 1H) 3.24 (s, 1H) 3.48-3.57 (m, 1H) 3.62-3.79 (m, 2H) 4.06 (dd, J=1.13, 5.27 Hz, 1H) 7.66 (t, J=7.61 Hz, 1H) 7.69-7.83 (m, 1H) 7.97 (s, 1H) 8.06 (d, J=8.79 Hz, 1H) 8.41 (s, 1H) 8.95 (d, J=2.34 Hz, 1H). $^{13}$C NMR (CDCl$_3$) δ 10.96, 29.17, 30.13, 42.07, 51.27, 55.11, 58.82, 122.30, 122.55, 123.77, 128.09, 131.10, 131.49, 134.91, 138.88, 143.98.

Example IV

Preparation of 1-heteroaryl-3-isopropyl-3-azabicyclo[3.1.0]hexanes using Reaction Scheme 2

A. Synthesis of 3-bromo-1-isopropylmaleimide

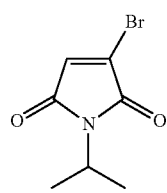

A cooled (5° C.) stirred solution of maleic anhydride (29.4 g, 0.30 mole) in anhydrous ether (150 mL) under nitrogen was treated dropwise over 45 min with a solution of isopropylamine (35.5 g, 0.60 mole) in anhydrous ether (100 mL) at a rate to keep the pot temp <20° C., then the mixture was stirred at 10° C. for 15 min, filtered, and the filter cake rinsed with anhydrous ether and dried in vacuo to afford a white solid. This was taken up in acetic anhydride (250 mL), treated with anhydrous sodium acetate (12.3 g, 0.15 mole), and heated to 75° C. with stirring for 4.5 h, then at 100° C. for 1.5 h. The mixture was concentrated in vacuo and the residue taken up in methylene chloride (300 mL), washed with saturated aqueous sodium bicarbonate (200 mL), water (200 mL), dried (MgSO$_4$), and concentrated in vacuo. The residue was distilled (approx. 5 mm pressure) to afford two products; N-isopropylmaleimide at 82° C. (13.0 g) and an acetate adduct of N-isopropylmaleimide at 154° C. (12.9 g). The acetate adduct was dissolved in 4:1 acetonitrile/triethylamine (100 mL), heated to 65° C. for 4 h, then concentrated in vacuo. The residue was dissolved in methylene chloride and filtered through a pad of silica gel (eluted with methylene chloride) to afford an additional 3.5 g of N-isopropylmaleimide. Total yield was 16.5 g of N-isopropylmaleimide (40%).

A stirred ice-cold solution of N-isopropylmaleimide (16.4 g, 0.118 mole) in carbon tetrachloride (12 mL) under nitrogen was treated dropwise with bromine (6.41 mL, 0.25 mole) at a rate to keep the pot temp <9° C., then stirred at 3° C. for 2 h, during which time the mixture formed a solid cake. The cake was maintained under a stream of nitrogen to allow excess bromine and CCl$_4$ to evaporate, then the reaction mixture was placed under vacuum to remove the remaining solvent. Ethanol (100 mL) was added to the flask, followed by sodium acetate (11 g, 0.134 mole), and the mixture was refluxed for 16 h with stirring. The cooled solution was filtered through Celite® (filter cake rinsed with methylene chloride), and the filtrate concentrated in vacuo, dissolved in methylene chloride, filtered through a pad of alumina (eluted with methylene chloride), and re-concentrated in vacuo. The residue was dissolved in 2:1 petroleum ether/methylene chloride, loaded onto a column of silica gel, and eluted successively with 2:1 petroleum ethers/CH$_2$Cl$_2$, 1:1 petroleum ethers/CH$_2$Cl$_2$, and CH$_2$Cl$_2$ alone to afford the subject compound (16.45 g, 64% yield) as a pale yellow, low melting solid. No MS (M+1) peak observed. $^1$H NMR (CDCl$_3$) δ 6.78 (s, 1H), 4.30-4.40 (m, 1H), 1.37 (d, 6H, J=8 Hz).

B. Synthesis of 1-(quinolin-3-yl)-3-isopropyl-3-azabicyclo[3.1.0]hexane, hydrochloride

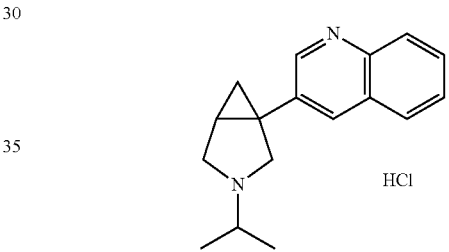

A stirred solution/suspension of 3-bromo-1-methylethylmaleimide (0.7 g, 3.43 mmol) and 3-quinoline boronic acid (1.2 g, 5.9 mmol) in dioxane (15 mL) under nitrogen was degassed with a stream of nitrogen for 10 min, treated with cesium fluoride (1.6 g, 10.8 mmol) and Cl$_2$Pd(dppf).CH$_2$Cl$_2$ (0.25 g, 0.3 mmol) then stirred at room temperature for 0.5 h and at 45° C. for 30 min then at 65° C. for 45 min. The mixture was cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride 60% and ethyl acetate 40%) to afford a tan solid, which was triturated from cold petroleum ethers to afford arylmaleimide intermediate (120 mg, 30%) as a tan solid.

A stirred suspension of trimethyl-sulfoxonium chloride (0.062 g, 0.48 mmol) under nitrogen was treated with 2.5M n-butyl lithium (0.19 mL, 0.48 mmol) in anhydrous tetrahydrofuran (30 mL), then refluxed for 2.5 h and cooled (50° C.). The above arylmaleimide (115 mg, 0.43 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual solid was dissolved in 1:1 methylene chloride/heptane and loaded onto a silica gel column and eluted with 1:1, 2:1, then 3:1 methylene chloride/heptane to afford the bicyclic diimide intermediate (75 mg, 62%) as a very pale yellow oil. ¹H NMR (CDCl₃) G 1.31-1.43 (m, 6H) 1.80-1.91 (m, 2H) 2.87 (dd, J=7.61, 4.30 Hz, 1H) 4.17-4.37 (m, 1H) 7.51-7.62 (m, 1H) 7.68-7.77 (m, 1H) 7.81 (d, J=8.00 Hz, 1H) 8.11 (d, J=8.59 Hz, 1H) 8.25 (d, J=1.95 Hz, 1 H) 8.89 (d, J=1.17 Hz, 1H).

A stirred ice-cooled solution of 2.0N LAH/THF (0.58 mL, 1.1 mmol) under nitrogen was treated dropwise with a solution of the above bicyclic diimide intermediate (72 mg, 0.27 mmol) in anhydrous THF (10 mL). The solution was stirred at room temperature for 15 min, refluxed for 4 h, cooled on an ice bath, and carefully treated dropwise with 30% NaOH (0.5 mL, vigorous evolution of gas). The solution was filtered and the filtrate was reduced to a clear oil. The residue was dissolved in methanol (23 mL), treated with 4N HCl/dioxane (7 mL), then stirred at room temperature for 3 h. The solution was concentrated in vacuo and the residue triturated from ether to afford 1-(quinolin-3-yl)-3-(2-propyl)-3-azabicyclo[3.1.0]hexane, hydrochloride (50 mg, 65%) as a white solid. MS (M+1) 253. ¹H NMR (CD₃OD) δ 1.37-1.45 (m, 1H) 1.49 (d, =5.94 Hz, 6H) 1.59 (t, J=7.73 Hz, 1H) 1.81 (dd, J=6.74, 4.76 Hz, 1H) 2.46-2.60 (m, 1H) 3.79-3.87 (m, 1H) 3.88-3.95 (m, 2H) 4.26 (d, 11.10 Hz, 1H) 7.99 (t, =7.73 Hz, 1H) 8.16 (t, J=7.33 Hz, 1H) 8.26 (d, J=8.32 Hz, 1H) 8.33 (d, J=8.32 Hz, 1H) 9.22 (s, 1H) 9.37 (d, J=1.98 Hz, 1H). ¹³C NMR (CD₃OD) δ 16.44, 19.42, 25.07, 29.93, 55.59, 57.94, 61.11, 121.95, 129.64, 131.44, 135.91, 138.94, 146.66.

C. Synthesis of 1-(1-methyl-1H-indol-5-yl)-3-isopropyl-3-azabicyclo[3.1.0]hexane, hydrochloride

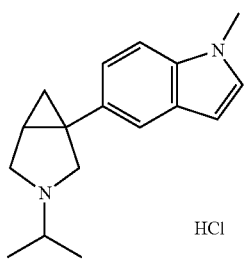 [SMILES: CC(C)N1CC2CC2(c2ccc3c(ccn3C)c2)C1 ; Cl]

A stirred solution/suspension of 3-bromo-1-methylethyl-maleimide (0.7 g, 3.43 mmol) and 5-quinoline-boronic acid (1.2 g, 5.9 mmol) in dioxane (15 mL) under nitrogen was degassed with a stream of nitrogen for 10 min, treated with cesium fluoride (1.6 g, 10.8 mmol) and Cl₂Pd(dppf).CH₂Cl₂ (0.25 g, 0.3 mmol) then stirred at room temperature for 0.5 h and at 45° C. for 30 min then at 65° C. for 45 min. The mixture was cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride 60% and ethyl acetate 40%) to afford a tan solid, which was triturated from cold petroleum ethers to afford arylmaleimide intermediate (430 mg, 30%) as a tan solid.

A stirred suspension of trimethylsulfoxonium chloride (0.290 g, 2.28 mmol) under nitrogen was treated with 2.5M n-butyllithium (0.95 mL, 2.18 mmol) in anhydrous tetrahydrofuran (30 mL), then refluxed for 2.5 h and cooled (50° C.). The above arylmaleimide (530 mg, 1.98 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO₄), and concentrated in vacuo. The residual solid was dissolved in 1:1 methylene chloride/heptane and loaded onto a silica gel column and eluted with 1:1, 2:1, then 3:1 methylene chloride/heptane to afford bicyclic diimide intermediate (120 mg, 21%) as a very pale yellow oil. ¹H NMR (CDCl₃) δ 1.22-1.39 (m, 6H) 1.73 (dd, J=4.21, 3.48 Hz, 1H) 1.83 (dd, J=8.14, 4.30 Hz, 1H) 2.67 (dd, J=8.05, 3.48 Hz, 1H) 3.79 (s, 3H) 4.14-4.31 (m, 1H) 6.43-6.47 (m, 1H) 7.04-7.08 (m, 1H) 7.23-7.27 (m, 1H) 7.28-7.35 (m, 1H) 7.63 (d, J=1.10 Hz, 1H).

A stirred ice-cooled solution of 2.0N LAH/THF (0.820 mL, 1.6 mmol) under nitrogen was treated dropwise with a solution of the above bicyclic diimide intermediate (116 mg, 0.41 mmol) in anhydrous THF (10 mL). The solution was stirred at room temperature for 15 min, refluxed for 4 h, cooled on an ice bath, and carefully treated dropwise with 30% NaOH (0.5 mL, vigorous evolution of gas). The solution was filtered and the filtrate was reduced to a clear oil. The residue was dissolved in methanol (23 mL), treated with 4N HCl/dioxane (7 mL), then stirred at room temperature for 3 h. The solution was concentrated in vacuo and the residue triturated from ether to afford 1-(1-methyl-1H-indol-5-yl)-3-(2-propyl)-3-azabicyclo[3.1.0]-hexane, hydrochloride (60 mg, 62%) as a white solid. MS (M+1) 255. ¹H NMR (CDCl₃) δ 1.10-1.20 (m, 1H) 1.51 (t, J=6.54 Hz, 6H) 1.89-2.00 (m, 1H) 2.29 (dd, J=6.44, 4.49 Hz, 1H) 3.17-3.40 (m, 3H) 3.74-3.79 (m, 3H) 3.86 (dd, J=10.84, 5.56 Hz, 1H) 4.06 (dd, J=10.93, 5.47 Hz, 1H) 6.41 (d, J=3.12 Hz, 1H) 7.00-7.10 (m, 2H) 7.21-7.29 (m, 1H) 7.46 (d, J=1.37 Hz, 1H). ¹³C NMR (CDCl₃) δ 15.95, 18.97, 22.62, 31.96, 33.16, 54.32, 58.59, 59.54, 109.88, 120.14, 121.45, 128.84, 129.06, 130.15, 136.18.

D. Synthesis of 1-(1-Methyl-2-indolyl)-3-isopropyl-3-azabicyclo[3.1.0]hexane, hydrochloride

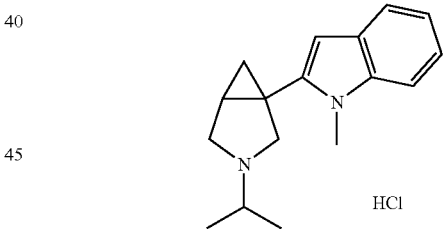

A stirred solution/suspension of 3-bromo-1-(1-methylethyl)maleimide (1.09 g, 5 mmol) and (1-methylindol-2-yl) tributyltin (2.63 g, 6.25 mmol) in dioxane (30 mL) under nitrogen was degassed with a stream of nitrogen for 10 min, then treated with cesium fluoride (1.8 g, 11.8 mmol) and Cl₂Pd(PPh₃)₂ (0.21 g, 0.3 mmol), stirred at room temperature for 30 min, 40° C. for 30 min, and 60° C. for 1.5 h. The mixture was cooled to room temperature, taken up in methylene chloride (100 mL), and filtered through Celite® (rinse filter cake with methylene chloride) and the filtrate concentrated in vacuo. The residue was dissolved in methylene chloride and filtered through a column of silica gel (eluted with methylene chloride) to afford a dark solid, which was triturated from ether to afford the arylmaleimide intermediate (1.236 g, 92%) as a yellow solid. MS (M+1) 269.2. ¹H NMR (CDCl₃) δ 7.69 (m, 1H), 7.59 (s, 1H), 7.34 (m, 2H), 7.14 (m, 1H), 6.52 (s, 1H), 4.44 (m, 1H), 3.87 (s, 3H), 1.46 (d, 6H, J=7 Hz).

A stirred suspension of sodium hydride oil dispersion (60%, 160 mg, 4.0 mmol) in anhydrous tetrahydrofuran (35 mL) under nitrogen was treated with trimethylsulfoxonium chloride (0.643 g, 5.0 mmol), then refluxed for 2.5 h and cooled (50° C.). The above arylmaleimide (1.073 g, 4.0 mmol) was added in one portion and the mixture stirred at 50° C. for 3 h, cooled on an ice bath, and quenched with saturated ammonium chloride (12 mL). The product mixture was extracted with ether (2×50 mL), and the combined extracts washed with water (35 mL), dried (MgSO$_4$), and concentrated in vacuo. The residue was dissolved in methylene chloride and loaded onto a silica gel column and eluted with methylene chloride to afford the bicyclic diimide intermediate (640 mg, 57%) as a pale orange solid. MS (M+1) 283.1. $^1$H NMR (CDCl$_3$) δ 7.56 (m, 1H), 7.32 (m, 1H), 7.20-7.27 (m, 2H), 7.10 (m, 1H), 4.28 (m, 1H), 3.80 (s, 3H), 2.72 (m, 1H), 1.87 (m, 2H), 1.37 (m, 6H).

A stirred cooled (5° C.) mixture of 2.0N lithium aluminum hydride/THF (5.2 mL, 10.4 mmol) in a 3-neck 100 mL round bottom flask under nitrogen was treated dropwise with a solution of the above bicyclic diimide intermediate (0.367 g, 1.30 mmol) in anhydrous THF (5 mL), and the mixture was stirred 1 h at room temperature and 3 h at reflux, then recooled on an ice bath. Water (0.4 mL), 15% sodium hydroxide (0.4 mL), and water (1.2 mL) were carefully added dropwise, and the mixture was stirred for a few minutes and filtered (rinse filter cake with methylene chloride). The filtrate was concentrated in vacuo and the residue dissolved in methylene chloride and loaded onto a silica gel column and eluted with 5% (9:1 ethanol/ammonia)/methylene chloride, then 10% (9:1 ethanol/ammonia)/methylene chloride to afford the free base of the title compound as a colorless oil. This was dissolved in ether (15 mL) and treated with 2.0N HCl/ether (1.25 mL, 2.5 mmol), the suspension diluted with a few mL of methylene chloride, stirred a few minutes, and the solid filtered, collected and dried in vacuo to afford 1-(1-methyl-2-indolyl)-3-(2-propyl)-3-azabicyclo[3.1.0]hexane, hydrochloride (321 mg, 85%) as a white solid. MS (M+1) 255.2. $^1$H NMR (CDCl$_3$) δ 7.52 (d, 1H, J=8 Hz), 7.20-7.30 (m, 2H), 7.09 (m, 1H), 6.35 (br s, 1H), 4.08 (m, 1H), 3.91 (m, 1H), 3.79 (s, 3H), 3.41 (m, 1H), 3.30 (m, 1H), 3.15 (m, 1H), 2.52 (m, 1H), 2.13 (m, 1H), 1.52 (m, 6H), 1.14 (m, 1H). $^{13}$C NMR (CDCl$_3$) δ 137.93, 136.96, 127.22, 122.49, 120.76, 120.30, 109.43, 101.26, 59.71, 57.36, 53.55, 30.77, 24.43, 22.61, 18.97, 15.36.

E. Synthesis of 1-(quinolin-5-yl)-3-isopropyl-3-azabicyclo[3.1.0]hexane, hydrochloride

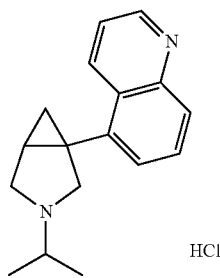 [SMILES: CC(C)N1CC2CC2(c2cccc3ncccc23)C1 ; Cl]

A stirred solution/suspension of 3-bromo-1-methylethylmaleimide (0.7 g, 3.43 mmol) and 5-quinolineboronic acid (1.2 g, 5.9 mmol) in dioxane (15 mL) under nitrogen was degassed with a stream of nitrogen for 10 min, treated with cesium fluoride (1.6 g, 10.8 mmol) and Cl$_2$Pd(dppf).CH$_2$Cl$_2$ (0.25 g, 0.3 mmol) then stirred at room temperature for 0.5 h and at 45° C. for 30 min then at 65° C. for 45 min. The mixture was cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride 60% and ethyl acetate 40%) to afford a tan solid, which was triturated from cold petroleum ethers to afford the arylmaleimide intermediate (430 mg, 30%) as a tan solid.

A stirred suspension of trimethylsulfoxonium chloride (0.062 g, 0.48 mmol) under nitrogen was treated with 2.5M n-butyllithium (0.19 mL, 0.48 mmol) in anhydrous tetrahydrofuran (30 mL), then refluxed for 2.5 h and cooled (50° C.). The above arylmaleimide (115 mg, 0.43 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual solid was dissolved in 1:1 methylene chloride/heptane and loaded onto a silica gel column and eluted with 1:1, 2:1, then 3:1 methylene chloride/heptane to afford the bicyclic diimide intermediate (75 mg, 62%) as a very pale yellow oil. $^1$H NMR (CDCl$_3$) δ 1.31-1.43 (m, 6H) 1.80-1.91 (m, 2H) 2.87 (dd, J=7.61, 4.30 Hz, 1H) 4.17-4.37 (m, 1H) 7.51-7.62 (m, 1H) 7.68-7.77 (m, 1H) 7.81 (d, J=8.00 Hz, 1H) 8.11 (d, J=8.59 Hz, 1H) 8.25 (d, J=1.95 Hz, 1H) 8.89 (d, J=1.17 Hz, 1H).

A stirred ice-cooled solution of 2.0N LAH/THF (0.58 mL, 1.1 mmol) under nitrogen was treated dropwise with a solution of the above bicyclic diimide intermediate (68 mg, 0.24 mmol) in anhydrous THF (10 mL). The solution was stirred at room temperature for 15 min, refluxed for 4 h, cooled on an ice bath, and carefully treated dropwise with 30% NaOH (0.5 mL, vigorous evolution of gas). The solution was filtered and the filtrate was reduced to a clear oil. The residue was dissolved in methanol (23 mL), treated with 4N HCl/dioxane (7 mL), then stirred at room temperature for 3 h. The solution was concentrated in vacuo and the residue triturated from ether to afford 1-(quinolin-5-yl)-3-(2-propyl)-3-azabicyclo[3.1.0]hexane, hydrochloride (50 mg, 75%) as a white solid. MS (M+1) 254. $^1$H NMR (CD$_3$OD) δ 1.37-1.45 (m, 1H) 1.49 (d, 0.1-5.94 Hz, 6H) 1.59 (t, J=7.73 Hz, 1H) 1.81 (dd, J=6.74, 4.76 Hz, 1H) 2.46-2.60 (m, 1H) 3.79-3.87 (m, 1H) 3.88-3.95 (m, 2H) 4.26 (d, J=11.10 Hz, 1H) 7.99 (t, J=7.73 Hz, 1H) 8.16 (t, J=7.33 Hz, 1H) 8.26 (d, J=8.32 Hz, 1H) 8.33 (d, J=8.32 Hz, 1H) 9.22 (s, 1H) 9.37 (d, J=1.98 Hz, 1H). $^{13}$C NMR (CD$_3$OD) δ 15.24, 18.91, 22.07, 29.31, 29.63, 54.20, 57.34, 60.05, 121.83, 122.56, 129.41, 131.70, 135.21, 136.73, 138.52, 143.76, 144.49.

Example V

Preparation of 1-heteroaryl-3-azabicyclo[3.1.0]hexanes using Reaction Scheme 3

A. Synthesis of 1-(benzothiophene-2-yl)-3-azabicyclo[3.1.0]hexane hydrochloride

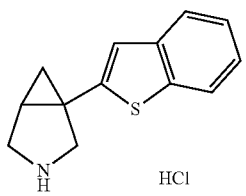

A stirred solution of 3-bromo-1-(3,4-dimethoxybenzyl) maleimide (3.26 g, 10 mmol) and thionaphthene-2-boronic acid (2.13 g, 12 mmol) in dioxane (30 mL) was degassed under a stream of nitrogen for 10 minutes, then treated with cesium fluoride (4 g, 26 mmol) and $Cl_2Pd(dppf)CH_2Cl$ (0.5 g, 0.61 mmol), then stirred at room temperature for 1 hour and at 40° C. for 2 h. The mixture was cooled and diluted with methylene chloride, stirred a few minutes and filtered through celite. The filtrate was concentrated in vacuo and purified by silica gel chromatography using 2% ethyl acetate/methylene chloride as the eluting solvent to afford the arylmaleimide intermediate (3.3 g, 87.3%). $^1$H NMR ($CDCl_3$) δ 8.34-8.27 (m, 1H), 7.92-7.81 (m, 2H), 7.48-7.36 (m, 2H), 7.07-6.80 (m, 3H), 6.66-6.60 (m, 1H), 4.73-4.65 (m, 2H), 3.89 (s, 3H), 3.86 (s, 3H).

A cooled (−20° C.) stirred solution of trimethylsulfoxonium chloride (964 mg, 7.5 mmol) in anhydrous tetrahydrofuran (30 mL) under nitrogen was treated with n-butyllithium/hexane (2.5N, 2.4 mL, 6.0 mmol) and warmed to 50° C. over 30 minutes. A solution of the arylmaleimide intermediate (2 g, 5.4 mmol) in anhydrous tetrahydrofuran (20 mL) was warmed to 50° C. and added all at once. After 2 h at 50° C., the mixture was cooled on ice and quenched with saturated aqueous ammonium chloride (2 mL). The mixture was stirred at room temperature for 15 minutes, then it was added to methylene chloride (100 mL) and the organic solution was dried ($Na_2SO_4$) and concentrated in vacuo. The residue was dissolved in methylene chloride, loaded onto a silica gel column and eluted with 2% ethyl acetate/methylene chloride to afford the bicyclic diimide intermediate (702 mg, 33%). $^1$H NMR ($CDCl_3$) δ 7.80-7.76 (m, 1H), 7.73-7.69 (m, 1H), 7.37-7.30 (m, 3H), 6.94-6.89 (m, 2H), 6.81-6.77 (m, 1H), 4.54 (q, 2H), 3.86 (s, 3H), 3.84 (s, 3H), 2.88-2.84 (m, 1H), 1.96-1.92 (m, 1H), 1.87-1.83 (m, 1H).

A stirred, ice-cooled (2° C.) solution of 1N lithium aluminum hydride/THF (16 mL, 16 mmol) under nitrogen was treated dropwise with a solution of the above bicyclic diimide (1.014 g, 2.58 mmol) in anhydrous tetrahydrofuran (20 mL), stirred 3 h at room temperature and 1 h at reflux, then cooled on an ice bath. Water (0.60 mL), 15% NaOH (0.60 mL), and water (1.80 mL) were added dropwise together with more tetrahydrofuran to facilitate stirring. The mixture was stirred at room temperature for 15 minutes, filtered through celite and the filtrate concentrated in vacuo. The residue was dissolved in methylene chloride, loaded onto a silica gel column, and eluted with 3:1 methylene chloride/ethyl acetate to afford the bicyclic intermediate (754 mg, 80%). $^1$H NMR ($CDCl_3$) δ 7.74-7.59 (m, 2H), 7.31-7.19 (m, 2H), 6.99-6.97 (m, 1H), 6.90-6.78 (m, 3H), 3.90 (s, 3H), 3.85 (s, 3H), 3.65-3.60 (m, 2H), 3.30 (d, 1H), 3.05 (d, 1H), 2.75 (d, 1H), 2.60-2.54 (m, 1H), 1.77-1.71 (m, 1H), 1.68-1.62 (m, 1H), 1.08-1.03 (m, 1H).

A solution of the above bicyclic intermediate (365 mg, 1 mmol) and anhydrous potassium carbonate (276 mg, 2 mmol) in anhydrous methylene chloride (6 mL) in a pressure tube was treated with 1-chloroethyl chloroformate (0.3 mL, 3 mmol). The tube was closed under nitrogen flow, stirred at 40° C. for 4 h, then cooled and uncapped. The contents were filtered and the filtrate concentrated in vacuo, dissolved in methanol (12 mL), refluxed for 1 h, then cooled to room temperature and treated with DOWEX 550A-OH. The mixture was filtered and the filtrate concentrated in vacuo to debenzylated free base of 1-(benzothiophen-2-yl)-3-azabicyclo[3.1.0]hexane (120 mg, 56%). 45 mg of compound was converted to the hydrochloride salt by treating with 2N HCl/ether. MS (M+1) 215.8. $^1$H NMR (MeOH-$d_4$) δ 7.82-7.67 (m, 2H), 7.36-7.23 (m, 3H), 3.85-3.66 (m, 3H), 3.57-3.49 (m, 1H), 3.32-3.27 (m, 1H), 2.24-2.17 (m, 1H), 1.54-1.47 (m, 1H), 1.37-1.31 (m, 1H). $^{13}$C NMR (MeOD-$d_4$) δ 142.58, 140.10, 138.95, 124.52, 124.35, 123.14, 121.95, 121.76, 50.52, 47.69, 28.06, 25.82, 16.16.

B. Synthesis of 1-(benzothiophen-2-yl)-3-methyl-3-azabicyclo[3.1.0]hexane hydrochloride

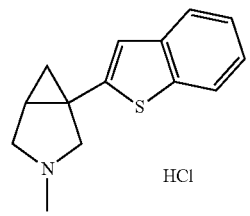 [SMILES: CN1CC2CC2(c2cc3ccccc3s2)C1 ; Cl]

A stirred solution of 1-(benzothiophen-2-yl)-3-azabicyclo[3.1.0]hexane (72 mg, 0.348 mmol) in 1,2-dichloroethane (7 ml) was treated with 37% formaldehyde (0.21 mL, 2.8 mmol), then with sodium triacetoxyborohydride (294.5 mg, 1.39 mmol) and this reaction mixture was stirred at room temperature for 3 h. 1N sodium hydroxide (7 mL) was then added, stirring continued for a few minutes, and the organic layer was separated. The aqueous layer was washed with methylene chloride, and the organic layers were combined, washed with brine, dried ($Na_2SO_4$), filtered and concentrated in vacuo. The residue was chromatographed on a silica gel column (eluted with 90:9:1 methylene chloride/ethanol/ammonia). The oily 1-(benzothiophen-2-yl)-3-methyl-3-aza-bicyclo[3.1.0]hexane (71.6 mg, 90%) was converted to the hydrochloride salt by treating with 2N HCl/ether (49 mg, 53%). MS (M+1) 229.79. $^1$H NMR (MeOD-$d_4$) δ 7.84-7.66 (m, 2H), 7.39-7.23 (m, 3H), 4.11-4.02 (m, 1H), 3.85-3.71 (m, 2H), 3.68-3.60 (m, 1H), 3.07-2.97 (s, 3H), 2.31-2.21 (m, 1H), 1.56-1.44 (m, 2H). $^{13}$C NMR (METHANOL-$d_4$) δ 142.20, 140.06, 138.95, 124.56, 124.41, 123.18, 121.96, 121.92, 59.69, 57.19, 40.00, 27.81, 25.6, 16.21.

C. Synthesis of 1-(quinolin-5-yl)-3-azabicyclo[3.1.0]hexane, hydrochloride

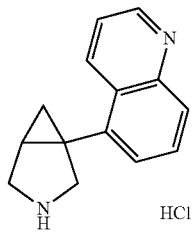 [SMILES: c1cc(C23CNCC2C3)c2cccnc2c1 ; Cl]

A stirred solution/suspension of 3-bromo-1-(3,4-dimethoxybenzyl)maleimide (3.8 g, 11.57 mmol) and quinoline-5-boronic acid (2 g, 11.56 mmol) in dioxane (15 mL) under nitrogen was degassed with a stream of nitrogen for 10 min, treated with cesium fluoride (3.8 g, 25.4 mmol) and $Cl_2Pd(dppf).CH_2Cl_2$ (0.50 g, 0.6 mmol), then stirred at room temperature for 0.5 h and at 45° C. for 30 min then at 65° C. for 45 min. The mixture was cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride 60% and ethyl acetate 40%) to afford a pale yellow solid, which was triturated from cold petroleum ethers to afford the arylmaleimide intermediate (3.3 g, 77%) as pale yellow solid.

A cooled (–20° C.) stirred solution of trimethylsulfoxonium chloride (1.25 g, 9.7 mmol) in anhydrous tetrahydrofuran (15 mL) under nitrogen was treated dropwise with n-butyllithium/hexane (2.4N, 3.9 mL, 9.73 mmol) and gradually warmed to 50° C. over 30 minutes. Meanwhile, a solution of the intermediate arylmaleimide (3.3 g, 8.8 mmol) in anhydrous THF (10 mL) was heated to 50° C., then added quickly in one portion to the above heated suspension, and the mixture was stirred at 50° C. for 2 h, then cooled on an ice bath. Saturated aqueous ammonium chloride (1 mL) was added to quench, and the mixture was diluted with methylene chloride (75 mL), dried ($MgSO_4$), filtered through Celite® (rinse with methylene chloride), and concentrated in vacuo. The residue was dissolved in methylene chloride, loaded onto a silica gel column, and the product eluted with 3% ethyl acetate/methylene chloride to afford the intermediate bicyclic diimide (300 mg, 10%) as a very pale yellow viscous oil.

A cooled (5° C.) stirred solution of 1N lithium aluminum hydride/THF (3.1 mL, 3.1 mmol) under nitrogen was treated slowly with a solution of the above intermediate bicyclic diimide (300 mg, 0.77 mmol) in anhydrous THF (7 mL), stirred 1 h at room temperature, refluxed for 6 h, and cooled (5° C.). Water (0.4 mL), 15% sodium hydroxide (0.4 mL), and water (1.2 mL) were carefully added dropwise, followed by additional THF to facilitate stirring. The suspension was stirred 15 min, filtered through Celite® (filter cake rinsed with THF), and the filtrate concentrated in vacuo. The residue was dissolved in methylene chloride, loaded onto a silica gel column, and eluted with 3:1 methylene chloride/ethyl acetate to afford the intermediate dimethoxybenzyl bicyclic amine (110 mg, 40%) as a colorless viscous oil.

A mixture of the intermediate dimethoxybenzyl bicyclic amine (100 mg, 0.3 mmol) and anhydrous potassium carbonate (83 mg, 0.6 mmol) in anhydrous methylene chloride (5 mL) in a pressure tube equipped with a stirbar was treated with 1-chloroethyl chloroformate (0.130 mL, 0.9 mmol), closed, and stirred at 45° C. for 4 h. The tube was cooled, opened, and the contents filtered (rinse with methylene chloride), and the filtrate concentrated in vacuo. The residue was dissolved in methanol (7 mL), refluxed for h, cooled, treated with DOWEX® 550A-OH resin (2.0 g, prerinsed with methanol), stirred a few minutes, filtered, and the filtrate concentrated in vacuo. The residue was taken up in ether, filtered through Celite®, and the filtrate treated with 2N HCl/ether (0.6 mL, 1.2 mmol). The suspension was stirred a few minutes, the solid salt collected by filtration, rinsed with ether, and dried in vacuo to afford 1-(quinolin-5-yl)-3-azabicyclo[3.1.0]-hexane, hydrochloride (70 mg, 47%) as a light beige solid. MS (M+1) 225.1. $^1H$ NMR (DMSO-$d_6$) δ 9.33 (s, 1H), 8.94 (s, 1H), 8.36 (d, 1H, J=8.5 Hz), 8.17 (d, 1H, J=8 Hz), 8.01 (t, 1H, J=7.5 Hz), 7.86 (t, 1H, J=7.5 Hz), 3.97 (dd, 1H, J=11 Hz, 5 Hz), 3.42-3.86 (m, 3H), 2.24-2.43 (m, 1H), 1.74-2.14 (m, 1H), 1.44 (t, 1H, J=7.5 Hz). $^{13}C$ NMR (DMSO-$d_6$) δ 147.12, 142.14, 134.04, 133.52, 129.91, 129.10, 128.57, 123.24, 58.85, 56.63, 29.36, 24.70, 15.32.

D. Synthesis of 1-(quinolin-3-yl)-3-azabicyclo[3.1.0]hexane, hydrochloride

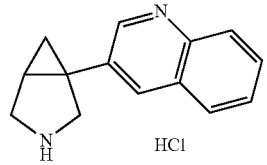 [SMILES: c1ccc2ncc(C34CNCC3C4)cc2c1 ; Cl]

A stirred solution of 3-bromo-1-(3,4-dimethoxybenzyl) maleimide (1.0 g, 3.06 mmol) and quinoline-3-boronic acid (0.52 g, 3.4 mmol) in anhydrous dioxane (10 mL) under nitrogen was degassed over 10 min with a stream of nitrogen, then treated with cesium fluoride (1.3 g, 8.5 mmol) and $Cl_2Pd$ (dppf).$CH_2Cl_2$ (Aldrich, 0.17 g, 0.21 mmol), stirred 1 h at room temperature, then 2 h at 40° C. The mixture was cooled, diluted with methylene chloride (50 mL), stirred a few minutes, filtered through Celite® (rinse with methylene chloride), and the filtrate concentrated in vacuo. The residue was dissolved in methylene chloride and loaded onto a silica gel column and the product eluted with 3% ethyl acetate/methylene chloride to afford a yellow solid, which was triturated from petroleum ethers to afford the intermediate arylmaleimide (940 g, 79%) as a pale yellow solid.

A cooled (–20° C.) stirred solution of trimethylsulfoxonium chloride (370 mg, 2.86 mmol) in anhydrous tetrahydrofuran (15 mL) under nitrogen was treated dropwise with n-butyllithium/hexane (2.4N, 1.1 mL, 2.03 mmol) and gradually warmed to 50° C. over 30 minutes. Meanwhile, a solution of the intermediate arylmaleimide (0.94 g, 2.6 mmol) in anhydrous THF (10 mL) was heated to 50° C., then added quickly in one portion to the above heated suspension, and the mixture was stirred at 50° C. for 2 h, then cooled on an ice bath. Saturated aqueous ammonium chloride (1 mL) was added to quench, and the mixture was diluted with methylene chloride (75 mL), dried ($MgSO_4$), filtered through Celite® (rinse with methylene chloride), and concentrated in vacuo. The residue was dissolved in methylene chloride, loaded onto a silica gel column, and the product eluted with 3% ethyl acetate/methylene chloride to afford the intermediate bicyclic diimide (400 mg, 50%) as a very pale yellow viscous oil.

A cooled (5° C.) stirred solution of 1N lithium aluminum hydride/THF (3.6 mL, 10 mmol) under nitrogen was treated slowly with a solution of the above intermediate bicyclic diimide (400 mg, 1.2 mmol) in anhydrous THF (7 mL), stirred 1 h at room temperature, refluxed for 6 h, and cooled (5° C.). Water (0.4 mL), 15% sodium hydroxide (0.4 mL), and water (1.2 mL) were carefully added dropwise, followed by additional THF to facilitate stirring. The suspension was stirred 15 min, filtered through Celite® (filter cake rinsed with THF), and the filtrate concentrated in vacuo. The residue was dissolved in methylene chloride, loaded onto a silica gel column, and eluted with 3:1 methylene chloride/ethyl acetate to afford the intermediate dimethoxybenzyl bicyclic amine (280 mg, 58%) as a colorless viscous oil.

A mixture of the intermediate dimethoxybenzyl bicyclic amine (280 mg, 0.76 mmol) and anhydrous potassium carbonate (215 mg, 1.55 mmol) in anhydrous methylene chloride (5 mL) in a pressure tube equipped with a stirbar was treated with 1-chloroethyl chloroformate (0.221 mL, 1.55 mmol), closed, and stirred at 45° C. for 4 h. The tube was cooled, opened, and the contents filtered (rinse with methylene chloride), and the filtrate concentrated in vacuo. The residue was dissolved in methanol (7 mL), refluxed for 1 h, cooled, treated with DOWEX® 550A-OH resin (2.0 g, pre-rinsed with methanol), stirred a few minutes, filtered, and the filtrate concentrated in vacuo. The residue was taken up in ether, filtered through Celite®, and the filtrate treated with 2N HCl/ether (0.6 mL, 1.2 mmol). The suspension was stirred a few minutes, the solid salt collected by filtration, rinsed with ether, and dried in vacuo to afford 1-(quinolin-3-yl)-3-azabi-cyclo-[3.1.0]hexane, hydrochloride (100 mg, 47%) as a light beige solid. MS (M+1) 192.1. $^1$H NMR (DMSO-d$_6$) δ 9.33 (s, 1H), 8.94 (s, 1H), 8.36 (d, 1H, J=8.5 Hz), 8.17 (d, 1H, J=8 Hz), 8.01 (t, 1H, J=7.5 Hz), 7.86 (t, 1H, J=7.5 Hz), 3.97 (dd, 1H, J=11 Hz, 5 Hz), 3.42-3.86 (m, 3H), 2.24-2.43 (m, 1H), 1.74-2.14 (m, 1H) 1.44 (t, 1H, J=7.5 Hz). $^{13}$C NMR (DMSO-d$_6$) δ ppm 147.12, 142.14, 134.04, 133.52, 129.91, 129.10, 128.57, 123.24, 58.85, 56.63, 29.36, 24.70, 15.32.

Synthesis of 6-fluoro-benzo[b]thiophene-2-carboxylic acid ethyl ester

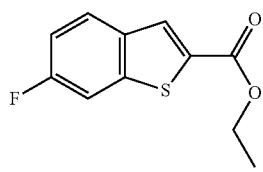

To a mixture of 2,5-difluorobenzaldehyde (280 g, 1.97 mol), potassium carbonate (272 g, 1.97 mol) and anhydrous DMF (1260 ml) was added mercaptoacetic acid ethyl ester (236 g, 1.97 mol). The mixture was stirred at 90° C. for 4 h. After cooling water (4200 ml) was added and the solution was extracted with ethyl acetate (3×1500 ml), the combined extracts dried over sodium sulfate and the solvent was removed to give crude product, which was flash-chromatographed (eluent-ethyl acetate (1):hexane (9). Yield of 6-fluoro-benzo[b]thiophene-2-carboxylic acid ethyl ester 96.49 g (21.8%) as a yellow solid. $^1$H-NMR (400 MHz, CDCl$_3$); δ (ppm): 1.40 (t, 3H), 4.40 (q, 2H), 7.15 (t, 1H), 7.52 (d, 1H), 7.81 (dd, 1H), 8.00 (s, 1H).

Synthesis of 6-fluoro-benzo[b]thiophen-2-yl)-methanol

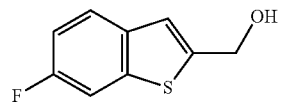 [SMILES: OCc1cc2ccc(F)cc2s1]

To a suspension of lithium aluminum hydride (15.5 g, 0.43 mol) in dry THF (600 ml) was added a solution of 6-fluoro-benzo[b]thiophene-2-carboxylic acid ethyl ester (96.49 g, 0.43 mol) in dry THF (960 ml), the mixture was stirred for 3 h at 20° C. The reaction was carefully quenched by the dropwise addition of water (15.5 ml), 15% NaOH (15.5 ml) and water (46.5 ml), stirred for 0.5 h, then filtered and washed with THF: water (1:1) (100 ml). The filtrate was concentrated to give 58.25 g (74%) of 6-fluoro-benzo[b]thiophen-2-yl)-methanol as white powder. $^1$H-NMR (400 MHz, DMSO-d6); δ (ppm): 4.67 (s, 2H), 5.51 (s, 1H), 7.17 (t, 1H), 7.22 (s, 1H), 7.72-7.80 (m, 2H).

Synthesis of 2-chloromethyl-6-fluoro-benzo[b]thiophene

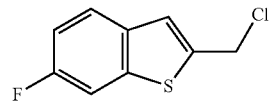 [SMILES: Fc1ccc2cc(CCl)sc2c1]

To a solution of 6-fluoro-benzo[b]thiophen-2-yl)-methanol (60.89 g, 0.33 mol) in dry dioxane (30 ml) was added thionyl chloride (39 ml, 0.53 mol) while keeping the temperature below 15° C. and stirred at for 4 hours (TLC control). The mixture was evaporated at 40° C. under reduced pressure to give 2-chloromethyl-6-fluoro-benzo[b]thiophene as white solid in essentially quantitative yield.

Synthesis of 6-fluoro-benzo[b]thiophen-2-yl)-acetonitrile

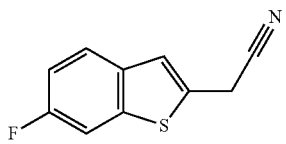 [SMILES: N#CCc1cc2ccc(F)cc2s1]

To a solution of NaCN (21.8 g, 0.446 mol) in DMSO (600 ml) was added portionwise 2-chloromethyl-6-fluoro-benzo [b]thiophene (71.5 g, 0.357 mol) while keeping the temperature below 15° C. and stirred for 1.5 h at 40-45° C. (TLC 7:3; Heptane:ethyl acetate), then diluted with cold water (2 L), which lead to the formation of a precipitate. The precipitate was filtered off, washed with water and dried in vacuo at 50° C. for 12 hours. The crude material was still very wet and dissolved in dichloromethane (1 L) and dried over magnesium sulfate. The crude product was isolated by removal of the solvent under reduced pressure, yielding 28.1 g (41%) of 6-fluorobenzo[b]thiophen-2-yl)-acetonitrile as a light yellow powder. ¹H-NMR (400 MHz, CDCl₃); δ (ppm): 3.95 (s, 2H), 7.11 (t, 1H), 7.26 (s, 1H), 7.45 (d, 1H), 7.67 (dd, 1H).

Synthesis of (1S,5S)-1-(6-fluoro-benzo[b]thiophen-2-yl)-3-aza-bicyclo[3.1.0]hexane hydrochloride
(scheme 4)

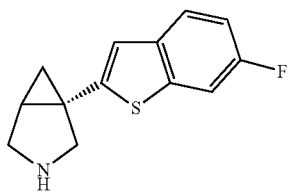 [SMILES: Fc1ccc2cc([C@]34CNCC3C4)sc2c1]

To a stirring solution of 6-fluoro-benzo[b]thiophen-2-yl)-acetonitrile (8 g, 0.0418 mol) in anhydrous THF (42 ml) at −30° C. under nitrogen was added 20.9 ml (0.0418 mmol) of NaHMDS (2M in THF) slowly while keeping the temperature below −20° C. The resulting mixture was stirred for 0.5 hr between −15° C. and −25° C. (S)-(+)-Epichlorohydrin (5.03 g, 0.0418 mol) was added at −25° C., the mixture was stirred between −15° C. and −25° C. for 0.5 h then NaHMDS (25.1 ml, 0.0502 mol) was added at −25° C. The mixture was stirred for 1 hr between −10° and −20° C., then for 2 hr between −10° and 5° C., quenched with 2N HCl (60 ml) and the layers were separated. The aqueous layer was re-extracted with EtOAc (1×50 ml). The organics were combined, washed with saturated NaCl (50 ml), dried over Na₂SO₄, filtered and concentrated to provide crude product as a brown oil.

The brown oil was dissolved in THF (42 ml) and 10 M borane dimethylsulfide (9.3 ml, 0.0836) was added dropwise via syringe. The mixture was heated to reflux for 2 hr. The mixture was cooled to <40° C. and quenched with 4N HCl (85 ml). The organic portion was separated and discarded. The aqueous portion was re-extracted with ethyl acetate (3×50 ml) and organic portion discarded. The aqueous portion was basified with ammonium hydroxide (35 ml) and then extracted with ethyl acetate (2×50 ml). The combined organic portion was washed with 5% sodium phosphate dibasic (1×50 ml) and brine (1×50 ml). The organic portion was dried over magnesium sulfate, filtered and concentrated under reduced pressure to a yellow oil (5.24 g). The oil was purified by column chromatography with dichloromethane (93): MeOH (6):NH₄OH (1) and the major product (cis isomer) was isolated (1S,2S)-[2-aminomethyl-2-(6-fluoro-benzo[b]thiophen-2-yl)-2-cyclopropyl]-methanol 2.13 g (20%) as an off white solid. MS m/z 252 (MH+).

The hydrochloride salt was prepared with [2-aminomethyl-2-(6-fluoro-benzo[b]thiophen-2-yl)-2-cyclopropyl]-methanol (170 mg) by dissolving in isopropanol (2 ml) and adding 5M isopropanolic HCl (2 ml) and blowing dry with nitrogen. The hydrochloride salt was dried in vacuo at 50° C. for 12 hours to yield (1S,2S)-[2-aminomethyl-2-(6-fluoro-benzo[b]thiophen-2-yl)-2-cyclopropyl]-methanol hydrochloride which was 98 8% pure by HPLC. MS m/z 252 (MH+). 1H NMR (400 MHz, DMSO-d₆) δ ppm 1.03 (d) 1.19-1.25 (m) 1.23 (t) 1.20-1.25 (m) 1.20-1.25 (m) 1.28 (dd) 1.59-1.70 (m) 3.20-3.39 (m) 3.42 (dd) 3.89 (dd) 7.23 (td) 7.77 (dd) 7.84 (dd) 8.07 (br. s.)

To a stirring solution of [2-aminomethyl-2-(6-fluoro-benzo[b]thiophen-2-yl)-2-cyclopropyl]-methanol (1.96 g, 7.8 mmol) in dry dioxane (130 ml) at 15° C. was added slowly thionyl chloride (1.88 ml, 25.7 mmol). After 2.5 hr at room temperature TLC (9:1; Dichloromethane:methanol) showed the reaction was complete. The mixture was evaporated at 40° C., dissolved in dichloromethane (200 ml) and stirred vigorously with aqueous sodium carbonate until LC/MS showed that the compound was completely cyclized (0.5 hr). The layers were separated and the organic portion dried over magnesium sulfate and concentrated under reduced pressure. The crude product was suspended in diethyl ether (100 ml), added 5M isopropanolic HCl (5 ml), and stirred for 30 min. The precipitate was filtered, washed with diethyl ether to give (1S,5S)-1-(6-fluoro-benzo[b]thiophen-2-yl)-3-aza-bicyclo[3.1.0]hexane hydrochloride as an off white solid. Yield 1.2 g (57%) and 100% pure by HPLC. Chiral Purity 100%. MS m/z 234 (MH+) ¹H-NMR (400 MHz, DMSO-d6); δ (ppm): 1.32 (t, 1H), 1.60 (t, 1H), 2.11 (m, 1H), 3.30-3.75 (m, 4H), 7.22 (t, 1H), 7.35 (s, 1H), 7.76 (dd, 1H), 7.82 (d, 1H), 9.80 (br. s, 2H). ¹³C NMR (101 MHz, DMSO-d₆) d ppm 16.39, 25.98, 27.63, 49.15, 108.49, 108.75, 113.23, 113.47, 120.88, 124.36, 124.45, 136.34, 138.91, 139.02, 143.63, 143.66, 158.38, 160.78.

Synthesis of (1R,5R)-1-(6-fluoro-benzo[b]thiophen-2-yl)-3-aza-bicyclo[3.1.0]hexane hydrochloride
(scheme 5)

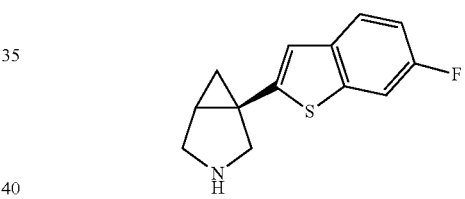

Procedure as described above except (R)-(−)-epichlorohydrin used.

(1R,2R)-[2-aminomethyl-2-(6-fluoro-benzo[b]thiophen-2-yl)-2-cyclopropyl]-methanol 2.13 g (20%) as an off white solid. MS m/z 252 (MH+). The hydrochloride salt was prepared with (1R,2R)-[2-aminomethyl-2-(6-fluoro-benzo[b]thiophen-2-yl)-2-cyclopropyl]-methanol (111 mg) by dissolving in isopropanol (2 ml) and adding 5M isopropanolic HCl (2 ml) and blowing dry with nitrogen. The hydrochloride salt was dried in vacuo at 50° C. for 12 hours to yield (1R,2R)-[2-aminomethyl-2-(6-fluoro-benzo[b]thiophen-2-yl)-2-cyclopropyl]-methanol hydrochloride which was 98.4% pure by HPLC. MS m/z 252 (MH+). 1H NMR (400 MHz, DMSO-d₆) δ ppm 1.03 (d) 1.19-1.25 (m) 1.23 (t) 1.20-1.25 (m) 1.20-1.25 (m) 1.28 (dd) 1.59-1.70 (m) 3.20-3.39 (m) 3.42 (dd) 3.89 (dd) 7.23 (td) 7.77 (dd) 7.84 (dd) 8.07 (br. s.)

(1R,5R)-1-(6-fluoro-benzo[b]thiophen-2-yl)-3-aza-bicyclo[3.1.0]hexane hydrochloride as an off white solid. Yield 1.0 g (48%) and 100% pure by HPLC. Chiral purity 99.6%. MS m/z 234 (MH+). ¹H-NMR (400 MHz, DMSO-d6); δ (ppm): 1.32 (t, 1H), 1.60 (t, 1H), 2.11 (m, 1H), 3.30-3.75 (m, 4H), 7.22 (t, 1H), 7.35 (s, 1H), 7.76 (dd, 1H), 7.82 (d, 1H), 9.80 (br. s, 2H). ¹³C NMR (101 MHz, DMSO-d₆) d ppm 16.39, 25.98, 27.63, 49.15, 108.49, 108.75, 113.23, 113.47, 120.88, 124.36, 124.45, 136.34, 138.91, 139.02, 143.63, 143.66, 158.38, 160.78.

1. Preparation of 6-bromo-benzo[b]thiophene-2-carboxylic acid ethyl ester

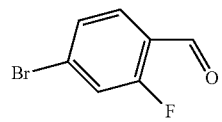

(a) Ethyl thioglycolate, Et$_3$N, DMSO, 95° C., 2 h

The substance was obtained according to the general procedure, yielding the title compound as a light yellow solid (70%).

$^1$H-NMR (400 MHz, DMSO-d$_6$); δ (ppm): 1.34 (t, 3H), 4.34 (dd, 2H), 7.62 (d, 1H), 7.96 (d, 1H), 7.18 (s, 1H), 7.37 (s, 1H)

2. Preparation of 5-bromo-benzo[b]thiophene-2-carboxylic acid ethyl ester

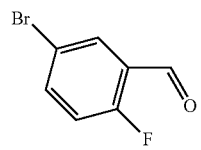

(a) Ethyl thioglycolate, Et$_3$N, DMSO, 95° C., 2 h

The substance was obtained according to the general procedure, yielding the title compound as a off-white crystals (75%).

$^1$H-NMR (400 MHz, DMSO-d$_6$); δ (ppm): 1.33 (t, 3H), 4.36 (dd, 2H), 7.63 (d, 1H), 8.04 (d, 1H), 7.13 (s, 1H), 7.25 (s, 1H)

3. Preparation of (6-bromo-benzo[b]thiophen-2-yl)-methanol

(a) tetrahydrofuran, LiBH$_4$, 60° C., 3 h

The substance was obtained according to the general procedure, yielding the title compound as a white solid (96%)

4. Preparation of (5-bromo-benzo[b]thiophen-2-yl)-methanol

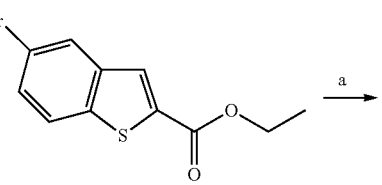

(a) Tetrahydrofuran, LiBH$_4$, 60° C., 3 h

The substance was obtained according to the general procedure, yielding the title compound as a white solid (73%)

5. Preparation of (6-bromo-benzo[b]thiophen-2-yl)-acetonitrile

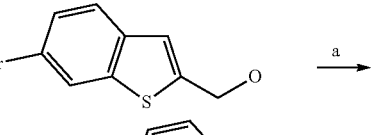

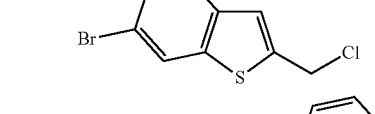

SOCl$_2$, dichloromethane, RT, 2 h
NaCN, acetonitrile, 18-crown-6, RT, overnight The substance was obtained according to the general procedure. Overall yield of (6-bromo-benzo[b]thiophen-2-yl)-acetonitrile (30% on three previous steps). Light yellow solid.

$^1$H-NMR (400 MHz, DMSO-d$_6$); δ (ppm): 4.39 (s, 2H), 7.4 (s, 1H), 7.53 (d, 1H), 7.78 (d, 1H), 8.23 (s, 1H)

6. Preparation of (S-bromo-benzo[b]thiophen-2-yl)-acetonitrile

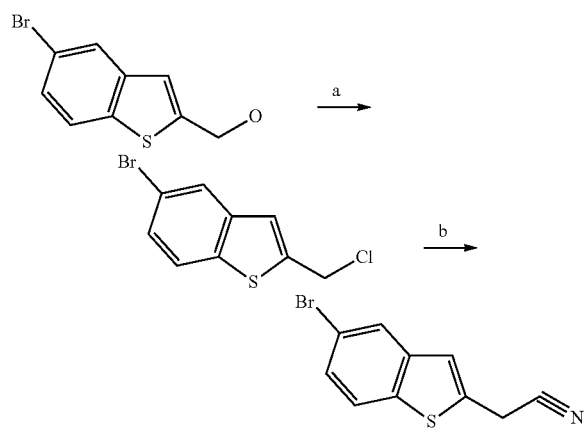

SOCl$_2$, dichloromethane, RT, 2 h
NaCN, acetonitrile, 18-crown-6, RT, overnight The substance was obtained according to the general procedure. Overall yield of (6-bromo-benzo[b]thiophen-2-yl)-acetonitrile (26% on three previous steps). Light yellow solid.

$^1$H-NMR (400 MHz, DMSO-d$_6$); δ (ppm): 4.43 (s, 2H), 7.39 (s, 1H), 7.48 (d, 1H), 7.9 (d, 1H), 8.06 (s, 1H)

7. Preparation of 1-(6-bromo-benzo[b]thiophen-2-yl)-2-hydroxymethyl-cyclopropanecarbonitrile and 5-(6-bromo-benzo[b]thiophen-2-yl)-3-oxa-bicyclo[3.1.0]hexan-2-one

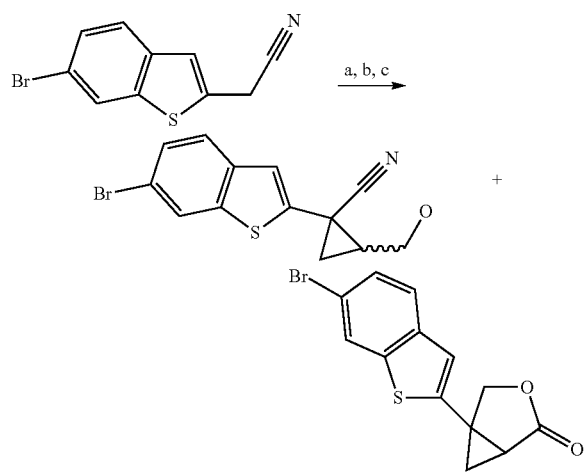

a) NaHMDS, THF, −20° C., 1 h
b) Epibromohydrin, −20° C., 1 h
c) NaHMDS, THF, from −20° C. to 5° C., overnight The substances were obtained according to the general procedure.

Yield of the lactone 17%. Light brown crystalline solid.
Yield of the nitrile 39%. Dark brown liquid.

8. Preparation of 1-(5-bromo-benzo[b]thiophen-2-yl)-2-hydroxymethyl-cyclopropanecarbonitrile and 5-(5-bromo-benzo[b]thiophen-2-yl)-3-oxa-bicyclo[3.1.0]hexan-2-one

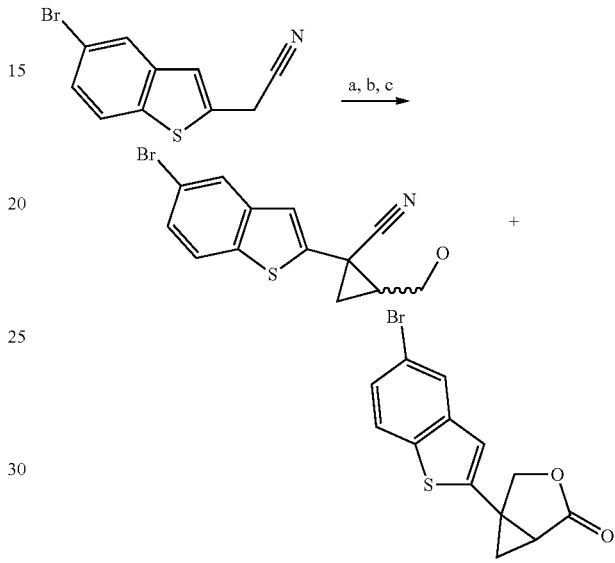

a) NaHMDS, THF, −20° C., 1 h
b) Epibromohydrin, −20° C., 1 h
c) NaHMDS, THF, from −20° C. to 5° C., overnight The substances were obtained according to the general procedure.

Yield of the lactone 20%. Light brown crystalline solid.
CI MS m/z 308.8, 310.78 (MH+).
Yield of the nitrile 37%. Dark brown liquid.
CI MS m/z 307.89, 309.86 (MH+).

9. Preparation of-2-aminomethyl-2-(6-bromo-benzo[b]thiophen-2-yl)-cyclopropyl]-methanol

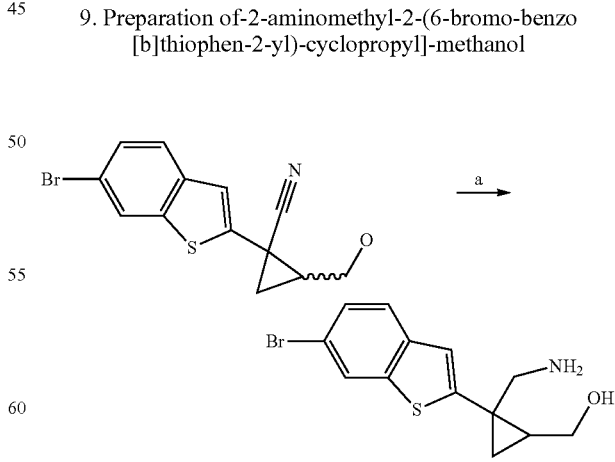

BH$_3$-THF complex, from RT to 50° C., 1.5 h

The substances were obtained according to the general procedure, yielding the title compound as a light yellow liquid (42%).

10. Preparation of 2-aminomethyl-2-(5-bromo-benzo[b]thiophen-2-yl)-cyclopropyl]-methanol Method A:

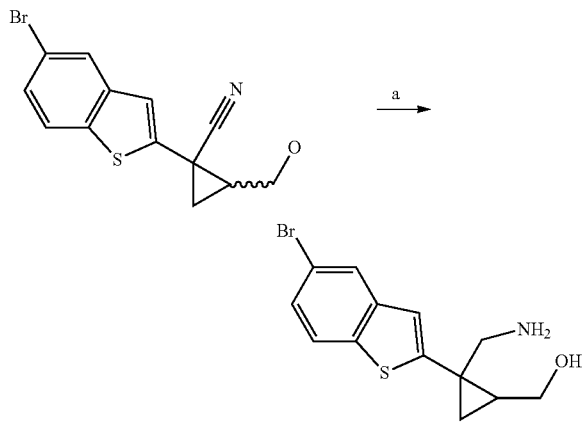

BH₃-THF complex, from RT to 50° C., 1.5 h

The substance was obtained according to the general procedure, yielding the title compound as a light yellow liquid (40%).

Method B:

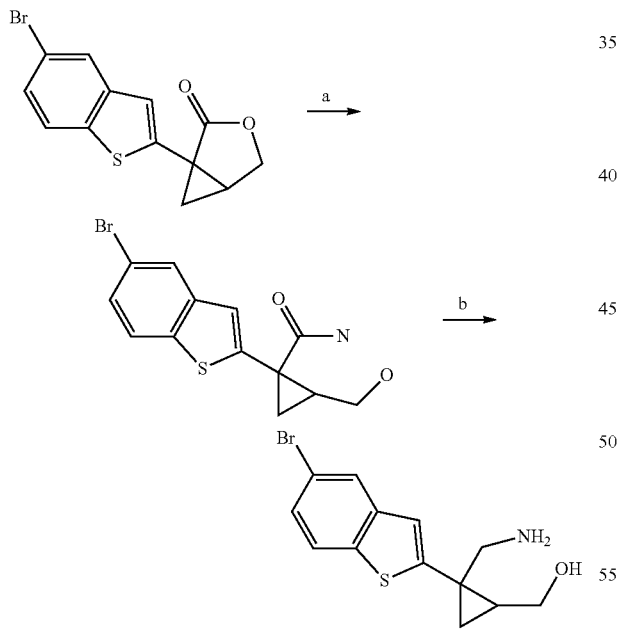

a) NH₃/MeOH, 50° C., 12 h
b) BH₃-THF complex, reflux, 8 h

The substance was obtained according to the general procedure.

Overall yield of the title compound 41%. A light yellow liquid

CI MS m/z 311.89, 313.87 (MH+).

11. Preparation of 1-(6-bromo-benzo[b]thiophen-2-yl)-3-aza-bicyclo[3.1.0]hexane

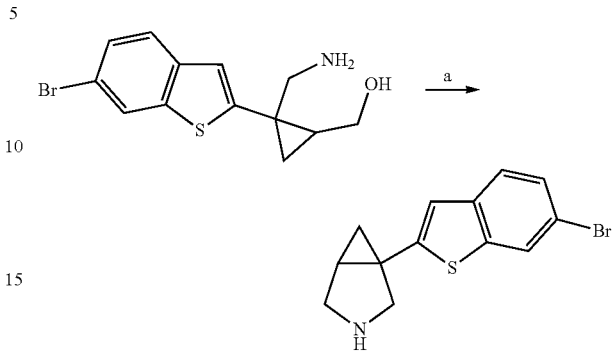

SOCl₂, dioxane, from 0° C. to RT, 1.5 h

The substance and its hydrochloride salt were obtained according to the general procedure. Overall yield of the title compound as a white crystalline solid (60%).

CI MS m/z 293.97, 295.95 (MH+).

$^1$H-NMR (400 MHz, DMSO-d₆); δ (ppm): 1.33 (t, 1H), 1.61 (t, 1H), 2.15 (m, 1H), 3.35-3.76 (m, 4H), 7.38 (s, 1H), 7.51 (d, 1H), 7.69 (d, 1H), 8.2 (s, 1H), 9.80 (br. s, 2H).

HPLC (Column C18 3.9×150 mm 5 mkm)—mobile phase: acetonitrile/water+TFA 5/95 (0 min)-100/0(18 min)-100/0 (25 min); flow 1.0 ml/min; RT; Detection UV at 220 nm: First Peak with Retention Time of 10.123 min, area 98.9%; Second Peak with Retention Time of 10.892 min, area 0.6%; Third Peak with Retention Time of 11.058, area 04%; Fourth Peak with Retention Time of 11.752, area 01%.

12. Preparation of 1-(5-bromo-benzo[b]thiophen-2-yl)-3-aza-bicyclo[3.1.0]hexane

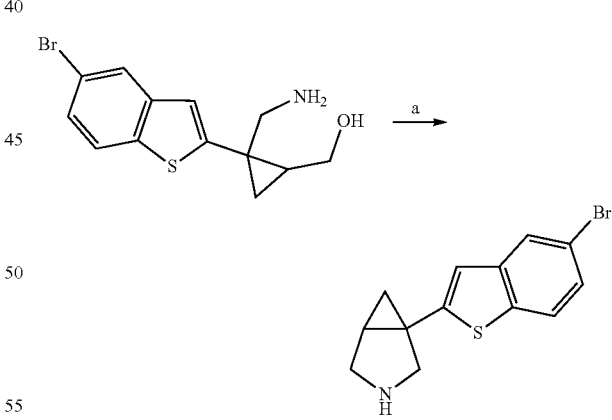

SOCl₂, dioxane, from 0° C. to RT, 1.5 h

The substance and its hydrochloride salt were obtained according to the general procedure. Overall yield of the title compound as a white crystalline solid (72%).

CI MS m/z 293.96, 295.94 (MH+).

$^1$H-NMR (400 MHz, DMSO-d₆); δ (ppm): 1.35 (t, 1H), 1.69 (t, 1H), 2.15 (m, 1H), 3.33-3.80 (m, 4H), 7.35 (s, 1H), 7.44 (d, 1H), 7.87 (d, 1H), 7.94 (s, 1H), 9.70 (br. s, 2H).

HPLC (Column C18 3.9×150 mm 5 mkm)—mobile phase: acetonitrile/water+TFA 5/95 (0 min)-100/0(18 min)-100/0

(25 min); flow 1.0 ml/min; RT; Detection UV at 254 nm: First Peak with Retention Time of 9.127 min, area 1.8%; Second Peak with Retention Time of 10.113 min, area 98.2%

13. Preparation of 1-(6-bromo-benzo[b]thiophen-2-yl)-3-methyl-3-aza-bicyclo(3.1.0]hexane

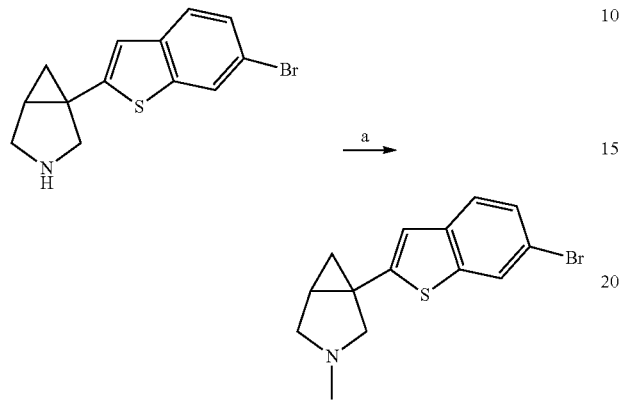

40% CH₂O aqueous solution, Et₃N, CH₃COOH, NaBH(OAc)₃, CH₃CN, RT, overnight

The substance and its hydrochloride salt were obtained according to the general procedure. Overall yield of the title compound as a white crystalline solid (80%).

CI MS m/z 307.95, 309.95 (MH+).

¹H-NMR (400 MHz, DMSO-d₆); δ (ppm): 1.31 (s, 1H), 1.97 (s, 1H), 2.24 (m, 1H), 2.82 (t, 3H), 3.45-3.98 (m, 4H), 7.35 (s, 1H), 7.50 (d, 1H), 7.70 (d, 1H), 8.20 (s, 1H), 11.30 (br. s, 1H).

HPLC (Column C18 3.9×150 mm 5 mkm)—mobile phase: acetonitrile/water+TFA 5/95 (0 min)-100/0(18 min)-100/0 (25 min); flow 1.0 ml/min; RT; Detection UV at 254 nm: First Peak with Retention Time of 9.294 min, area 0.13%; Second Peak with Retention Time of 10.231 min, area 99.87%.

14. Preparation of 1-(5-bromo-benzo[b]thiophen-2-yl)-3-methyl-3-aza-bicyclo[3.1.0]hexane

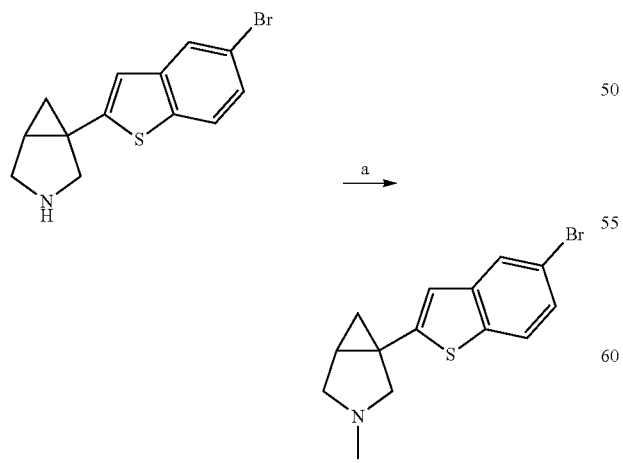

40% CH₂O aqueous solution, Et₃N, CH₃COOH, NaBH(OAc)₃, CH₃CN, RT, overnight

The substance and its hydrochloride salt were obtained according to the general procedure. Overall yield of the title compound as a white crystalline solid (75%).

CI MS m/z 307.96, 309.95 (MH+).

¹H-NMR (400 MHz, DMSO-d₆); δ (ppm): 1.30 (s, 1H), 1.96 (s, 1H), 2.18 (m, 1H), 2.82 (t, 3H), 3.46-4.00 (m, 4H), 7.33 (s, 1H), 7.44 (d, 1H), 7.87 (d, 1H), 7.86 (s, 1H), 11.25 (br. s, 1H).

HPLC (Column C18 3.9×150 mm 5 mkm)—mobile phase: acetonitrile/water+TFA 5/95 (0 min)-100/0(18 min)-100/0 (25 min); flow 1.0 ml/min; RT; Detection UV at 254 nm: First Peak with Retention Time of 9.242 min, area 1.4%; Second Peak with Retention Time of 10.169 min, area 98.6%

15. Preparation of 1-(6-bromo-benzo[b]thiophen-2-yl)-3-aza-bicyclo[3.1.0]hexane-3-carboxylic acid tert-butyl ester

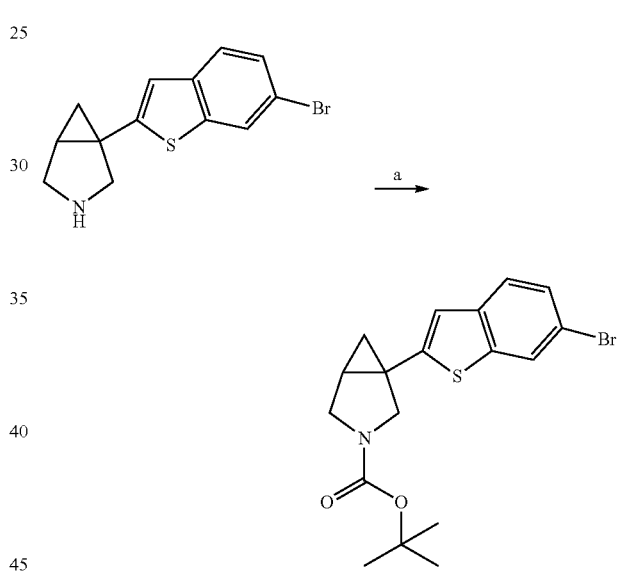

Boc₂O, dicloromethane, RT, overnight

The substance was obtained according to the general procedure and was used on the next step without any purification.

16. Preparation of 1-(5-Bromo-benzo[b]thiophen-2-yl)-3-aza-bicyclo[3.1.0]hexane-3-carboxylic acid tert-butyl ester

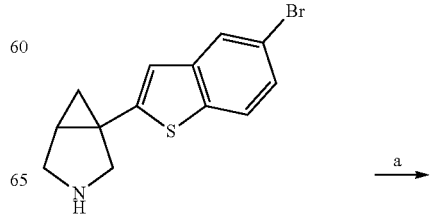

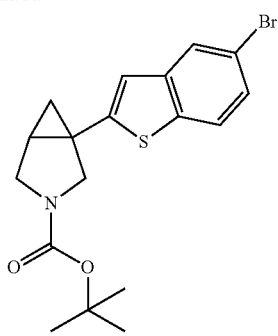

Boc₂O, dicloromethane, RT, overnight

The substance was obtained according to the general procedure and was used on the next step without any purification.

17. Preparation of [2-(3-Aza-bicyclo(3.1.0]hex-1-yl)-benzo[b]thiophen-6-yl]-dimethyl-amine dihydrochloride

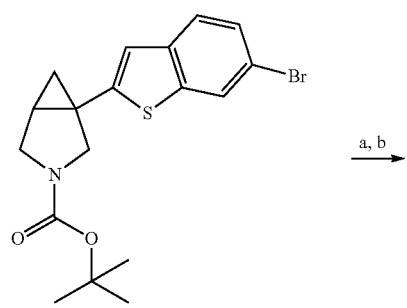

Dimethylamine solution in THF (20%), NaO(i-Am), bis(tri-tert-butyl-phosphine)palladium(0) 6-8 mole %, microwave irradiation at 100° C., 3 h.

5-6 M HCl solution in isopropanol

Boc derivative and the title compound was obtained according to the general procedure.

Yield of the Boc-derivative (87%). Light yellow liquid.

Yield of the title compound (86%). White crystalline solid.

CI MS m/z 259.17 (MH+).

¹H-NMR (400 MHz, DMSO-d₆); δ (ppm): 1.34 (t, 1H), 1.64 (t, 1H), 2.12 (m, 1H), 3.07 (s, 6H), 3.32-3.72 (m, 4H), 7.31 (s, 1H), 7.46 (s, 1H), 7.75 (d, 1H), 7.94 (m, 1H), 9.78 (br. s, 1H), 10.08 (br. s, 1H)

HPLC (Column C18 3.9×150 mm 5 mkm)—mobile phase: acetonitrile/water+TFA 5/95 (0 min)-100/0(18 min)-100/0 (25 min); flow 1.0 ml/min; RT; Detection UV at 254 nm: First Peak with Retention Time of 5.348 min, area 96.9%; Second Peak with Retention Time of 8.537 min, area 2.4%; Third Peak with Retention Time of 9.162 min, area 08%.

18. Preparation of [2-(3-aza-bicyclo[3.1.0]hex-1-yl)-benzo[b]thiophen-S-yl]-dimethyl-amine dihydrochloride

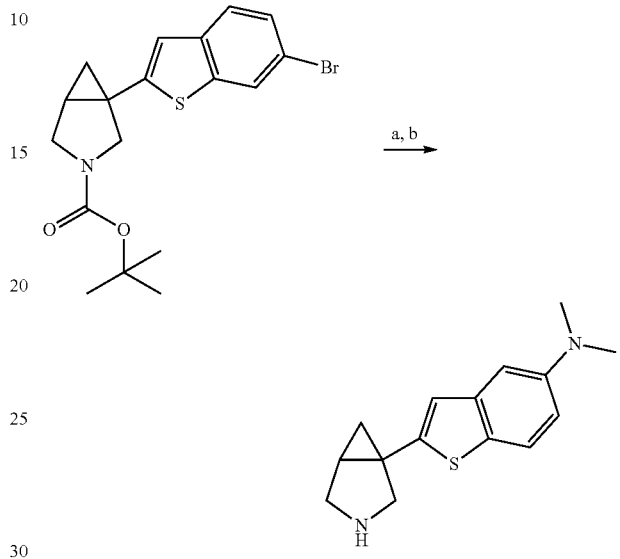

Dimethylamine solution in THF (20%), NaO(i-Am), bis(tri-tert-butyl-phosphine)palladium(0) 6-8 mole %, microwave irradiation at 100° C., 3 h.

5-6 M HCl solution in isopropanol

The Boc derivative and the title compound were obtained according to the general procedure.

Yield of the Boc-derivative (63%). Light yellow liquid.

Yield of the title compound (80%). White crystalline solid.

CI MS m/z 259.00 (MH+).

¹H-NMR (400 MHz, DMSO-d₆); δ (ppm): 1.35 (t, 1H), 1.68 (s, 1H), 2.17 (m, 1H), 3.12 (s, 6H), 3.33-3.72 (m, 4H), 7.4 (s, 1H), 7.54 (s, 1H), 7.88 (m, 1H), 8.00 (d, 1H), 9.80 (br. s, 1H), 10.05 (br. s, 1H)

¹³C-NMR (100 MHz, DMSO-d6) RT; δ (ppm): 16.71, 26.14, 27.59, 44.63, 46.41, 49.05, 113.20, 115.62, 121.07, 123.42, 135.75, 139.93, 142.23, 146.22.

HPLC (Column C18 3.9×150 mm 5 mkm)—mobile phase: acetonitrile/water+TFA 5/95 (0 min)-100/0(18 min)-100/0 (25 min); flow 1.0 ml/min; RT; Detection UV at 220 nm: First Peak with Retention Time of 5.404 min, area 95.9%; Second Peak with Retention Time of 8.992 min, area 4.1%.

19. Preparation of dimethyl-[2-(3-methyl-3-aza-bicyclo[3.1.0]hex-1-yl)-benzo[b]thiophen-6-yl]-amine dihydrochloride

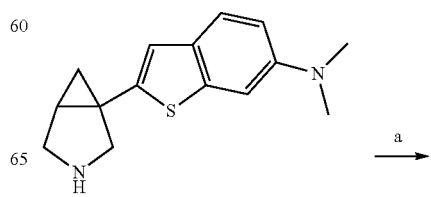

-continued

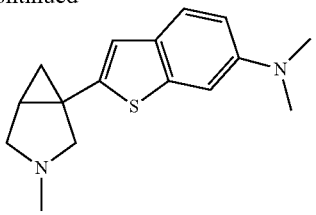

40% CH₂O aqueous solution, Et₃N, CH₃COOH, NaBH(OAc)₃, CH₃CN, RT, overnight

The title compound was obtained according to the general procedure, yielding the title compound as a white crystalline solid (77%).

CI MS m/z 273.00 (MH+).

¹H-NMR (400 MHz, DMSO-d₆); δ (ppm): 1.30 (t, 1H), 2.02 (m, 1H), 2.17 (m, 1H), 2.84 (s, 3H), 3.08 (s, 6H), 3.5-3.97 (m, 4H), 7.4 (s, 1H), 7.43 (s, 1H), 7.75 (d, 1H), 7.90 (m, 1H), 11.40 (br. s, 1H)

HPLC (Column C18 3.9×150 mm 5 mkm)—mobile phase: acetonitrile/water+TFA 5/95 (0 min)-100/0(18 min)-100/0 (25 min); flow 1.0 ml/min; RT; Detection UV at 254 nm: First Peak with Retention Time of 5.383 min, area 96.5%; Second Peak with Retention Time of 8.813 min, area 2.1%; Third Peak with Retention Time of 16.781, area 1.4%.

20. Preparation of [2-(3-isopropyl-3-aza-bicyclo[3.1.0]hex-1-yl)-benzo[b]thiophen-6-yl]-dimethyl-amine dihydrochloride

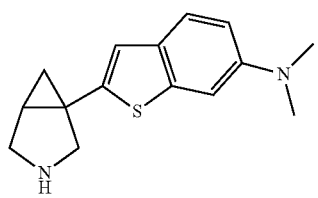

acetone, Et₃N, CH₃COOH, NaBH(OAc)₃, dichloroethane, RT, overnight

The title compound was obtained according to the general procedure, yielding the title compound as a white crystalline solid (75%).

CI MS m/z 301.04 (MH+).

¹H-NMR (400 MHz, DMSO-d₆); δ (ppm): 1.20-1.38 (m, 7H), 2.05-2.02 (m, 2H), 3.04 (s, 6H), 3.15-4.00 (m, 4H), 7.28-7.48 (m, 2H), 7.67-7.94 (m, 2H), 11.35 (br. s, 1H)

HPLC (Column C18 3.9×150 mm 5 mkm)—mobile phase: acetonitrile/water+TFA 5/95 (0 min)-100/0(18 min)-100/0 (25 min); flow 1.0 ml/min; RT; Detection UV at 254 nm: First Peak with Retention Time of 5.946 min, area 98.0%; Second Peak with Retention Time of 9.650 min, area 2.0%.

21. Preparation 12-(3-isopropyl-3-aza-bicyclo[3.1.0]hex-1-yl)-benzo[b]thiophen-5-yl]-dimethyl-anine dihydrochloride

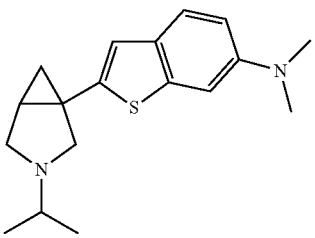

acetone, Et₃N, CH₃COOH, NaBH(OAc)₃, dichloroethane, RT, overnight

The title compound was obtained according to the general procedure, yielding the title compound as a white crystalline solid (65%).

CI MS m/z 301.07 (MH+).

¹H-NMR (400 MHz, DMSO-d₆); δ (ppm): 1.20-1.42 (m, 8H), 2.02 (s, 1H), 3.04 (s, 6H), 3.48-4.05 (m, 4H), 7.38-7.59 (m, 2H), 7.75-7.99 (m, 2H), 11.28 (br. s, 1H)

HPLC (Column C18 3.9×150 mm 5 mkm)—mobile phase: acetonitrile/water+TFA 5/95 (0 min)-100/0(18 min)-100/0 (25 min); flow 1.0 ml/min; RT; Detection UV at 254 nm: First Peak with Retention Time of 5.888 min, area 97.9%; Second Peak with Retention Time of 9.917 min, area 2.1%.

22. Preparation of [2-(3-ethyl-3-aza-bicyclo[3.1.0]hex-1-yl)-benzo[b]thiophen-6-yl]-dimethyl-amine dihydrochloride

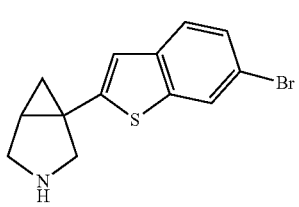

-continued

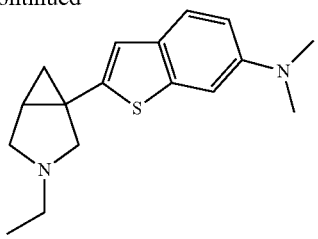

acetyl chloride, Et₃N, methylene chloride, RT, 20 min

Dimethylamine solution in THF (20%), NaO(i-Am), bis(tri-tert-butyl-phosphine)palladium(0) 6-8 mole %, microwave irradiation at 100° C., 3 h.

LiAlH₄, THF, RT, 2 h

The title compound was obtained according to the general procedure, yielding the title compound as a white crystalline solid (62%).

CI MS m/z 287.13 (MH+).

$^1$H-NMR (400 MHz, DMSO-d$_6$); δ (ppm): 1.02-1.50 (m, 7H), 2.12 (m, 2H), 3.03 (s, 6H), 3.31-4.1 (m, 4H), 7.28-7.51 (m, 2H), 7.69-7.98 (m, 2H), 11.28 (br. s, 1H)

HPLC (Column C18 3.9×150 mm 5 mkm)—mobile phase: acetonitrile/water+TFA 5/95 (0 min)-100/0(18 min)-100/0 (25 min); flow 1.0 ml/min; RT; Detection UV at 254 nm: First Peak with Retention Time of 4.079 min, area 96.2%; Second Peak with Retention Time of 8.990 min, area 3.8%.

23. Preparation [2-(3-Ethyl-3-aza-bicyclo[3.1.0]hex-1-yl)-benzo[b]thiophen-5-yl]-dimethyl-amine dihydrochloride

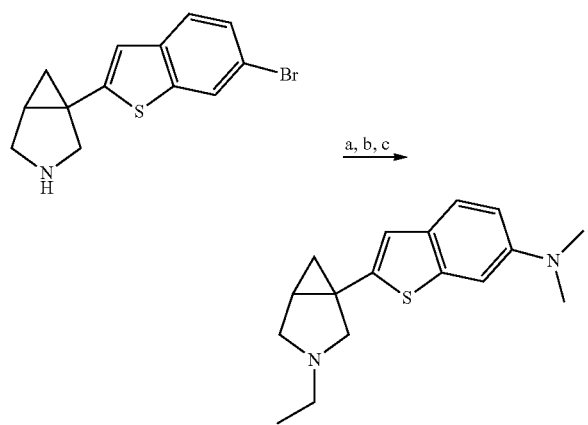

acetyl chloride, Et₃N, methylene chloride, RT, 20 min

Dimethylamine solution in THF (20%), NaO(i-Am), bis(tri-tert-butyl-phosphine)palladium(0) 6-8 mole %, microwave irradiation at 100° C., 3 h.

LiAlH₄, THF, RT, 2 h

The title compound was obtained according to the general procedure, yielding the title compound as a white crystalline solid (68%).

CI MS m/z 287.03 (MH+).

$^1$H-NMR (400 MHz, DMSO-d$_6$); δ (ppm): 1.22-1.34 (m, 5H), 2.04 (d, 1H), 2.18 (s, 1H), 3.04 (s, 6H), 3.15-3.98 (m, 4H), 7.36 (s, 1H), 7.49 (s, 1H), 7.73-7.92 (m, 1H), 7.98 (d, 1H), 11.38 (br. s, 1H)

Example VI

Activity, Selectivity, and Potency of 1-heteroaryl-3-azabicyclo[3.1.0]hexanes for Inhibiting Monoamine Neurotransmitter Transport The ability of the 1-heteroaryl-3-azabicyclo[3.1.0.]hexane of the invention for inhibiting transport of norepinephrine (NE) and/or dopamine (DA) and/or serotonin (5-HT) were evaluated using cell lines (such as the HEK 293 cell line) that stably express recombinant human NE, DA, and 5-HT transporters, respectively. The techniques for stably transfecting mammalian cell lines with neurotransmitter transporters and measuring the effects of drugs on amine uptake have been described in the literature (e.g., Gu, H., et al. J. Biol. Chem. 269:7124-7130, 1994; Eshleman AJ, J Pharmacol Exp Ther 289:877-885, 1999) and well known to those skilled in the art.

A basic technique for measuring the ability of a compound to inhibit [$^3$H]NE, DA, and 5-HT uptake in cell lines recombinantly expressing human transporters has been described (Eshleman, et al., 1999). In brief, cell suspensions (HEK 293 cells expressing the 5-HT transporter, MDCK cells expressing the NE transporter, and CHO-K1 cells expressing the DA transporter, respectively) can be prepared for assay by removing the medium from cells grown on tissue culture dishes, then washing the plates with buffered medium. Cells can then be gently scraped from the plates and cell clusters separated by trituration with a pipette for 5-10 aspiration/ejection cycles. To these cell suspensions were added test drugs (final concentrations generally from 0.01-5 μM) and Tris/Hepes buffer, pH 7.1 (also containing 120 mM NaCl, 1.2 mM CalCl₂, 1.2 mM MgSO₄, 5 mM D-glucose, and 1 mM ascorbic acid). Following a preincubation of the isolated cells at 25° C., either [$^3$H]DA, [$^3$H]5-HT, or [$^3$H]NE was added and the incubation continued an additional 10 minutes. Radiolabelled neurotransmitter uptake was terminated by vacuum filtration and washing through Whatman glass fiber filters (GF/C), and the radioactivity retained on the filters was measured by liquid scintillation spectrometry. Specific uptake was defined as the difference in uptake observed in the absence and presence of a large molar excess of nomifensine, desipramine, or fluoxetine (for [$^3$H]DA, [$^3$H]NE or [$^3$H]5-HT, respectively].

The results of these assays are shown in Table 2, below, which indicates, for each of the exemplary compounds, the structure of the substituent, and levels of observed uptake inhibition percentage for each of the indicated neurotransmitters at a fixed concentration of compound, or the IC$_{50}$ value, defined as that concentration of compound necessary to inhibit uptake by 50%. These are standard terms known to those skilled in the art.

TABLE 2

Inhibition of Biogenic Amine Uptake By Exemplary Substituted 1-Aryl-3-Azabicyclo[3.1.0.]hexanes

| Structure | Uptake inh. % at 1 μM NE | Uptake inh. % at 1 μM 5-HT | Uptake inh. % at 1 μM DA | Uptake IC50 (nM) NE | Uptake IC50 (nM) 5-HT | Uptake IC50 (nM) DA |
|---|---|---|---|---|---|---|
| benzofuran-2-yl, N-Me · HCl | | | | 400 | 340 | 630 |
| benzofuran-3-yl, NH · HCl | 77 | 57 | 63 | 82 | 188 | 770 |
| benzofuran-3-yl, N-Me · HCl | 82 | 45 | 67 | 138 | 1450 | 475 |
| 5-methylthiophen-2-yl, NH · HCl | 59 | 35 | 20 | | | |
| quinolin-3-yl, NH · HCl | 64 | 14 | 10 | | | |
| 1-methylindol-2-yl, N-Me · HCl | 35 | 64 | 19 | | | |
| 1-methylindol-2-yl, N-Et · HCl | 29 | 65 | 32 | | | |

TABLE 2-continued

Inhibition of Biogenic Amine Uptake By Exemplary Substituted 1-Aryl-3-Azabicyclo[3.1.0.]hexanes

| Structure | Uptake inh. % at 1 μM NE | Uptake inh. % at 1 μM 5-HT | Uptake inh. % at 1 μM DA | Uptake IC50 (nM) NE | Uptake IC50 (nM) 5-HT | Uptake IC50 (nM) DA |
|---|---|---|---|---|---|---|
| (1-Aryl-3-azabicyclo[3.1.0]hexane with 5-chlorobenzothiophene, NH, HCl) | 50 | 18 | 13 | | | |
| (1-Aryl-3-azabicyclo[3.1.0]hexane with 5-chlorobenzothiophene, N-Me, HCl) | 39 | 50 | 1 | | | |
| (1-Aryl-3-azabicyclo[3.1.0]hexane with N-methylindol-5-yl, N-Me, HCl) | 53 | 71 | 45 | 186 | 154 | 811 |
| (1-Aryl-3-azabicyclo[3.1.0]hexane with N-methylindol-5-yl, N-Et, HCl) | 39 | 59 | 65 | 138 | 308 | 215 |
| (1-Aryl-3-azabicyclo[3.1.0]hexane with N-methylindol-2-yl, N-iPr, HCl) | 13 | 83 | 7 | | | |
| (1-Aryl-3-azabicyclo[3.1.0]hexane with benzothiazol-2-yl, NH, HCl) | 72 | 7 | 5 | | | |

TABLE 2-continued

Inhibition of Biogenic Amine Uptake By Exemplary Substituted 1-Aryl-3-Azabicyclo[3.1.0.]hexanes

| Structure | Uptake inh. % at 1 µM NE | Uptake inh. % at 1 µM 5-HT | Uptake inh. % at 1 µM DA | Uptake IC50 (nM) NE | Uptake IC50 (nM) 5-HT | Uptake IC50 (nM) DA |
|---|---|---|---|---|---|---|
| (benzothiophene structure, NH, HCl) | 90 | 66 | 91 | 20 | 88 | 82 |
| (benzothiophene structure, N-Me, HCl) | 71 | 92 | 88 | 60 | 34 | 98 |
| (benzothiophene structure, stereo, NH, HCl) | 97 | 96 | 90 | 14 | 193 | 52 |
| (benzothiophene structure, stereo, NH, HCl) | 84 | 76 | 90 | 99 | 481 | 149 |
| (benzothiophene structure, stereo, N-Me, HCl) | 89 | 99 | 82 | 71 | 54 | 224 |
| (benzothiophene structure, stereo, N-Me, HCl) | 75 | 89 | 83 | 107 | 263 | 195 |
| (6-F-benzothiophene structure, NH, HCl) | 98 | 100 | 99 | | | |

TABLE 2-continued

Inhibition of Biogenic Amine Uptake By Exemplary Substituted 1-Aryl-3-Azabicyclo[3.1.0.]hexanes

| Structure | Uptake inh. % at 1 μM NE | Uptake inh. % at 1 μM 5-HT | Uptake inh. % at 1 μM DA | Uptake IC50 (nM) NE | Uptake IC50 (nM) 5-HT | Uptake IC50 (nM) DA |
|---|---|---|---|---|---|---|
| [structure: N-methyl azabicyclo[3.1.0]hexane with fluoro-benzothiophene, HCl] | 88 | 99 | 94 | | | |
| [structure: NH azabicyclo[3.1.0]hexane with quinoline, HCl] | 68 | 63 | 17 | | | |
| [structure: N-methyl azabicyclo[3.1.0]hexane with quinoline, HCl] | 13 | 93 | 12 | | | |
| [structure: NH azabicyclo[3.1.0]hexane with fluoro-benzothiophene, HCl] | 91 | 98 | 78 | | | |
| [structure: N-methyl azabicyclo[3.1.0]hexane with fluoro-benzothiophene, HCl] | 70 | 94 | 63 | | | |

Readily discernable from the foregoing results is the high degree of diversity with respect to the biological activity changes that were achieved by differentially altering N-substituents to yield novel 1-heteroaryl-3-azabicyclo[3.1.0.]hexanes according to the invention-whereby the absolute potency at any one transporter may be altered dramatically, and in distinct patterns among the exemplified compounds. These different relative potencies at the three transporters yield profound and distinct therapeutic potentials among the different, novel compounds of the invention. Both the absolute changes in potency and the changes in relative potency among the three transporters described herein for exemplary compounds of the invention would not have been expected or predictable with a reasonable expectation of success by persons of ordinary skill in the art The data provided in Table 2 demonstrate that several of the 1-heteroaryl-3-azabicyclo[3.1.0.]hexanes of the invention are potent (nM) inhibitors of norepinephrine and/or serotonin and/or dopamine uptake. As such, the compounds and related formulations and methods of the invention provide neurobiologically active tools for modulating biogenic amine transport in mammalian subjects. These subjects may include in vitro or ex vivo mammalian cell, cell culture, tissue culture, or organ explants, as well as human and other mammalian individuals presenting with, or at heightened risk for developing, a central nervous system (CNS) disorder, such as pain, anxiety, or depression.

In certain embodiments, neurobiologically active compositions comprising a 1-heteroaryl-3-azabicyclo[3.1.0.]hexane of the invention are effective to inhibit cellular uptake of norepinephrine in a mammalian subject. In other embodiments, these compositions will effectively inhibit cellular uptake of serotonin in mammals. Other compositions of the invention will be effective to inhibit cellular uptake of dopamine in mammalian subjects.

As illustrated by the foregoing examples, additional neurobiologically active compositions of the invention will be effective to inhibit cellular uptake of multiple biogenic amine neurotransmitters in mammalian subjects, for example, norepinephrine and serotonin, norepinephrine and dopamine, or serotonin and dopamine. In additional embodiments, the compositions of the invention are effective to inhibit cellular uptake of norepinephrine, serotonin and dopamine in mammalian subjects.

In further-detailed embodiments, as exemplified by the results presented in Table 2, neurobiologically active compositions of the invention surprisingly inhibit cellular reuptake of two, or three, biogenic amines selected from norepinephrine, serotonin and dopamine in a mammalian subject "non-uniformly" across the affected range of multiple targets. The distinct double and triple reuptake inhibition activity profiles demonstrated herein for exemplary compounds of the invention illustrate the powerful and unpredictable nature of structural variations for the compounds, and further evince the ability to follow the teachings of the present disclosure to produce, select, and employ other substituted candidates according to the invention having distinct activity profiles to fulfill additional therapeutic uses within the invention for treating diverse CNS disorders.

In exemplary embodiments, this differential inhibition may yield a profile of reuptake inhibition activities for all three neurotransmitters, norepinephrine, serotonin, and dopamine, respectively, in approximate reuptake inhibition profiles as determined in Table 2 selected from the following relative potencies: (1:1:10); (1:1:6); (1:2:1); (1:0.5:2); (1:1:3); (1:3:3); (1:1:2); and (1:1:1)-which values will correlate in a measurable way with novel in vivo reuptake inhibition profiles/ratios as will be readily determined by those skilled in the art.

In related embodiments, neurobiologically active compositions of the invention inhibit cellular uptake of two, or three, biogenic amine neurotransmitters non-uniformly, for example by inhibiting uptake of at least one member of a group of transmitters including norepinephrine, serotonin, and dopamine by a factor of two- to ten-fold greater than a potency of the same composition to inhibit uptake of one or more different neurotransmitter(s). In exemplary embodiments, compositions of the invention comprising a 1-heteroaryl-3-azabicyclo[3.1.0.]hexane inhibit cellular uptake of serotonin by a factor of at least approximately two-fold, or three-fold, greater than a potency of the same composition to inhibit uptake of norepinephrine, dopamine, or both norepinephrine and dopamine. In other exemplary embodiments, different 1-heteroaryl-3-azabicyclo[3.1.0.]hexanes of the invention inhibit cellular uptake of dopamine by a factor of at least approximately two-fold, six-fold, or ten-fold, greater than a potency of the composition for inhibiting uptake of norepinephrine, serotonin, or both norepinephrine and serotonin. In additional exemplary embodiments, the compositions described herein inhibit cellular uptake of norepinephrine by a factor of at least approximately two-fold greater than a potency of the same composition for inhibiting uptake of serotonin. In different exemplary embodiments, compositions are provided that inhibit cellular uptake of dopamine by a factor of at least approximately two-fold greater than potency of the composition for inhibiting uptake of serotonin.

In yet additional embodiments, neurobiologically active compositions are provided that exhibit approximately equivalent potency for inhibiting cellular uptake of norepinephrine and serotonin, while at the same time inhibiting dopamine uptake by a factor of at least approximately two-fold, or six-fold, greater than the potency for inhibiting uptake of norepinephrine and serotonin. In still other exemplary embodiments, compositions of the invention exhibit approximately equivalent potency for inhibiting cellular uptake of serotonin and dopamine, while at the same time inhibiting norepinephrine by a factor of no greater than approximately half the potency for inhibiting uptake of serotonin and dopamine. In certain embodiments, compositions of the invention exhibit approximately equivalent potency for inhibiting cellular uptake of norepinephrine, serotonin, and dopamine.

Compounds of the invention that inhibit the uptake of norepinephrine, serotonin, and/or dopamine have a wide range of therapeutic uses, principally to treat CNS disorders as described above. Certain CNS disorders contemplated herein will be more responsive to a compound of the invention that preferentially inhibits, for example, dopamine uptake relative to norepinephrine and/or serotonin uptake, as in the case of some forms of depression. Other disorders, for example pain, will be determined to be more responsive to compounds of the invention that more potently inhibit norepinenephrine reuptake relative to serotonin reuptake and dopamine reuptake. Other CNS disorders, for example, attention deficit hyperactivity disorder (ADHD), may respond better to compounds of the invention that preferentially inhibit dopamine and norepinephrine reuptake relative to serotonin reuptake. Thus, the host of exemplary compounds described herein, which provide a range of reuptake inhibition profiles/ratios, will provide useful drug candidates for a diverse range of CNS disorders, and will effectively treat specific disorders with lower side effect profiles than currently available drugs.

It is to be understood that this invention is not limited to the particular formulations, process steps, and materials disclosed herein as such formulations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

REFERENCES

Basile, A. S., et al., *J. Pharmacol. Exp. Ther.,* 321:1208-1225 (2007)
Skolnick, P. et al., Eur. J. Pharmacol. 461:99 (2003)
Skolnick, P. et al., Life Sci. 73: 3175-3179 (2003)
Skolnick, P., et al., CNS Drug Reviews (2006)
Briley, M., Hum. Psychopharmacol. Clin. Exp. 19:S21-S25 (2004)
Skolnick, P. in "*Dopamine and glutamate in psychiatric disorders,*" W. Schmidt, Editor, Humana Press, Totowa, Chapter 9, pp. 199-214 (2005)

Atkinson, J. H. et al., Pain 83:137-145 (1999)

Povlock, S. L. and Amara, S. G., in "*Neurotransmitter transporters: structure, function, and regulation*," Reith MEA, Editor, Humana Press, Totowa, pp. 1-28 (1997)

Eshleman, A. J. et al., Journal of Pharmacology & Experimental Therapeutics 289:877-885 (1999)

"Nitrogen Protecting Groups in Organic Synthesis", John Wiley and Sons, New York, N.Y., 1981, Chapter 7

"Nitrogen Protecting Groups in Organic Chemistry", Plenum Press, New York, N.Y., 1973, Chapter 2

Green, T. W. and Wuts, P. G. M. in "Protective Groups in Organic Chemistry", 3rd edition, John Wiley & Sons, New York, N.Y., 1999

Quick Reference to the Diagnostic Criteria From DSM-IV (Diagnostic and Statistical Manual of Mental Disorders, Fourth Edition), The American Psychiatric Association, Washington, D.C., 1994

Perovic, S. and Muller, W. E., Arzneimittelforschung 45: 1145-1148 (1995)

Gu, H., et al. J. Biol. Chem. 269:7124-7130 (1994)

U.S. Pat. No. 4,122,193; Scherm et al.; Oct. 24, 1978

U.S. Pat. No. 6,132,724; Blum; Oct. 17, 2000

U.S. patent application Ser. No. 11/371,178; Skolnick, et al.; filed Mar. 7, 2006

What is claimed is:

1. A compound of the following Formula I:

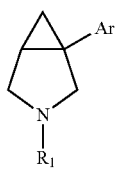

Formula I and pharmaceutically acceptable salts, enantiomers, polymorphs, solvates, hydrates or prodrugs thereof, wherein:

Ar is a heterocyclic aryl group selected from furan, methylfuran, pyrrole, imidazole, pyrazole, triazole, tetrazole, thiazole, isothiazole, methoxypyridine, pyridazine, pyrazine, triazine, indole, methylindole, benzofuran, benzothiophene, benzothiazole, isoquinoline, cinnoline, phthalazine, quinazoline, chromane and isochromane, and Ar is either unsubstituted or substituted with one or more substituents independently selected from fluoro, chloro, bromo, iodo, —$NO_2$, —CN, —$NH_2$, carboxy, $C_{2-8}$ alkenyl, $C_{2-8}$ alkynyl, halo($C_{1-8}$)alkyl, hydroxy, trifluoromethyl, $C_{3-8}$ cycloalkyl, $C_{1-3}$ alkoxy, $C_{1-3}$ alkoxy ($C_{1-3}$)alkyl, carboxy($C_{1-3}$)alkyl, $C_{1-3}$ alkanoyl, halo($C_{1-3}$)alkoxyl, $C_{1-8}$ alkylamino, and di($C_{1-8}$)alkylamino; and $R_1$ is selected from hydrogen, unsubstituted $C_{1-10}$ alkyl, $C_{3-8}$ cycloalkyl, $C_{2-10}$ alkenyl, and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy.

2. A compound of the following Formula Ia:

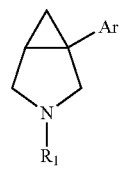

Formula Ia or a pharmaceutically acceptable salt thereof, wherein:

Ar is furan, methylfuran, fluorobenzothiophene, methoxypyridine, benzofuran, benzothiophene, chlorobenzothiophene, benzothiazole, indole, or methylindole; and $R_1$ is hydrogen, methyl, ethyl, propyl, or isopropyl.

3. The compound according to claim 1, wherein the compound is selected from the group consisting of:

1-(5-methylfuran-2-yl)-3-azabicyclo[3.1.0]hexane;
1-(6-methoxypyridin-3-yl)-3-azabicyclo[3.1.0]hexane;
1-(6-methoxypyridin-3-yl)-3-methyl-3-azabicyclo[3.1.0]hexane;
1-(benzofuran-2-yl)-3-methyl-3-azabicyclo[3.1.0]hexane;
1-(benzofuran-3-yl)-3-azabicyclo[3.1.0]hexane;
1-(benzofuran-3-yl)-3-methyl-3-azabicyclo[3.1.0]hexane;
1-methyl-2-(3-methyl-3-azabicyclo[3.1.0]hexan-1-yl)-1H-indole;
2-(3-ethyl-3-azabicyclo[3.1.0]hexan-1-yl)-1-methyl-1H-indole;
2-(3-isopropyl-3-azabicyclo[3.1.0]hexan-1-yl)-1-methyl-1H-indole;
1-methyl-5-(3-methyl-3-azabicyclo[3.1.0]hexan-1-yl)-1H-indole;
5-(3-ethyl-3-azabicyclo[3.1.0]hexan-1-yl)-1-methyl-1H-indole;
5-(3-isopropyl-3-azabicyclo[3.1.0]hexan-1-yl)-1-methyl-1H-indole;
1-(5-chlorobenzo[b]thiophen-3-yl)-3-azabicyclo[3.1.0]hexane;
1-(5-chlorobenzo[b]thiophen-2-yl)-3-methyl-3-azabicyclo[3.1.0]hexane;
1-(5-chlorobenzo[b]thiophen-3-yl)-3-methyl-3-azabicyclo[3.1.0]hexane;
1-(benzo[b]thiophen-2-yl)-3-aza-bicyclo[3.1.0]hexane;
1-(benzo[b]thiophen-2-yl)-3-methyl-3-aza-bicyclo[3.1.0]hexane;
1-(6-fluorobenzo[b]thiophen-2-yl)-3-aza-bicyclo[3.1.0]hexane;
1-(6-fluorobenzo[b]thiophen-2-yl)-3-methyl-3-aza-bicyclo[3.1.0]hexane;
1-(5-fluorobenzo[b]thiophen-2-yl)-3-aza-bicyclo[3.1.0]hexane;
1-(5-fluorobenzo[b]thiophen-2-yl)-3-methyl-3-aza-bicyclo[3.1.0]hexane; and
2-(3-azabicyclo[3.1.0]hexan-1-yl)-benzo[d]thiazole;

or a pharmaceutically acceptable salt thereof.

4. The compound according to claim 2 or a pharmaceutically acceptable salt thereof, wherein Ar is benzothiophene, fluorobenzothiophene, or chlorobenzothiophene.

5. The compound according to claim 3, wherein the compound is selected from the group consisting of:

1-(5-chlorobenzo[b]thiophen-3-yl)-3-azabicyclo[3.1.0]hexane;

1-(5-chlorobenzo[b]thiophen-2-yl)-3-methyl-3-azabicyclo[3.1.0]hexane;
1-(5-chlorobenzo[b]thiophen-3-yl)-3-methyl-3-azabicyclo[3.1.0]hexane;
1-(benzo[b]thiophen-2-yl)-3-aza-bicyclo[3.1.0]hexane;
1-(benzo[b]thiophen-2-yl)-3-methyl-3-aza-bicyclo[3.1.0]hexane;
1-(6-fluorobenzo[b]thiophen-2-yl)-3-aza-bicyclo[3.1.0]hexane;
1-(6-fluorobenzo[b]thiophen-2-yl)-3-methyl-3-aza-bicyclo[3.1.0]hexane;
1-(5-fluorobenzo[b]thiophen-2-yl)-3-aza-bicyclo[3.1.0]hexane; and
1-(5-fluorobenzo[b]thiophen-2-yl)-3-methyl-3-aza-bicyclo[3.1.0]hexane;
or a pharmaceutically acceptable salt thereof.

6. The compound according to claim 5, wherein the compound is 1-(benzo[b]thiophen-2-yl)-3-aza-bicyclo[3.1.0]hexane or a pharmaceutically acceptable salt thereof.

7. The compound according to claim 6, wherein the compound is 1-(benzo[b]thiophen-2-yl)-3-aza-bicyclo[3.1.0]hexane hydrochloride.

8. The compound according to claim 6, wherein the compound is (1S,5S)-1-(benzo[b]thiophen-2-yl)-3-azabicyclo[3.1.0]hexane or a pharmaceutically acceptable salt thereof.

9. The compound according to claim 8, wherein the compound is (1S,5S)-1-(benzo[b]thiophen-2-yl)-3-azabicyclo[3.1.0]hexane hydrochloride.

10. The compound according to claim 6, wherein the compound is (1R,5R)-1-(benzo[b]thiophen-2-yl)-3-azabicyclo[3.1.0]hexane or a pharmaceutically acceptable salt thereof.

11. The compound according to claim 10, wherein the compound is (1R,5R)-1-(benzo[b]thiophen-2-yl)-3-azabicyclo[3.1.0]hexane hydrochloride.

12. The compound according to claim 5, wherein the compound is 1-(benzo[b]thiophen-2-yl)-3-methyl-3-aza-bicyclo[3.1.0]hexane or a pharmaceutically acceptable salt thereof.

13. The compound according to claim 12, wherein the compound is 1-(benzo[b]thiophen-2-yl)-3-methyl-3-aza-bicyclo[3.1.0]hexane hydrochloride.

14. The compound according to claim 12, wherein the compound is (1S,5S)-1-(benzo[b]thiophen-2-yl)-3-methyl-3-azabicyclo[3.1.0]hexane or a pharmaceutically acceptable salt thereof.

15. The compound according to claim 14, wherein the compound is (1S,5S)-1-(benzo[b]thiophen-2-yl)-3-methyl-3-azabicyclo[3.1.0]hexane hydrochloride.

16. The compound according to claim 12, wherein the compound is (1R,5R)-1-(benzo[b]thiophen-2-yl)-3-methyl-azabicyclo[3.1.0]hexane or a pharmaceutically acceptable salt thereof.

17. The compound according to claim 16, wherein the compound is (1R,5R)-1-(benzo[b]thiophen-2-yl)-3-methyl-azabicyclo[3.1.0]hexane hydrochloride.

18. The compound according to claim 5, wherein the compound is 1-(6-fluorobenzo[b]thiophen-2-yl)-3-azabicyclo[3.1.0]hexane or a pharmaceutically acceptable salt thereof.

19. The compound according to claim 18, wherein the compound is 1-(6-fluorobenzo[b]thiophen-2-yl)-3-azabicyclo[3.1.0]hexane hydrochloride.

20. The compound according to claim 18, wherein the compound is (1S,5S)-1-(6-fluorobenzo[b]thiophen-2-yl)-3-azabicyclo[3.1.0]hexane or a pharmaceutically acceptable salt thereof.

21. The compound according to claim 20, wherein the compound is (1S,5S)-1-(6-fluorobenzo[b]thiophen-2-yl)-3-azabicyclo[3.1.0]hexane hydrochloride.

22. The compound according to claim 18, wherein the compound is (1R,5R)-1-(6-fluorobenzo[b]thiophen-2-yl)-3-azabicyclo[3.1.0]hexane or a pharmaceutically acceptable salt thereof.

23. The compound according to claim 22, wherein the compound is (1R,5R)-1-(6-fluorobenzo[b]thiophen-2-yl)-3-azabicyclo[3.1.0]hexane hydrochloride.

24. The compound according to claim 5, wherein the compound is 1-(6-fluorobenzo[b]thiophen-2-yl)-3-methyl-3-aza-bicyclo[3.1.0]hexane or a pharmaceutically acceptable salt thereof.

25. The compound according to claim 5, wherein the compound is 1-(5-fluorobenzo[b]thiophen-2-yl)-3-aza-bicyclo[3.1.0]hexane or a pharmaceutically acceptable salt thereof.

26. The compound according to claim 5, wherein the compound is 1-(5-fluorobenzo[b]thiophen-2-yl)-3-methyl-3-aza-bicyclo[3.1.0]hexane or a pharmaceutically acceptable salt thereof.

27. A compound selected from the group consisting of:
N,N-dimethyl-2-(3-methyl-3-azabicyclo[3.1.0]hexane-1-yl)benzo[b]thiophen-5-amine;
1-(5-bromobenzo[b]thiophen-2-yl)-3-azabicyclo[3.1.0]hexane;
1-(5-bromobenzo[b]thiophen-2-yl)-3-methyl-3-azabicyclo[3.1.0]hexane;
2-(3-azabicyclo[3.1.0]hexan-1-yl)-N,N-dimethylbenzo[b]thiophen-5-amine;
2-(3-ethyl-3-azabicyclo[3.1.0]hexan-1-yl)-N,N-dimethylbenzo[b]thiophen-5-amine;
2-(3-isopropyl-3-azabicyclo[3.1.0]hexan-1-yl)-N,N-dimethylbenzo[b]thiophen-5-amine;
1-(6-bromobenzo[b]thiophen-2-yl)-3-azabicyclo[3.1.0]hexane;
1-(6-bromobenzo[b]thiophen-2-yl)-3-methyl-3-azabicyclo[3.1.0]hexane;
2-(3-azabicyclo[3.1.0]hexan-1-yl)-N,N-dimethylbenzo[b]thiophen-6-amine;
N,N-dimethyl-2-(3-methyl-3-azabicyclo[3.1.0]hexan-1-yl)benzo[b]thiophen-6-amine;
2-(3-ethyl-3-azabicyclo[3.1.0]hexan-1-yl)-N,N-dimethylbenzo[b]thiophen-6-amine; and
2-(3-isopropyl-3-azabicyclo[3.1.0]hexan-1-yl)-N,N-dimethylbenzo[b]thiophen-6-amine;
or a pharmaceutically acceptable salt thereof.

28. A pharmaceutical composition comprising a compound according to claim 1 or a pharmaceutically acceptable salt, enantiomer, polymorph, solvate, hydrate or prodrug thereof and a pharmaceutically acceptable carrier or vehicle therefore.

29. A pharmaceutical composition comprising a compound according to claim 2 or a pharmaceutically acceptable salt thereof and a pharmaceutically acceptable carrier or vehicle therefore.

30. The pharmaceutical composition according to claim 29 comprising a compound selected from the group consisting of:
1-(5-methylfuran-2-yl)-3-azabicyclo[3.1.0]hexane;
1-(6-methoxypyridin-3-yl)-3-azabicyclo[3.1.0]hexane;
1-(6-methoxypyridin-3-yl)-3-methyl-3-azabicyclo[3.1.0]hexane;
1-(benzofuran-2-yl)-3-methyl-3-azabicyclo[3.1.0]hexane;
1-(benzofuran-3-yl)-3-azabicyclo[3.1.0]hexane;
1-(benzofuran-3-yl)-3-methyl-3-azabicyclo[3.1.0]hexane;
1-methyl-2-(3-methyl-3-azabicyclo[3.1.0]hexan-1-yl)-1H-indole;

2-(3-ethyl-3-azabicyclo[3.1.0]hexan-1-yl)-1-methyl-1H-indole;

2-(3-isopropyl-3-azabicyclo[3.1.0]hexan-1-yl)-1-methyl-1H-indole;

1-methyl-5-(3-methyl-3-azabicyclo[3.1.0]hexan-1-yl)-1H-indole;

5-(3-ethyl-3-azabicyclo[3.1.0]hexan-1-yl)-1-methyl-1H-indole;

5-(3-isopropyl-3-azabicyclo[3.1.0]hexan-1-yl)-1-methyl-1H-indole;

1-(5-chlorobenzo[b]thiophen-3-yl)-3-azabicyclo[3.1.0]hexane;

1-(5-chlorobenzo[b]thiophen-2-yl)-3-methyl-3-azabicyclo[3.1.0]hexane;

1-(5-chlorobenzo[b]thiophen-3-yl)-3-methyl-3-azabicyclo[3.1.0]hexane;

1-(benzo[b]thiophen-2-yl)-3-aza-bicyclo[3.1.0]hexane;

1-(benzo[b]thiophen-2-yl)-3-methyl-3-aza-bicyclo[3.1.0]hexane;

1-(6-fluorobenzo[b]thiophen-2-yl)-3-aza-bicyclo[3.1.0]hexane;

1-(6-fluorobenzo[b]thiophen-2-yl)-3-methyl-3-aza-bicyclo[3.1.0]hexane;

1-(5-fluorobenzo[b]thiophen-2-yl)-3-aza-bicyclo[3.1.0]hexane;

1-(5-fluorobenzo[b]thiophen-2-yl)-3-methyl-3-aza-bicyclo[3.1.0]hexane; and 2-(3-azabicyclo[3.1.0]hexan-1-yl)-benzo[d]thiazole;

or a pharmaceutically acceptable salt thereof.

31. The pharmaceutical composition according to claim 30 comprising 1-(benzo[b]thiophen-2-yl)-3-aza-bicyclo[3.1.0]hexane or a pharmaceutically acceptable salt thereof.

32. The pharmaceutical composition according to claim 31 comprising (1S,5S)-1-(benzo[b]thiophen-2-yl)-3-azabicyclo[3.1.0]hexane or a pharmaceutically acceptable salt thereof.

33. The pharmaceutical composition according to claim 31 comprising (1R,5R)-1-(benzo[b]thiophen-2-yl)-3-azabicyclo[3.1.0]hexane or a pharmaceutically acceptable salt thereof.

34. The pharmaceutical composition according to claim 30 comprising 1-(benzo[b]thiophen-2-yl)-3-methyl-3-aza-bicyclo[3.1.0]hexane or a pharmaceutically acceptable salt thereof.

35. The pharmaceutical composition according to claim 34 comprising (1S,5S)-1-(benzo[b]thiophen-2-yl)-3-methyl-3-azabicyclo[3.1.0]hexane or a pharmaceutically acceptable salt thereof.

36. The pharmaceutical composition according to claim 34 comprising (1R,5R)-1-(benzo[b]thiophen-2-yl)-3-methyl-azabicyclo[3.1.0]hexane or a pharmaceutically acceptable salt thereof.

37. The pharmaceutical composition according to claim 30 comprising 1-(6-fluorobenzo[b]thiophen-2-yl)-3-azabicyclo[3.1.0]hexane or a pharmaceutically acceptable salt thereof.

38. The pharmaceutical composition according to claim 37 comprising (1S,5S)-1-(6-fluorobenzo[b]thiophen-2-yl)-3-azabicyclo[3.1.0]hexane or a pharmaceutically acceptable salt thereof.

39. The pharmaceutical composition according to claim 37 comprising (1R,5R)-1-(6-fluorobenzo[b]thiophen-2-yl)-3-azabicyclo[3.1.0]hexane or a pharmaceutically acceptable salt thereof.

40. A pharmaceutical composition comprising a compound according to claim 27 or a pharmaceutically acceptable salt thereof and a pharmaceutically acceptable carrier or vehicle therefore.

41. A method of inhibiting cellular uptake of one or more biogenic amine neurotransmitters selected from norepinephrine, serotonin, and dopamine in a mammalian subject in need thereof comprising administering a compound or a pharmaceutically acceptable salt thereof according to claim 3.

* * * * *